(12) United States Patent
Nishizawa et al.

(10) Patent No.: US 8,741,871 B2
(45) Date of Patent: Jun. 3, 2014

(54) TREHALOSE COMPOUND, METHOD FOR PRODUCING SAME, AND PHARMACEUTICAL PRODUCT CONTAINING THE COMPOUND

(75) Inventors: Mugio Nishizawa, Tokushima (JP); Reiko Nishizawa, legal representative, Tokushima (JP); Hiroshi Imagawa, Tokushima (JP); Hirofumi Yamamoto, Tokushima (JP); Jun Sakurai, Tokushima (JP); Masataka Oda, Tokushima (JP)

(73) Assignee: Glytech, Inc., Kyoto (JP)

( * ) Notice: Subject to any disclaimer, the term of this patent is extended or adjusted under 35 U.S.C. 154(b) by 145 days.

(21) Appl. No.: 13/126,842

(22) PCT Filed: Oct. 27, 2009

(86) PCT No.: PCT/JP2009/005650
§ 371 (c)(1),
(2), (4) Date: May 25, 2011

(87) PCT Pub. No.: WO2010/050178
PCT Pub. Date: May 6, 2010

(65) Prior Publication Data
US 2011/0218171 A1 Sep. 8, 2011

(30) Foreign Application Priority Data

Oct. 31, 2008 (JP) .................................. 2008-282613
Feb. 27, 2009 (JP) .................................. 2009-046824

(51) Int. Cl.
*A61K 31/7024* (2006.01)
*C07H 13/06* (2006.01)
*C07H 13/08* (2006.01)

(52) U.S. Cl.
USPC .............................................. 514/53; 536/119

(58) Field of Classification Search
USPC ........................................... 514/52; 536/119
See application file for complete search history.

(56) References Cited

FOREIGN PATENT DOCUMENTS

| CA | 1202622 | * | 1/1986 | ............ | C07H 13/06 |
|---|---|---|---|---|---|
| CA | 1 202 622 | A1 | 4/1986 | | |
| CA | 1202622 | * | 4/1986 | ............ | C07H 13/06 |
| JP | 58-185599 | A | 10/1983 | | |
| JP | 59-181297 | A | 10/1984 | | |
| JP | 62-053926 | A | 3/1987 | | |
| JP | 09-104614 | A | 4/1997 | | |
| JP | 09-188603 | A | 7/1997 | | |
| JP | 11-171727 | A | 6/1999 | | |
| JP | 2005-330232 | A | 12/2005 | | |
| WO | 2007/111214 | A1 | 10/2007 | | |
| WO | 2008/093700 | A1 | 8/2008 | | |

OTHER PUBLICATIONS

Liav et al, Chemistry & Physics of Lipids, 1980, 27, 345-52.*
Numata et al, Chem. Pharm. Bull., 1985, 33, 4544-4555.*
Nishizawa et al, J. Org. Chem. Mar. 2, 2007, 72(5), 1627-1633.*
Igarashi et al, J. Nat. Prod., 2009, 72, 980-982.*
Liu et al, Ind. Eng. Chem. Res. 2006, 45, 9107-14.*
Extended European Search Report dated Jul. 10, 2012, issued by the European Patent Office in related European Patent Application No. EP-09823291.1 (13 pages).
Igarashi, Yasuhiro, et al., "Brartemicin, an Inhibitor of Tumor Cell Invasion from the Actinomycete Nonomuraea sp. (1)"; Journal of Natural Products, vol. 72, No. 5, May 22, 2009; XP55030704, ISSN: 0163-3864, DOI: 10.1021/np9000575; pp. 980-982.
Liav, A., et al., "A New Synthesis of Cord Factors and Analogs"; Chemistry and Physics of Lipids, vol. 27, No. 4, Dec. 1, 1980; XP024558582, ISSN: 0009-3084, DOI: 10.1016/0009-3084(80)90029-8; pp. 345-352.
International Search Report from PCT/JP2009/005650 dated Dec. 1, 2009 (3 pages).
Liu, Jia et al.; "Effect of Displacer Chemistry on Displacer Efficacy for a Sugar-Based Anion Exchange Displacer Library"; Department of Chemical and Biological Engineering and Department of Chemistry and Chemical Biology, Rensseloer Institute, Troy, New York; 2006 American Chemical Society; pp. 9107-9114 (8 pages).
Numata, Fumio et al.; "Lethal and Adjuvant Activities of Cord Factor (Trehalose-6,6'-dimycolate) and Synthetic Analogs in Mice"; Institute of Immunological Science, Hokkaido University, Sapporo 060, Japan; vol. 33, 1985; pp. 4544-4555 (12 pages).
Nishizawa, Mugio et al.; "Efficient Syntheses of a Series of Trehalose Dimycolae (TDM)/Trehalose Dicrynomycolate (TDCM) Analogues and Their Interleukin-6 Level Enhancement Activity in Mice Sera"; Journal of Organic Chemistry; 2007; pp. 1627-1633 (7 pages).

(Continued)

*Primary Examiner* — Ganapathy Krishnan
(74) *Attorney, Agent, or Firm* — Osha Liang LLP

(57) ABSTRACT

A trehalose compound having high immunopotentiating activity and low toxicity is represented by formula (1). (In the formula, X and X' each represents a phenyl, a naphthyl, $R_1$—$CHR_1$— (wherein $R_1$ and $R_2$ each represents a $C_7$-$C_{21}$ alkyl group or the like) or the like; and n and n' each independently represents an integer of 0-3). The compound exhibits a high activating effect on macrophages and neutrophils.

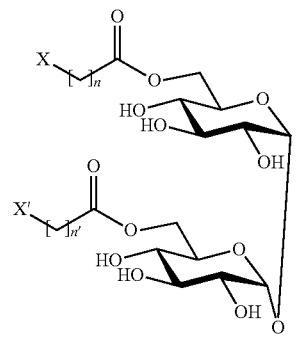

(Formula 1)

13 Claims, 14 Drawing Sheets

(56) References Cited

OTHER PUBLICATIONS

First Office Action issued Apr. 22, 2013, by the State Intellectual Property Office of the People's Republic of China, in related Chinese Patent Application No. 200980143626.5, with English translation (21 pages).

Patent Abstracts of Japan English Abstract for JP58-185599 published Oct. 29, 1983 (1 page).

Patent Abstracts of Japan English Abstract for JP62-053926 published Mar. 9, 1987 (1 page).

Extended European Search Report dated Feb. 13, 2013, from the European Patent Office in related European Patent Application No. 12190302.5-1452 (12 pages).

Durand, Elisabeth, et al., "Phase Behaviour of Cord Factor and Related Bacterial Glycolipid Toxins, A Monolayer Study"; European Journal of Biochemistry, vol. 93, No. 1; Jan. 1, 1979; XP055050840, ISSN: 0014-2956, DOI: 10.1111/j.1432-1033.1979.tb12799.x; pp. 103-112.

Johnson, David A., et al., "An Efficient Synthesis of 6,6'-DI-O-Acylated alpha, alpha-trehalose"; Journal of Carbohydrate Chemistry, vol. 17, No. 6; Jan. 1, 1998; XP009166468, ISSN: 0732-8303; pp. 969-974.

Office Action dated Feb. 12, 2014, issued by the Japan Patent Office, in related Japanese Patent Application No. 2010-535655 (5 pages).

Nishikawa, et al., "Synthesis and Antitumor Effects of 6, 6'-Di-O-acyl-a, a-trehaloses"; Nihon Kagakukai-shi, 1982; (10); pp. 1661-1666.

Garcia, Dulce M., et al., "Synthesis of Four Stereoisomers of TDCM: Cell Surface Glycolipids of Mycobacterium and Related Species"; The Chemistry of Natural Products, Symposium Papers, 1995; pp. 559-564.

Gensler, Walter J., et al., "Trehalose Covalently Conjugated to Bovine Serum Albumin"; J. Org. Chem. 1977, vol. 42, No. 1; pp. 130-135.

Nishizawa, Mugio, et al., "Effective Synthesis of Four Isomeric Trehalose Dicorynomycolates (TDCMs) and Their Immunoadjuvant Activities"; Synlett Letters, Issue 5, 1996; pp. 452-454.

* cited by examiner

☐ THP-1 (Human monocyte · macrophage cell)
▨ A549 (Human pulmonary cancer cell)
■ DLD-1 (Human colon cancer cell)

TREHALOSE COMPOUND, METHOD FOR PRODUCING SAME, AND PHARMACEUTICAL PRODUCT CONTAINING THE COMPOUND

TECHNICAL FIELD

The present invention relates to a trehalose compound, a method for producing the same, and a pharmaceutical product comprising the same.

BACKGROUND ART

Various types of infectious diseases, such as those caused by bacteria, viruses or fungi, have been known. As a therapeutic method for infectious diseases caused by bacteria, administration of antibiotics has been carried out. However, such administration of antibiotics has been problematic in terms of the emergence of microbes resistant to antibiotics. It has also caused in-hospital infection of such resistant microbes. In addition, administration of antibiotics has also been problematic in terms of opportunistic infection, which is common in immune-compromised patients who are infected with HIV, who are under treatment with anticancer agents, and who are elder people or children, etc.

Moreover, in the case of infection with enteropathogenic *Escherichia coli* such as O-157 or *Shigella dysenteriae*, verotoxin is generated in vivo, and severe symptoms such as combination with hemolytic uremic syndrome may occur particularly in the case of elder people or children with compromised immune systems. To such infectious diseases, antibiotics may be administered in some cases. However, it has been pointed out that administration of antibiotics may cause to kill bacteria, and as a result, toxin existing in the bacteria may be released to outside of the bacteria at once, so that the condition may be deteriorated. On the other hand, in the case of highly contagious infection diseases, such as O-157, which are transmissible only by ingestion of several hundreds of to several thousands of bacteria, there may be cases in which administration of antibiotics should be selected to prevent secondary infection. With regard to other therapeutic methods, since approximately 10% of all the O-157 infection cases may combine with hemolytic uremic syndrome, plasma exchange, dialysis therapy, and the like are carried out on such O-157 infection cases. These are all therapeutic methods which may impose an undue burden on patients.

Furthermore, as a method for coping with toxin generated by bacteria, symptomatic therapy is mainly carried out. Other methods include the use of a toxin adsorbent, the use of an antibody against such toxin, and the like. Such adsorption methods involving the use of activated carbon or the like may cause side effects such as constipation. Further, the use of an antibody is inconvenient in that an antibody must be developed against each type of toxin.

Thus, a method for treating infectious disease caused by such pathogenic bacteria or a method for suppressing the onset of such infectious disease has been searched for. Recently, it has been attempted to treat or prevent infectious diseases by enhancing a patient's own immune system without administering antibiotics.

Various compounds have been studied in order to find out substances for enhancing the patient's own immune system. As examples of ingredients obtained from natural products, trehalose dimycolate (TDM) and trehalose dicorynomycolate (TDCM), which are diester compounds of trehalose, have been known. TDM has been discovered as a glycolipid existing on the cell cortex of Mycobacterium tuberculosis, and it has been known to exhibit immunostimulatory activity and anticancer activity. Moreover, TDCM has been isolated, as a homolog having fewer carbon atoms than those of TDM, from related *Corynebacterium* spp. It has been revealed that both TDCM and a stereoisomer thereof exhibit immunostimulatory activity and anticancer activity.

However, TDM and TDCM are highly toxic, and thus, they cannot be used as pharmaceutical products. Accordingly, in order to use TDM and TDCM as pharmaceutical products, it has been necessary to synthesize compounds with reduced toxicity, while maintaining or enhancing their activity.

Hence, a trehalose 6,6'-diester compound, which is a trehalose fatty acid ester composition, has been synthesized as a TDM derivative. Various tests, such as a toxicity test and a macrophage activating test, have been performed on the trehalose 6,6'-diester compound (see Non Patent Literature 1). In this publication, the presence or absence of a β-hydroxyl group, compounds having 30, 32 or 48 carbon atoms as a length of the alkyl portion of a lipid, compounds in which the ester bond between a sugar and a lipid has been replaced by an amide bond, etc. have been studied. In terms of toxicity, this publication describes that an ester bond and a long chain fatty acid greatly contribute to toxicity. This publication describes a compound having 30 carbon atoms as a length of a side chain fatty acid portion. However, in order to obtain a compound having high activity and low toxicity, the binding manner of a sugar and a side chain, the presence or absence of a substituent for a side chain fatty acid, the length of an alkyl group constituting such a side chain fatty acid, and the like have not been comprehensively studied and have not been optimized. Tests have been just sporadically carried out on several compounds as described above. Even with regard to immunostimulatory action, the contents thereof have not been studied in detail.

On the other hand, with regard to a TDM derivative, the present inventors have synthesized a TDM derivative having an ester bond or an amide bond, in which the β-hydroxyl group has been replaced by a hydrogen atom or a methoxy group (see Patent Literature 1). However, the derivative described in this publication has a comparatively short alkyl portion of fatty acid (approximately 7 carbon atoms). With regard to its activity, only activity as an adenosine A3 receptor antagonist was measured.

The present inventors have succeeded in substituting the hydroxyl group of TDCM with a hydrogen atom, so that it could not be an asymmetric carbon atom, as well as in synthesizing an amide derivative of TDCM, in which the ester bond has been replaced by an amide bond. The inventors have then confirmed that these amide derivatives have immunostimulatory action (see Patent Literature 2). However, thereafter, it has been found that these amide derivatives have action to induce cancer, and as a result, it could not help giving up the use of the amide derivatives as pharmaceutical compounds.

Therefore, a sufficiently effective and highly safe method for treating various symptoms caused by pathogenic bacteria or suppressing the onset of such symptoms, using such a TDM or TDCM derivative, has not yet been established. Thus, it has been desired to develop an effective and safe method for treating the symptoms caused by pathogenic bacteria or suppressing the onset of the symptoms.

CITATION LIST

Patent Literature

[Patent Literature 1] WO2007/111214
[Patent Literature 2] WO2008/093700

Non Patent Literature

[Non Patent Literature 1] Numata et al., Chem. Pharm. Bull. (1985), 33(10), 4544-4555

SUMMARY OF INVENTION

Technical Problem

When TDM and TDCM derivatives are synthesized, since TDM and TDCM themselves are highly toxic, it is necessary to synthesize compounds having activity and also having low toxicity. As prior art techniques, several TDM and TDCM modified bodies have been known. However, TDM and TDCM are glycolipids, their sugar chain contains many hydroxyl groups and has high polarity, and it is difficult to synthesize them. Thus, structure activity correlation, such as the relationship between type of structure and the type of activity, has not yet been clarified.

Under the aforementioned circumstances, it is an object of the present invention to produce a large number of TDM and TDCM derivatives and to provide a compound having high activity and low toxicity and a pharmaceutical product comprising the compound.

Moreover, in prior art techniques, the use of antibiotics against pathogenic bacteria has been directed towards inhibition of the growth of *Escherichia coli*, the killing of *Escherichia coli*, and the like, which resulted in prevention of the release of toxin from the *Escherichia coli*. Thus, antibiotics were not able to detoxify the generated toxin itself. In contrast, it is an object of the present invention to provide a pharmaceutical product capable of reducing the toxicity of a toxin, even in a case in which bacteria have grown to such an extent that they generate the toxin.

Solution to Problem

The present inventors have found that a trehalose diester compound represented by formula (1) exhibits excellent antibacterial activity on infectious diseases caused by pathogenic bacteria and has low toxicity. In addition, the inventors have also found that, among the trehalose diester compounds represented by the formula (1), a compound, in which X represents $R_1$—$CHR_2$—, X' represents $R_1'$—$CHR_2'$—, and as a branched form of a lipid portion thereof, particularly n and n' each represent 0 (hereinafter referred to as an α-branched compound), and particularly, n and n' each represent 1 (hereinafter referred to as a β-branched compound), is particularly excellent. Moreover, the inventors have also found that, among the trehalose diester compounds represented by the formula (1), a compound, in which an alkyl chain portion represented by $R_1$, $R_2$, $R_1'$ or $R_2'$ in the formula (1) has a specific length (the number of carbon atoms is 10, 14 or the like), tends to have maximum activity. Furthermore, the aforementioned publications and the like do not describe that the trehalose diester compound is useful as an antibacterial agent, even when toxin generated by bacteria is administered. In contrast, the present inventors have found in mouse in-vivo tests that the present trehalose diester compound is useful, when not only bacteria, but also toxin generated by such bacteria is administered to mice.

The present invention provides a compound represented by the following formula (1):

[Formula 1]

wherein X represents phenyl, naphthyl, or a group represented by $R_1$—$CHR_2$—, and X' represents phenyl, naphthyl, or a group represented by $R_1'$—$CHR_2'$—, wherein $R_1$, $R_1'$, $R_2$ and $R_2'$ independently represent a hydrogen atom or a $C_1$-$C_{21}$ alkoxy group, and with regard to $R_1$, $R_1'$, $R_2$ and $R_2'$, a hydrogen atom in each alkyl group may be replaced by a hydroxyl group or an alkoxy group, all or some of alkyl groups may form a 4- to 8-membered ring, and $R_1$ and $R_2$, and $R_1'$ and $R_2'$ may bind to each other to form a 4- to 8-membered ring, and wherein n and n' independently represent an integer of 0 to 3, with the proviso that that the compound is not the following compounds:

(1) a compound, in which X represents $R_1$—$CHR_2$—, X' represents $R_1'$—$CHR_2'$—, $R_1$, $R_1'$, $R_2$ and $R_2'$ independently represent a hydrogen atom or an unsubstituted linear $C_1$-$C_6$ alkyl group, and n and n' represent 0; and (2) a compound, in which X represents $R_1$—$CHR_2$—, X' represents $R_1'$—$CHR_2'$—, $R_1$, $R_1'$, $R_2$ and $R_2'$ represent a $C_{14}$ linear alkyl group, and n and n' represent 0.

In addition, the present invention provides a pharmaceutical composition comprising the compound represented by the formula (1) and a pharmaceutically acceptable carrier.

Moreover, the present invention provides the pharmaceutical composition comprising the compound represented by the formula (1) and a pharmaceutically acceptable carrier, wherein the pharmaceutical composition is used as an immunostimulator, a macrophage activator, a neutrophil activator, an agent for activating the phagocytosis of phagocytic cells, an anti-bacterial infection agent, or a bacterial toxin neutralizer.

Furthermore, the present invention provides use of the compound represented by the formula (1) in the manufacture of a pharmaceutical composition for use as an immunostimulator, a macrophage activator, a neutrophil activator, an agent for activating the phagocytosis of phagocytic cells, an antibacterial infection agent, or a bacterial toxin neutralizer.

Further, the present invention provides a method for preventing or treating the infectious disease in a mammal including a human, comprising administering a therapeutically effective amount of the compound represented by the formula (1) to the mammal.

Still further, the present invention provides a bacterial toxin neutralizer, comprising a compound represented by the following formula (2):

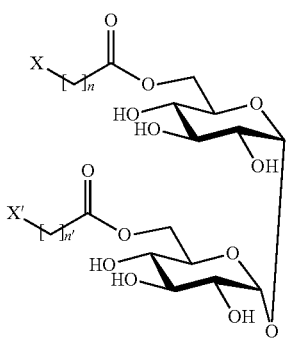

[Formula 2]

wherein X represents phenyl, naphthyl, or a group represented by $R_1$—$CHR_2$—, and X' represents phenyl, naphthyl, or a group represented by $R_1'$—$CHR_2'$—, wherein $R_1$, $R_1'$, $R_2$ and $R_2'$ independently represent a hydrogen atom or a $C_1$-$C_{21}$ alkoxy group, and with regard to $R_1$, $R_1'$, $R_2$ and $R_2'$, a hydrogen atom in each alkyl group may be replaced by a hydroxyl group or an alkoxy group, or all or some of alkyl groups may form a 4- to 8-membered ring, or $R_1$ and $R_2$, and $R_1'$ and $R_2'$ may bind to each other to form a 4- to 8-membered ring, and wherein n and n' independently represent an integer of 0 to 3.

Advantageous Effects of Invention

Since the trehalose compound of the present invention has high immunostimulatory activity and also has low toxicity, it is useful for providing an excellent pharmaceutical product, which highly acts on infectious diseases caused by pathogenic bacteria.

The trehalose compound of the present invention has action to activate cellular immunity. The present trehalose compound activates neutrophils or macrophages, so as to enhance their phagocytosis, so as to exhibit antibacterial action. Specifically, according to the compound of the present invention, since bacteria themselves are ingested by neutrophils or macrophages, the amount of toxin released to outside of the bacteria is small. As a result, the present invention is able to provide a low-risk pharmaceutical product, which may not cause the release of toxin due to destruction of *Escherichia coli* upon administration of antibiotics.

Moreover, the trehalose compound of the present invention exhibits toxicity-reducing action even on toxin itself. Thus, the present invention is able to provide a pharmaceutical product, which is effective even in a case in which the degree of infection in an infectious disease caused by *Escherichia coli* has progressed and such *Escherichia coli* has grown and has released toxin to outside of the bacteria.

Furthermore, as a result of activation of neutrophils or macrophages by administration of the trehalose compound of the present invention, they can ingest multi-drug-resistant bacteria generated as a result of administration of antibiotics, as well as non-resistant bacteria. Accordingly, the present invention is able to provide a pharmaceutical product having therapeutic effects also on infectious diseases caused by multi-drug-resistant bacteria.

Further, the trehalose compound of the present invention activates cellular immunity, but it does not cause excessive immune response. Accordingly, the present invention is able to provide a pharmaceutical product, which hardly causes a risk of such excessive immune response that an antibody against an antibody administered as a pharmaceutical product may be generated.

Still further, the trehalose compound of the present invention includes compounds that do not contain asymmetric carbon atoms. That is to say, the trehalose compound according to the present invention can be efficiently synthesized in a large volume by a method for producing the trehalose compound of the present invention, without involving asymmetric synthesis.

DESCRIPTION OF EMBODIMENTS

Figure 1:
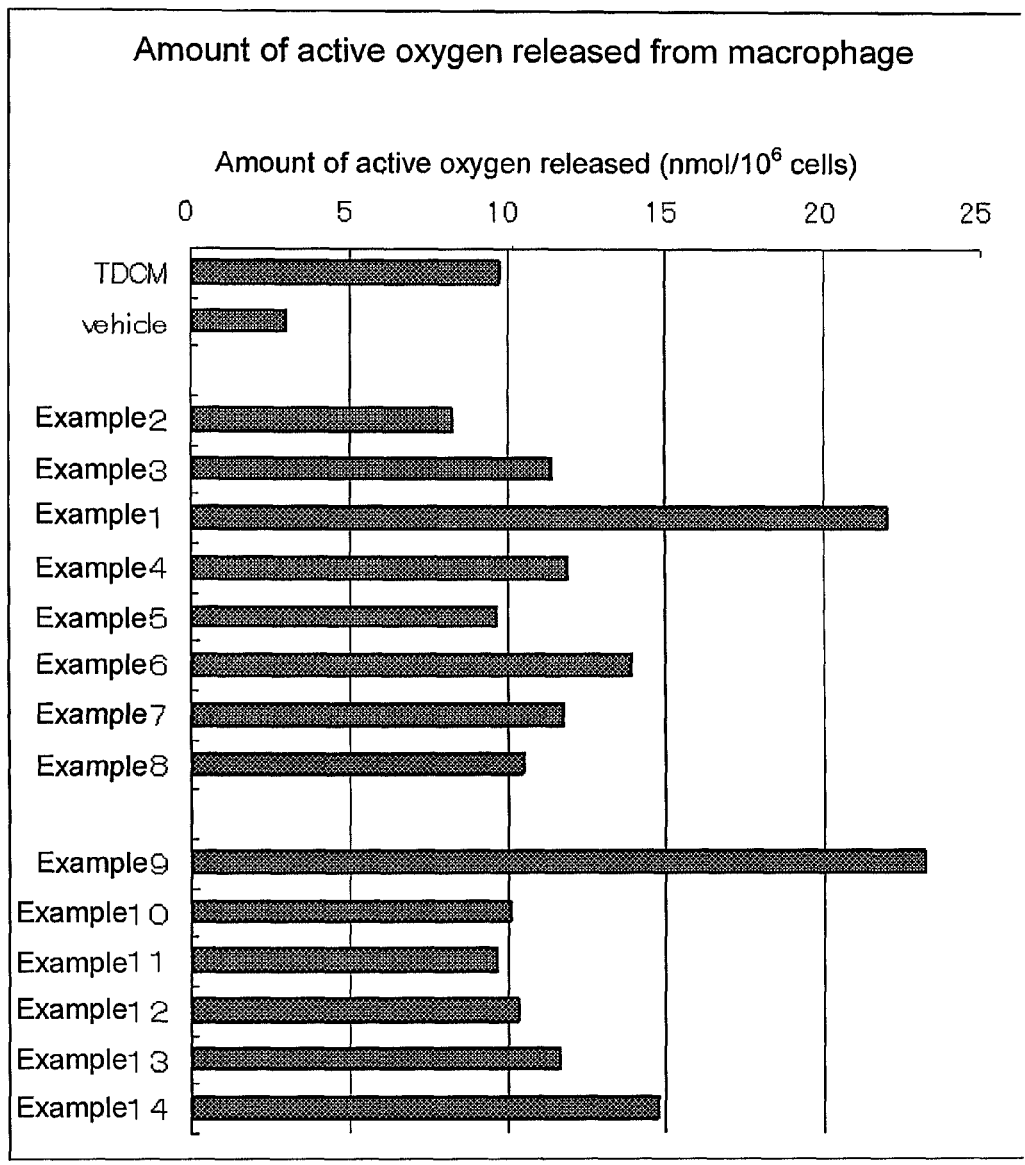
FIG. 1 shows the amount of active oxygen released from mouse intraperitoneal macrophages in a case in which TDCM, a vehicle or the test compound of the present invention was allowed to act on the mouse intraperitoneal macrophages.

Hereinafter, preferred embodiments of the present invention will be described. The compound represented by the formula (1) may be present in the form of a pharmaceutically acceptable salt or solvate thereof.

The term "$C_1$-$C_{21}$ alkyl group" is used in the present specification to include an alicyclic hydrocarbon group in which all or some of aliphatic hydrocarbon groups form a 4- to 8-membered ring, as well as a linear or branched aliphatic hydrocarbon group containing 1 to 21 carbon atoms. In a preferred aspect, the "$C_1$-$C_{21}$ alkyl group" of the compound represented by the formula (1) of the present invention is a linear aliphatic hydrocarbon group. Examples of the "$C_1$-$C_{21}$ alkyl group," which is a linear aliphatic hydrocarbon group, include a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, and an n-henicosyl group. Examples of an alicyclic hydrocarbon group in which all of aliphatic hydrocarbon groups form a ring include a cyclobutyl group, a cyclopentyl group, a cyclohexyl group, a cycloheptyl group, and a cyclooctyl group. Examples of an alicyclic hydrocarbon group in which some of aliphatic hydrocarbon groups form a ring include a cyclohexyl-n-octyl group, a cyclohexyl-n-nonyl group, and a cycloheptyl-n-octyl group. $R_1$, $R_1'$, $R_2$ or $R_2'$ is preferably a linear alkyl group, and more preferably a linear alkyl group containing 10 to 16 carbon atoms. It is particularly preferably an n-decyl group which is a linear alkyl group containing 10 carbon atoms, when n is 0, or it is particularly preferably an n-nonyl group which is a linear alkyl group containing 9 carbon atoms, an n-tridecyl group which is a linear alkyl group containing 13 carbon atoms, or an n-tetradecyl group which a linear alkyl group containing 14 carbon atoms, when n is 1. It is most preferably an n-decyl group.

With regard to $R_1$, $R_1'$, $R_2$ and $R_2'$, the hydrogen atom in each alkyl group may be replaced by a hydroxyl group or an alkoxy group. The term "alkoxy group" is used herein to mean a substituent group having a structure in which a linear or branched aliphatic hydrocarbon group containing 1 to 21 carbon atoms binds to an oxygen atom. Examples of such an alkoxy group include a methoxy group, an ethoxy group, a propoxy group, a butoxy group, a pentyloxy group, a hexyloxy group, and a heptyloxy group. It is preferably a linear alkoxy group. Examples of the alkyl group substituted with such an alkoxy group include a methoxy dodecyl group, an ethoxy undecyl group, a propoxy decyl group, a pentyloxy nonyl group, a hexyloxy octyl group, a hexyloxy heptyl group, and a pentyloxy octyl group. When the hydrogen atom in each alkyl group is replaced by a hydroxyl group or an alkoxy group, the substitution position may be anywhere in each alkyl group. It is preferably a compound in which a hydrogen atom binding to the terminal carbon atom of the alkyl group is replaced by a hydroxyl group or an alkoxy group. When such an alkoxy group binds to the terminal carbon atom of the alkyl group, it adopts a linear ether structure to which a hydrocarbon group binds via an oxygen atom. With regard to the sum of intervening oxygen atoms and carbon atoms constituting a hydrocarbon group, as with the aforementioned length of the alkyl group of a hydrocarbon group, the number of carbon and oxygen atoms constituting an alkoxyalkyl group is preferably 2 to 21, and more preferably 10 to 16 when n is 0, and 9 to 15 when n is 1.

$R_1$ and $R_2$, and $R_1'$ and $R_2'$ may bind to each other to form a 4- to 8-membered ring. When X is $R_1$—$CHR_2$—, the carbon atom to which $R_1$ and $R_2$ bind, and such $R_1$ and $R_2$ all become constituent atoms of the 4- to 8-membered ring. In addition, alkyl groups constituting $R_1$ and $R_2$ may be branched alkyl groups, and in such a case, some of the branched alkyl groups may constitute the 4- to 8-membered ring, so that it may adopt such a structure as cycloalkyl substituted with an alkyl group. Moreover, the cases in which a ring is formed include the cases of being replaced by the aforementioned substituents. The same applies not only to X but also to X'. Examples of such a 4- to 8-membered ring include a cyclobutyl group, a cyclopentyl group, a cyclohexyl group, a cycloheptyl group, and a cyclooctyl group. From the viewpoint of the structural stability of compound, the 4- to 8-membered ring is preferably a cyclohexyl group or a cycloheptyl group.

$R_1$ and $R_2$, and $R_1'$ and $R_2'$ may be identical to or different from each other. From the viewpoint of synthetic efficiency, preferably, $R_1$ is identical to $R_1'$, and $R_2$ is identical to $R_2'$.

Moreover, with regard to the relationship between $R_1$ and $R_2$, $R_1$ and $R_2$ may be identical to or different from each other. In one of the preferred aspects, it is a compound, in which the number of carbon atoms of $R_1$ is identical to the number of carbon atoms of $R_2$, or the number of carbon atoms of $R_1$ is larger (1 or 2 carbon atoms) or smaller (1 or 2 carbon atoms) than the number of carbon atoms of $R_2$. For example, it is a compound, in which $R_1$ has 14 carbon atoms and $R_2$ has 16 carbon atoms. Other than the above described compound, preferred examples also include a compound, in which $R_1$ is a short chain alkyl group containing 1 to 5 carbon atoms and $R_2$ is a long chain alkyl group containing 10 to 16 carbon atoms, and a compound, in which $R_1$ is a long chain alkyl group containing 10 to 16 carbon atoms and $R_2$ is a short chain alkyl group containing 1 to 5 carbon atoms. The relationship between $R_1'$ and $R_2'$ is the same as the aforementioned relationship between $R_1$ and $R_2$. Thus, it is possible to read $R_1$ as $R_1'$, and $R_2$ as $R_2'$, in the aforementioned relationship between $R_1$ and $R_2$.

n and n' may be identical to or different from each other. From the viewpoint of synthetic efficiency, n is preferably identical to n'. In addition, from the viewpoint of activity, a compound in which n or n' is 0, and a compound in which n or n' is 1, are preferable.

Trehalose has three isomers, namely, an $\alpha,\alpha'$ form, an $\alpha,\beta'$ form, and a $\beta,\beta'$ form. Of these, an $\alpha,\alpha'$ form is preferable as the trehalose compound of the present invention.

The compound represented by the formula (1) and a salt thereof may be present in the form of a solvate. Such a solvate is included in the scope of the present invention. Moreover, radiolabeled compounds of the aforementioned compound represented by the formula (1), which are useful for biological studies, are also included in the scope of the present invention.

The compound of the present invention is preferably the aforementioned compound represented by the formula (1). Each substituent in the formula has the following characteristics. The following characteristics can be independently selected, singly or in combination, unless they include contradictions.

(A) X is a group represented by $R_1$—$CHR_2$—.
(B) X' is a group represented by $R_1'$—$CHR_2'$—.
(C) $R_1$ and $R_1'$ independently represent an unsubstituted $C_1$-$C_{21}$ alkyl group.
(D) $R_2$ and $R_2'$ independently represent a hydrogen atom or an unsubstituted $C_1$-$C_{21}$ alkyl group.
(E) $R_1$ and $R_1'$ independently represent a linear $C_1$-$C_{21}$ alkyl group.
(F) $R_2$ and $R_2'$ independently represent a hydrogen atom or a linear $C_1$-$C_{21}$ alkyl group.
(G) $R_1$ and $R_1'$ independently represent an unsubstituted and linear $C_1$-$C_{21}$ alkyl group.
(H) $R_2$ and $R_2'$ independently represent a hydrogen atom, or an unsubstituted and linear $C_1$-$C_{21}$ alkyl group.
(I) $R_1$ and $R_1'$ independently represent an unsubstituted and linear $C_7$-$C_{21}$ alkyl group.
(J) $R_2$ and $R_2'$ independently represent an unsubstituted and linear $C_7$-$C_{21}$ alkyl group.
(K) $R_1$ and $R_1'$ are identical to each other, and represent an unsubstituted $C_1$-$C_{21}$ alkyl group.
(L) $R_2$ and $R_2'$ are identical to each other, and represent a hydrogen atom or an unsubstituted $C_1$-$C_{21}$ alkyl group.
(M) $R_1$ and $R_1'$ are identical to each other, and represent a linear $C_1$-$C_{21}$ alkyl group.
(N) $R_2$ and $R_2'$ are identical to each other, and represent a hydrogen atom or a linear $C_1$-$C_{21}$ alkyl group.
(O) $R_1$ and $R_1'$ are identical to each other, and represent an unsubstituted and linear $C_1$-$C_{21}$ alkyl group.
(P) $R_2$ and $R_2'$ are identical to each other, and represent a hydrogen atom, or an unsubstituted and linear $C_1$-$C_{21}$ alkyl group.
(Q) $R_1$ and $R_1'$ are identical to each other, and represent an unsubstituted and linear $C_7$-$C_{21}$ alkyl group.
(R) $R_2$ and $R_2'$ are identical to each other, and represent an unsubstituted and linear $C_7$-$C_{21}$ alkyl group.
(S) n and n' independently represent 0 or 1.
(T) n and n' are 0.
(U) n and n' are 1.

The compound of the present invention is preferably the compound represented by the formula (1), or a pharmaceutically acceptable salt or solvate thereof, which has the following structures.

(V) X is a group represented by $R_1$—$CHR_2$—; X' is a group represented by $R_1'$—$CHR_2'$—, wherein $R_1$, $R_1'$, $R_2$ and $R_2'$ independently represent a hydrogen atom or a $C_1$-$C_{21}$ alkyl group, and with regard to such $R_1$, $R_1'$, $R_2$ and $R_2'$, the hydrogen atom in each alkyl group may be replaced by a hydroxyl group or an alkoxy group, all or some of alkyl groups may form a 4- to 8-membered ring, and $R_1$ and $R_2$, and $R_1'$ and $R_2'$ may bind to each other to form a 4- to 8-membered ring; and n and n' independently represent an integer of 0 to 3.

(W) X is a group represented by $R_1$—$CHR_2$—; X' is a group represented by $R_1'$—$CHR_2'$—, wherein $R_1$, $R_1'$, $R_2$ and $R_2'$ independently represent a linear $C_7$-$C_{21}$ alkyl group, and with regard to such $R_1$, $R_1'$, $R_2$ and $R_2'$, the hydrogen atom in each alkyl group may be replaced by a hydroxyl group or an alkoxy group, and all or some of alkyl groups may form a 4- to 8-membered ring; and n and n' independently represent an integer of 0 or 1.

(X) X is a group represented by $R_1$—$CHR_2$—; X' is a group represented by $R_1'$—$CHR_2'$—; wherein $R_1$, $R_1'$, $R_2$ and $R_2'$ independently represent a $C_8$-$C_{16}$ alkyl group, and with regard to such $R_1$, $R_1'$, $R_2$ and $R_2'$, the hydrogen atom in each alkyl group may be replaced by a hydroxyl group or an alkoxy group, and all or some of alkyl groups may form a 4- to 8-membered ring; and n and n' independently represent 0.

(Y) X is a group represented by $R_1$—$CHR_2$—; X' is a group represented by $R_1'$—$CHR_2'$—, wherein $R_1$, $R_1'$, $R_2$ and $R_2'$ independently represent a $C_8$-$C_{14}$ alkyl group, and with regard to such $R_1$, $R_1'$, $R_2$ and $R_2'$, the hydrogen atom in each alkyl group may be replaced by a hydroxyl group or an alkoxy group, and all or some of alkyl groups may form a 4- to 8-membered ring; and n and n' independently represent 1.

(Z) X is a group represented by $R_1$—$CHR_2$—; X' is a group represented by $R_1'$—$CHR_2'$—; wherein $R_1$ and $R_1'$ are identical to each other and represent a hydrogen atom or a $C_1$-$C_{21}$ alkyl group, and with regard to such $R_1$ and $R_1'$, the hydrogen atom in each alkyl group may be replaced by a hydroxyl group or an alkoxy group, and all or some of alkyl groups may form a 4- to 8-membered ring; $R_2$ and $R_2'$ are identical to each other and represent a hydrogen atom or a $C_1$-$C_{21}$ alkyl group, and with regard to such $R_1$ and $R_2'$, the hydrogen atom in each alkyl group may be replaced by a hydroxyl group or an alkoxy group, and all or some of alkyl groups may form a 4- to 8-membered ring; $R_1$ and $R_2$, and $R_1'$ and $R_2'$ may bind to each other to form a 4- to 8-membered ring; and n and n' are identical to each other and represent an integer of 0 to 3.

(AA) X is a group represented by $R_1$—$CHR_2$—; X' is a group represented by $R_1'$—$CHR_2'$—; wherein $R_1$ and $R_1'$ are identical to each other and represent a $C_1$-$C_{21}$ alkyl group, and the hydrogen atom in each alkyl group may be replaced by a hydroxyl group or an alkoxy group; $R_2$ and $R_2'$ are identical to each other and represent a $C_7$-$C_{21}$ alkyl group, and the hydrogen atom in each alkyl group may be replaced by a hydroxyl group or an alkoxy group; and n and n' are identical to each other and represent 0 or 1.

(BB) X is a group represented by $R_1$—$CHR_2$—; X' is a group represented by $R_1'$—$CHR_2'$—; wherein $R_1$ and $R_1'$ are identical to each other and represent a $C_7$-$C_{21}$ alkyl group, and the hydrogen atom in each alkyl group may be replaced by a hydroxyl group or an alkoxy group; $R_2$ and $R_2'$ are identical to each other and represent a hydrogen atom or a $C_1$-$C_{21}$ alkyl group, and the hydrogen atom in each alkyl group may be replaced by a hydroxyl group or an alkoxy group; and n and n' are identical to each other and represent 0 or 1.

(CC) X is a group represented by $R_1$—$CHR_2$—; X' is a group represented by $R_1'$—$CHR_2'$—; wherein $R_1$ and $R_1'$ are identical to each other and represent a linear $C_7$-$C_{21}$ alkyl group, and the hydrogen atom in each alkyl group may be replaced by a hydroxyl group or an alkoxy group; $R_2$ and $R_2'$ are identical to each other and represent a linear $C_7$-$C_{21}$ alkyl group, and the hydrogen atom in each alkyl group may be replaced by a hydroxyl group or an alkoxy group; and n and n' are identical to each other and represent 0 or 1.

(DD) X is a group represented by $R_1$—$CHR_2$—; X' is a group represented by $R_1'$—$CHR_2'$—; wherein $R_1$ and $R_1'$ are identical to each other and represent an unsubstituted and linear $C_1$-$C_{21}$ alkyl group; $R_2$ and $R_2'$ are identical to each other, and represent a hydrogen atom, or an unsubstituted and linear $C_7$-$C_{21}$ alkyl group; and n and n' are identical to each other and represent 0 or 1.

(EE) X is a group represented by $R_1$—$CHR_2$—; X' is a group represented by $R_1'$—$CHR_2'$—; wherein $R_1$ and $R_1'$ are identical to each other and represent an unsubstituted and linear $C_7$-$C_{21}$ alkyl group; $R_2$ and $R_2'$ are identical to each other, and represent a hydrogen atom, or an unsubstituted and linear $C_1$-$C_{21}$ alkyl group; and n and n' are identical to each other and represent 0 or 1.

(FF) X is a group represented by $R_1$—$CHR_2$—; X' is a group represented by $R_1'$—$CHR_2'$—; wherein $R_1$ and $R_1'$ are identical to each other and represent an unsubstituted and linear $C_7$-$C_{21}$ alkyl group; $R_2$ and $R_2'$ are identical to each other and represent an unsubstituted and linear $C_7$-$C_{21}$ alkyl group; and n and n' are identical to each other and represent 0 or 1.

(GG) X is a group represented by $R_1$—$CHR_2$—; X' is a group represented by $R_1'$—$CHR_2'$—; wherein $R_1$ and $R_1'$ are identical to each other and represent an unsubstituted and linear $C_8$-$C_{16}$ alkyl group; $R_2$ and $R_2'$ are identical to each other and represent an unsubstituted and linear $C_8$-$C_{16}$ alkyl group; and n and n' are identical to each other and represent 0 or 1.

(HH) X is a group represented by $R_1$—$CHR_2$—; X' is a group represented by $R_1'$—$CHR_2'$—; wherein $R_1$ and $R_1'$ are identical to each other and represent an unsubstituted and linear $C_8$-$C_{16}$ alkyl group; $R_2$ and $R_2'$ are identical to each other and represent an unsubstituted and linear $C_8$-$C_{16}$ alkyl group; and n and n' are identical to each other and represent 0.

(II) X is a group represented by $R_1$—$CHR_2$—; X' is a group represented by $R_1'$—$CHR_2'$—; wherein $R_1$ and $R_1'$ are identical to each other and represent an unsubstituted and linear $C_9$-$C_{14}$ alkyl group; $R_2$ and $R_2'$ are identical to each other and represent an unsubstituted and linear $C_9$-$C_{14}$ alkyl group; and n and n' are identical to each other and represent 1.

(JJ) X is a group represented by $R_1$—$CHR_2$—; X' is a group represented by $R_1'$—$CHR_2'$—; wherein $R_1$, $R_1'$, $R_2$ and $R_2'$ are identical to one another and represent an unsubstituted and linear $C_{10}$ alkyl group; and n and n' represent 0.

(KK) X is a group represented by $R_1$—$CHR_2$—; X' is a group represented by $R_1'$—$CHR_2'$—; wherein $R_1$, $R_1'$, $R_2$ and $R_2'$ are identical to one another and represent an unsubstituted and linear $C_9$, $C_{13}$, or $C_{14}$ alkyl group; and n and n' represent 1.

Specific examples of the trehalose compound of the present invention include the following compounds:
6,6'-bis-O-(2-octyldecanoyl)-α,α'-trehalose,
6,6'-bis-O-(2-nonylundecanoyl)-α,α'-trehalose,
6,6'-bis-O-(2-decyldodecanoyl)-α,α'-trehalose,
6,6'-bis-O-(2-undecyltridecanoyl)-α,α'-trehalose,
6,6'-bis-O-(2-dodecyltetradecanoyl)-α,α'-trehalose,
6,6'-bis-O-(2-tridecylpentadecanoyl)-α,α'-trehalose,
6,6'-bis-O-(2-pentadecylheptadecanoyl)-α,α'-trehalose,
6,6'-bis-O-(2-hexadecyloctadecanoyl)-α,α'-trehalose,
6,6'-bis-O-(3-nonyldodecanoyl)-α,α'-trehalose,
6,6'-bis-O-(3-decyltridecanoyl)-α,α'-trehalose,
6,6'-bis-O-(3-undecyltetradecanoyl)-α,α'-trehalose,
6,6'-bis-O-(3-dodecylpentadecanoyl)-α,α'-trehalose,
6,6'-bis-O-(3-tridecylhexadecanoyl)-α,α'-trehalose,
6,6'-bis-O-(3-tetradecylheptadecanoyl)-α,α'-trehalose,
6,6'-bis-O-(benzoyl)-α,α'-trehalose,
6,6'-bis-O-(2-naphthylcarbonyl)-α,α'-trehalose,
6,6'-bis-O-(cyclohexanecarbonyl)-α,α'-trehalose,
6,6'-bis-O-(cycloheptanecarbonyl)-α,α'-trehalose,
6,6'-bis-O-(2-tetradecyloctadecanoyl)-α,α'-trehalose,
6,6'-bis-O-(14-methoxy-2-(12-methoxydodecyl)-tetradecanoyl)-α,α'-trehalose, and
6,6'-bis-O-(15-hydroxy-2-(13-hydroxytridecyl)-pentadecanoyl)-α,α'-trehalose.

Preferred examples of the trehalose compound of the present invention include the following compounds:
6,6'-bis-O-(2-octyldecanoyl)-α,α'-trehalose,
6,6'-bis-O-(2-nonylundecanoyl)-α,α'-trehalose,
6,6'-bis-O-(2-decyldodecanoyl)-α,α'-trehalose,
6,6'-bis-O-(2-undecyltridecanoyl)-α,α'-trehalose,
6,6'-bis-O-(2-dodecyltetradecanoyl)-α,α'-trehalose,
6,6'-bis-O-(2-tridecylpentadecanoyl)-α,α'-trehalose,
6,6'-bis-O-(2-pentadecylheptadecanoyl)-α,α'-trehalose, and
6,6'-bis-O-(2-hexadecyloctadecanoyl)-α,α'-trehalose.

Other preferred examples of the trehalose compound of the present invention include the following compounds:
6,6'-bis-O-(3-nonyldodecanoyl)-α,α'-trehalose,
6,6'-bis-O-(3-decyltridecanoyl)-α,α'-trehalose,
6,6'-bis-O-(3-undecyltetradecanoyl)-α,α'-trehalose,
6,6'-bis-O-(3-dodecylpentadecanoyl)-α,α'-trehalose,
6,6'-bis-O-(3-tridecylhexadecanoyl)-α,α'-trehalose, and
6,6'-bis-O-(3-tetradecylheptadecanoyl)-α,α'-trehalose.

More preferred examples of the trehalose compound of the present invention include the following compounds:
6,6'-bis-O-(2-decyldodecanoyl)-α,α'-trehalose,
6,6'-bis-O-(3-nonyldodecanoyl)-α,α'-trehalose,
6,6'-bis-O-(3-tridecylhexadecanoyl)-α,α'-trehalose, and
6,6'-bis-O-(3-tetradecylheptadecanoyl)-α,α'-trehalose.

A preferred example of the bacterial toxin neutralizer of the present invention is a bacterial toxin neutralizer comprising any one of the following compounds:
6,6'-bis-O-(2-decyldodecanoyl)-α,α'-trehalose,
6,6'-bis-O-(2-tetradecyldodecanoyl)-α,α'-trehalose,
6,6'-bis-O-(3-nonyldodecanoyl)-α,α'-trehalose,
6,6'-bis-O-(3-tridecylhexadecanoyl)-α,α'-trehalose, and
6,6'-bis-O-(3-tetradecylheptadecanoyl)-α,α'-trehalose.

The pharmaceutical composition and immunostimulator of the present invention, etc. are characterized in that they comprise the above described trehalose compound.

The trehalose compound of the present invention is used as an immunostimulator having high action to activate macrophages or neutrophils. Accordingly, the trehalose compound of the present invention is useful as an agent for preventing or treating diseases associated with a biological defense mechanism due to immune system, including infectious diseases such as bacterial infection, viral infection and fungus infection, opportunistic infectious disease, and multi-drug-resistant infectious disease.

<Production Method>

The compound represented by the formula (1) of the present invention can be synthesized by the following two steps (a) and (b):

(a) a step of allowing carbonyl compounds represented by formula (4) and formula (6) to simultaneously or successively act on a trehalose compound represented by formula (3), so as to carry out an esterification reaction; and (b) a step of deprotecting a protecting group for the hydroxyl group of a trehalose compound represented by formula (5) which is obtained in the above described step (a).

With regard to the expression "allowing carbonyl compounds represented by formula (4) and formula (6) to simultaneously or successively act on . . . " in the step (a), the carbonyl compounds represented by the formula (4) and the formula (6) may be successively acted on the trehalose compound, as shown in Synthetic Scheme 1 below. Otherwise, as shown in Synthetic Scheme 2 below, the carbonyl compounds represented by the formula (4) and the formula (6) may be simultaneously acted on the trehalose compound. Further, when the carbonyl compounds represented by the formula (4) and the formula (6) are identical to each other, these compounds may be used as a carbonyl compound represented by the formula (4), and they may be acted on the trehalose compound simultaneously, namely, at a single reaction stage, as shown in Synthetic Scheme 3 below. It is to be noted that a compound represented by formula (2) may also be synthesized as in the case of the compound represented by the formula (1).

The compound represented by the formula (1) of the present invention can be produced by the method shown in the following Synthetic Scheme 1.

<Synthetic Scheme 1>

[Formula 3]

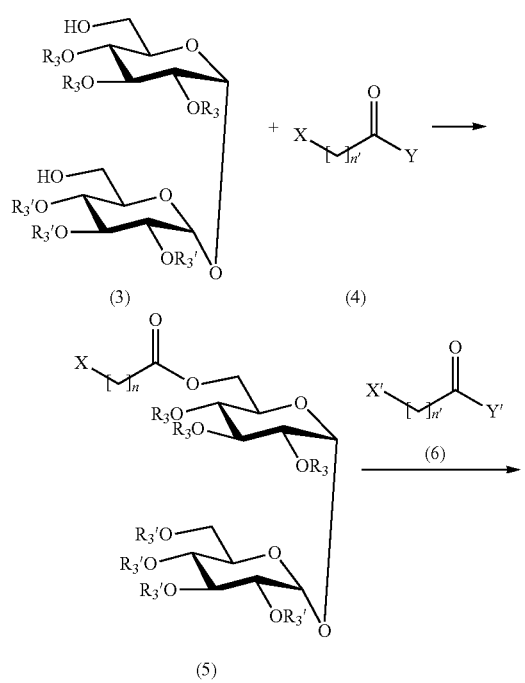

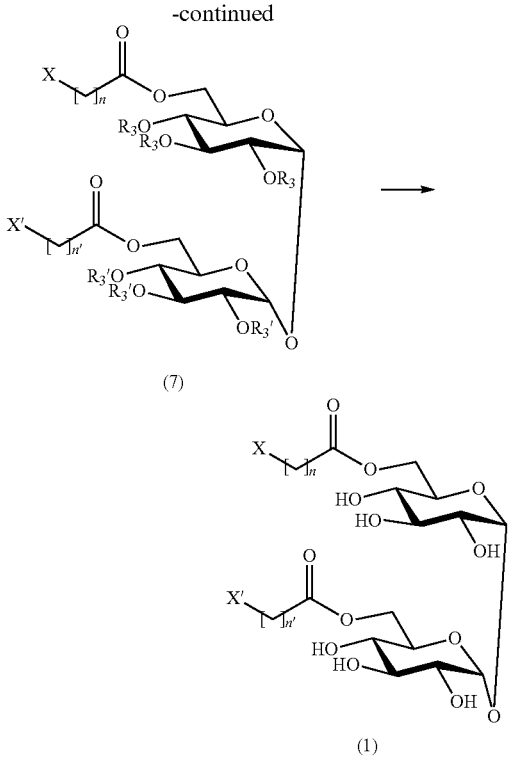

In the above synthetic scheme, $R_1$, $R_1'$, $R_2$, $R_2'$, n and n' have the same definitions as those described above. $R_3$ and $R_3'$ each represent a protecting group for the hydroxyl group of sugar. Y and Y' independently represent a hydroxyl group or a halogen atom. In the above scheme, the trehalose compound represented by the formula (3) has an $\alpha,\alpha'$ form. However, an $\alpha,\beta'$ form and a $\beta,\beta'$ form can also be synthesized in the same manner as that described above. In the present invention, however, an $\alpha,\alpha'$ form is preferable.

Herein, as $R_3$ and $R_3'$, known protecting groups for hydroxyl group can be used. For example, protecting groups for hydroxyl group described in Protecting groups in Organic chemistry (John Wiley & Sons INC., New York 1991, ISBN 0-471-62301-6) can be used. Specific examples of such a protecting group include: arylalkyl groups such as a benzyl group, a p-methoxybenzyl group and a biphenylmethyl group; acyl groups such as an acetyl group; alkoxycarbonyl groups such as a methoxycarbonyl group and a tert-butoxycarbonyl group; and trialkylsilyl groups such as a trimethylsilyl group. Of these, a benzyl group is preferable. $R_3$ and $R_3'$ may be identical to or different from each other. Preferably, $R_3$ and $R_3'$ are identical to each other.

Y and Y' independently represent a hydroxyl group or a halogen atom. Examples of such a halogen atom include a fluorine atom, a chlorine atom, and an iodine atom. Y and Y' are preferably hydroxyl groups.

<Step (a): Esterification Reaction>

This is a step of allowing the carbonyl compounds represented by the formula (4) and the formula (6) to successively act on the trehalose compound represented by the formula (3), so as to carry out an esterification reaction between the trehalose compound and the carbonyl compounds.

The trehalose compound represented by the formula (3) is a trehalose compound whose hydroxyl groups other than those at position 6 and at position 6' are protected by protecting groups. As such a trehalose compound, either a commercially available product, or a compound synthesized from trehalose or the like according to a known method, may be used. For example, 2,3,4,2',3',4'-hexabenzoxy-α,α'-trehalose, the protecting group of which is a benzyl group, is commercially available, and this product can be preferably used. Moreover, an α,α' form of trehalose is naturally present, and thus it can be easily obtained. In trehalose, hydroxyl groups at position 6 and at position 6' have reactivity that is different from that of other hydroxyl groups. Hence, the trehalose compound represented by the formula (3), wherein hydroxyl groups other than those at position 6 and at position 6' are protected, can be relatively easily synthesized by introducing protecting groups for hydroxyl groups into natural trehalose according to a known method.

Furthermore, as carbonyl compounds represented by the formula (4) and the formula (6), commercially available products, compounds synthesized in accordance with the after-mentioned Synthetic Schemes 4, 5 and 6, and compounds synthesized according to a known method, may be used.

In the step of allowing the carbonyl compound represented by the formula (4) to act on the trehalose compound represented by the formula (3), the hydroxyl groups at position 6 and at position 6' in the trehalose compound represented by the formula (3) may be both esterified. A compound, in which both of the hydroxyl groups at position 6 and at position 6' are esterified, is referred to as a diester form. An intermediate compound, in which only either one hydroxyl group is esterified, is referred to as a monoester form. When the carbonyl compound represented by the formula (4) is used in an approximately equivalent amount with respect to the trehalose compound represented by the formula (3), a large amount of monoester form is generated as a result of steric hindrance. In order to enhance the reaction yield of a desired compound, a monoester form, in which the desired hydroxyl group at position 6 has been esterified, may be separated and purified after completion of the reaction. Alternatively, in order to enhance the reaction yield, either one hydroxyl group of the hydroxyl groups at position 6 and at position 6' of the trehalose compound represented by the formula (3) used as a raw material, which is not to be esterified with the carbonyl compound represented by the formula (4), has been selectively protected in advance, and after completion of the esterification reaction of the other hydroxyl group, it may be selectively deprotected. With regard to the order of esterification of hydroxyl groups, the hydroxyl group at position 6 may be previously esterified, or the hydroxyl group at position 6' may also be previously esterified.

In this esterification reaction, methods that are commonly used as general esterification reactions, and methods known to persons skilled in the art, may be broadly applied.

When Y or Y' is a hydroxyl group in the carbonyl compound represented by the formula (4) or the formula (6), a known esterification reaction between carboxylic acid and alcohol can be widely applied. For example, a dehydration method (including a carbodiimide method), a mixed acid anhydride method and an active esterification method can be applied. These methods can be preferably carried out using a condensing agent in an inactive solvent.

The condensing agent used in the aforementioned methods may be a dehydrating agent or any other agent commonly used in the esterification reaction between alcohol and carboxylic acid. Examples of such a condensing agent include: mineral acids such as hydrogen chloride, sulfuric acid and hydrochloric acid; organic acids such as paratoluenesulfonic acid and camphorsulfonic acid; dehydrating agents including Lewis acid such as boron fluoride etherate; acid halides such as phosphorous trichloride, phosphorus tribromide, phosphorus pentachloride, phosphorus oxychloride and thionyl chloride; mixed acid anhydrides such as ethyl chloroformate and methanesulfonyl chloride; carbodiimides such as N,N'-dicyclohexylcarbodiimide (DCC), diisopropylcarbodiimide and 1-ethyl-3-dimethylaminopropylcarbodiimide; and other condensing agents such as N,N-carbonyldiimidazole, 2-ethoxy-N-ethoxycarbonyl-1,2-dihydroquinoline (EEDQ) and triphenylphosphine-carbon tetrachloride (complex). These condensing agents may be used singly or in combination of two or more types. The ratio between a raw material compound and a condensing agent used is not particularly limited, and it can be appropriately selected from a wide range.

The esterification reaction can be carried out in a suitable solvent. The type of such a solvent is not particularly limited, as long as it is an inactive solvent, which has moderate ability to dissolve a raw material compound and which does not affect the esterification reaction. A wide range of known solvents can be used. Examples of a solvent used in the above described esterification reaction include: aromatic hydrocarbons such as benzene, toluene and xylene; halogenated aromatic hydrocarbons such as chlorobenzene and dichlorobenzene; aliphatic hydrocarbons such as n-hexane, cyclohexane and petroleum ether; aliphatic halogenated hydrocarbons such as dichloromethane, 1,2-dichloroethane, chloroform and carbon tetrachloride; ethers such as diethyl ether, diisopropyl ether, dioxane, tetrahydrofuran, ethylene glycol dimethyl ether and ethylene glycol diethyl ether; ketones such as acetone, 2-butanone and methyl isobutyl ketone; nitriles such as acetonitrile, propionitrile and benzonitrile; amides such as N,N-dimethylformamide and hexamethylphosphoric triamide (HMPA); and sulfoxides such as dimethyl sulfoxide. These solvents may be used singly or in combination of two or more types.

Furthermore, in the esterification reaction, a wide range of known reaction promoters can be used. Examples of such a reaction promoter include: catalysts such as dimethylformamide, dimethylamidopyridine and 4-pyrrolidinopyridine; and drying agents such as anhydrous magnesium sulfate and molecular sieves (4A, 5A). These reaction promoters may be added into a reaction system. Further, in order to promote the esterification reaction, apparatuses such as a Dean-Stark water separation apparatus and a Soxhlet extractor may also be used. These reaction promoters or apparatuses may be used singly or in combination of two or more types. A catalyst may be used in combination with a drying agent. The ratio between a raw material compound and a reaction promoter used is not particularly limited, and it can be appropriately selected from a wide range.

The amount of a raw material compound used in the present reaction is not particularly limited, and it can be appropriately selected from a wide range. When the compound represented by the formula (4) and the compound represented by the formula (6) are successively reacted, the carbonyl compound represented by the formula (4) is used in an amount of generally 0.5 to 1.8 moles, and preferably 0.8 to 1.2 moles, with respect to 1 mole of the trehalose compound represented by the formula (3). In addition, the carbonyl compound represented by the formula (6) is used in an amount of generally 0.5 to 1.8 moles, and preferably 0.8 to 1.2 moles, with respect to 1 mole of the monoester form represented by the formula (5).

Moreover, the reaction temperature applied to the esterification reaction is not particularly limited, either. In general, it may be set within the range from −10° C. to the boiling point of a solvent used. The reaction is carried out generally at a temperature from 0° C. to 200° C., and preferably from a room temperature to 100° C.

The reaction time depends on the type of a raw material compound and the amount used, and reaction conditions such as a reaction temperature. In general, the reaction time can be appropriately adjusted within the range from 1 hour to 1 week, and it is preferably 1 to 24 hours, and more preferably 3 to 10 hours.

After completion of the reaction, common treatments such as separation and elimination of by-products, drying, and distillation of a solvent, are performed on a reaction mixture. Thereafter, the reaction product is purified by a common method such as silica gel column chromatography.

When Y or Y' is a halogen atom in the carbonyl compound represented by the formula (4) or the formula (6), the esterification reaction can be carried out in a suitable solvent, and as necessary, in the presence of a base.

As solvents, the same inactive solvents as those used in the above described esterification reaction can be used.

Examples of a base include: alkaline metal hydroxides such as sodium hydroxide and potassium hydroxide; alkaline-earth metal hydroxides such as calcium hydroxide; alkaline metal carbonates such as sodium carbonate and potassium carbonate; alkaline metal hydrogencarbonates such as sodium hydrogencarbonate and potassium hydrogencarbonate; alkaline metal acetates such as sodium acetate and potassium acetate; alkaline-earth metal acetates such as calcium acetate; alkaline metal hydrides such as sodium hydride and potassium hydride; alkaline-earth metal hydrides such as calcium hydride; ammonium salts such as ammonium hydroxide, ammonium carbonate and ammonium acetate; and tertiary amines such as trimethylamine, triethylamine, N,N-dimethylaniline, pyridine, 4-(dimethylamino)pyridine, diazabicyclooctane (DABCO), diazabicyclononene (DBN) and diazabicycloundecene (DBU). These bases may be used singly or in combination of two or more types.

The amounts of a raw material compound and a base that are subjected to the present reaction are not particularly limited. The amounts can be appropriately selected from a wide range. When the compound represented by the formula (4) and the compound represented by the formula (6) are successively reacted, the carbonyl compound represented by the formula (4) is used in an amount of generally 0.5 to 1.8 moles, and preferably 0.8 to 1.2 moles, with respect to 1 mole of the trehalose compound represented by the formula (2). A base is used in an amount of generally 0.5 to 1.8 moles, and preferably 0.8 to 1.2 moles, with respect to 1 mole of the trehalose compound represented by the formula (2). Moreover, the carbonyl compound represented by the formula (6) is used in an amount of generally 0.5 to 1.8 moles, and preferably 0.8 to 1.2 moles, with respect to 1 mole of the monoester form represented by the formula (5). A base is used in an amount of generally 0.5 to 1.8 moles, and preferably 0.8 to 1.2 moles, with respect to 1 mole of the monoester form represented by the formula (5).

As in the case of the aforementioned esterification reaction, the reaction temperature may be generally set within the range from −10° C. to the boiling point of a solvent used. As in the case of the aforementioned esterification reaction, the reaction time depends on the above described concentration, temperature, etc. In general, the reaction time can be appropriately adjusted within the range from 0.1 to 10 hours.

Even when a carbonyl compound in which X represents a hydroxyl group and a carbonyl group in which X' represents a halogen atom are used as the compound represented by the formula (4) and the compound represented by the formula (6), and also when a carbonyl compound in which X represents a halogen atom and a carbonyl group in which X' represents a hydroxyl group are used as the compound represented by the formula (4) and the compound represented by the formula (6), the compound represented by the formula (7) can also be synthesized by appropriately selecting appropriate reaction conditions from the above described reaction conditions.

<Step (b)>

Deprotection of the hydroxyl groups of sugar is carried out on the compound represented by the formula (7) in which the position 6 and position 6' of trehalose have been esterified and the hydroxyl groups of sugar have been protected, which was obtained in the above described step (a), so as to obtain a trehalose diester compound of interest, which is represented by the formula (1).

In order to leave protecting groups from the protected hydroxyl groups in the compound represented by the formula (7), the deprotection method suitable for the protecting groups, which is described in the aforementioned publication, can be appropriately applied, for example.

In a case in which the protecting group for $R_3$ is a benzyl group, for example, a catalytic hydrogenation reaction can be applied. The catalytic hydrogenation reaction is carried out in a hydrogen atmosphere in the presence of a catalyst.

As catalysts, a wide range of known catalysts can be used, as long as they can be used in such a catalytic hydrogenation reaction. Examples of such a catalyst include platinum oxide, platinum carbon, palladium hydroxide, palladium carbon, and Raney nickel.

The catalyst is used in an amount of generally about 0.001% to 50% by weight, and preferably about 0.01% to 10% by weight, with respect to the weight of the compound represented by the formula (7).

The hydrogen pressure is not particularly limited, and it can be appropriately selected from a wide range. It is generally about 0.8 to 100 atmospheres, and preferably about 1 to 3 atmospheres.

This reaction is generally carried out in a suitable solvent. As solvents, a wide range of solvents can be used, as long as they are inactive solvents that do not affect the reaction. Examples of a solvent used herein include: aliphatic halogenated hydrocarbons such as dichloromethane, 1,2-dichloroethane, chloroform and carbon tetrachloride; alcohols such as methanol, ethanol and isopropanol; esters such as methyl formate, methyl acetate and ethyl acetate; carboxylic acids such as formic acid and acetic acid; and the mixed solvents thereof.

The temperature applied in this reaction is generally about 0° C. to 100° C., and preferably about 10° C. to 40° C. The reaction time depends on the amount of a substrate, a temperature, the type of a catalyst, etc. Using the theoretical amount of hydrogen consumption as a guideline, the reaction may be terminated. The reaction time is generally about 1 to 50 hours, and preferably 1 to 30 hours.

After completion of the reaction, common treatments such as the removal of the catalyst by filtration and distillation of the solvent are performed, and the reaction product is then purified by common methods such as solvent extraction and silica gel column chromatography.

The compound represented by the formula (1) of the present invention can also be produced by the methods shown in the following Synthetic Scheme 2 or Synthetic Scheme 3.

19

<Synthetic Scheme 2>

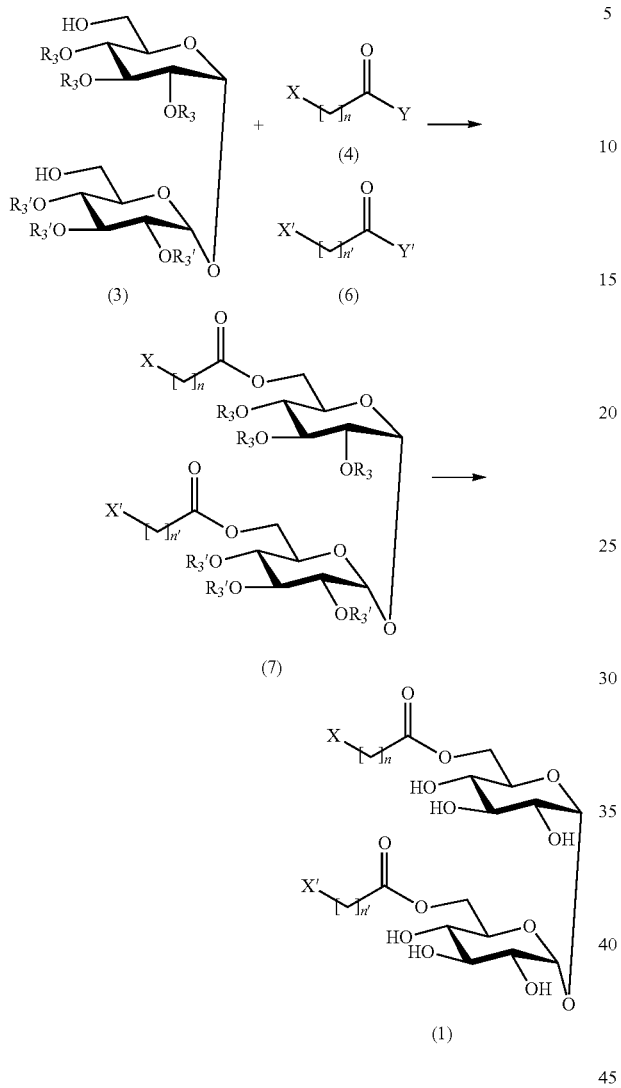

(In the above synthetic scheme, $R_1$, $R_1'$, $R_2$, $R_2'$, $R_3$, $R_3'$, n and n' have the same definitions as those described above.

Synthetic Scheme 2 is a scheme whereby the carbonyl compounds represented by the formula (4) and the formula (6) are allowed to simultaneously act on the trehalose compound represented by the formula (3) in the step (a) that is an esterification reaction. The step (b) that is a deprotection reaction is the same as that in Synthetic Scheme 1.

The esterification reaction and the deprotection reaction can be carried out in the same manner as that in Synthetic Scheme 1 with the exception that the carbonyl compounds represented by the formula (4) and the formula (6) are allowed to simultaneously act on the trehalose compound represented by the formula (3) in the step (a).

When the carbonyl compounds represented by the formula (4) and the formula (6) are allowed to simultaneously act on the aforementioned trehalose compound, a compound of interest can be obtained by separating and purifying it from the generated product.

When $R_1$ and $R_1'$, $R_2$ and $R_2'$, and n and n' are identical to each other in the compound represented by the formula (1), the above described Synthetic Scheme 2 can be particularly

20 represented by Synthetic Scheme 3 below. When $R_1$ and $R_1'$, $R_2$ and $R_2'$, and n and n' are not identical to each other in the compound represented by the formula (1), from the viewpoint of the enhancement of a reaction yield, the compound is preferably synthesized by the method as shown in Synthetic Scheme 1.

<Synthetic Scheme 3>

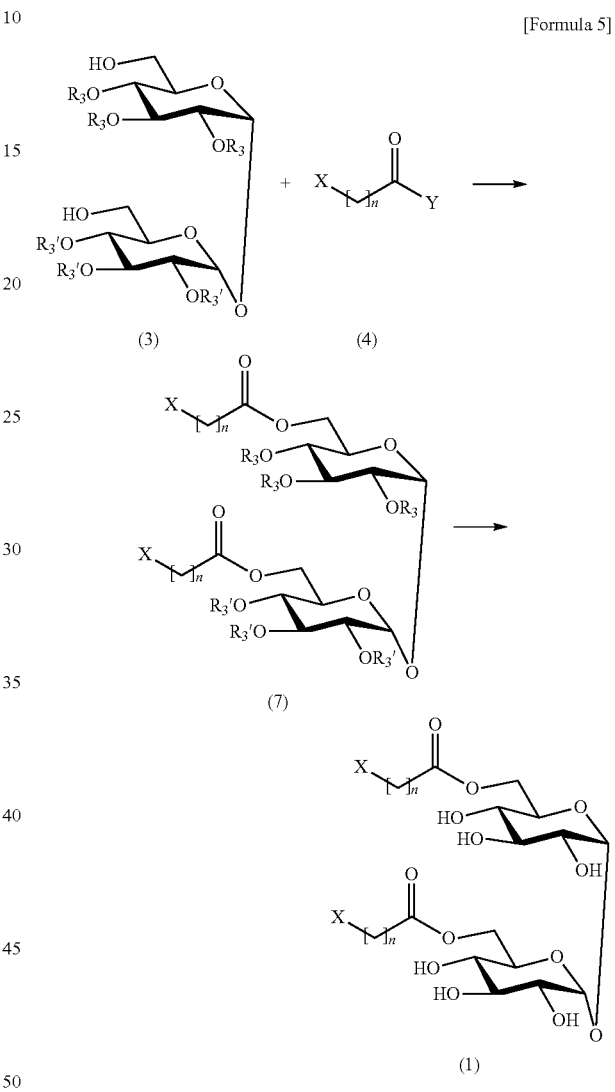

In the above synthetic scheme, $R_1$, $R_2$, $R_3$, $R_3'$ and n have the same definitions as those described above.

In Synthetic Scheme 3, only one type of carbonyl compound (4) is allowed to act on the trehalose compound represented by the formula (3) in the step (a) that is an esterification reaction. Thus, this is a scheme whereby the esterification reaction is carried out simultaneously, namely, at a single reaction stage, and the step (b) that is a deprotection reaction is the same as that in Synthetic Scheme 1.

The esterification reaction and the deprotection reaction in Synthetic Scheme 3 can be carried out in the same manner as the reaction in the above described Synthetic Scheme 1 with the exception that the used amount of the carbonyl compound represented by the formula (4) is increased. With regard to the used amount, specifically, with respect to 1 mole of the trehalose compound represented by the formula (3), the carbonyl compound represented by the formula (4) is used in an amount of generally 1.8 to 5 moles, and preferably 2 to 3 moles; a condensing agent is used in an amount of generally 1.8 to 5 moles, and preferably 2 to 4 moles; and a base is used in an amount of 1.8 to 8 moles, and preferably 2 to 6 moles.

The compound represented by the formula (7) may be used to the subsequent reaction without performing isolation and purification. However, it is preferable to remove reagents used in the esterification and by-products before subjecting the compound to the subsequent reaction.

<Carbonyl Compounds used as Raw Materials>

As the carbonyl compound represented by the formula (4) or the formula (6), which is used as a raw material compound in the above described Synthetic Scheme 1, 2 or 3, a commercially available product can be used, or a compound can be produced by a method known to persons skilled in the art. For example, as a compound wherein, in the formula (4) or the formula (6), X or X' represents a phenyl group and n or n' represents 0, benzoic acid or a benzoic acid halide can be used.

Among the compounds represented by the formula (4), a compound, wherein X represents $R_1$—$CHR_2$— and n represents 0, can also be produced by the following Synthetic Scheme 4 or 5.

Hereafter, the carbonyl compound represented by the formula (4) is described as a compound of interest. However, the carbonyl compound represented by the formula (6) can also be produced in the same manner.

<Synthetic Scheme 4>

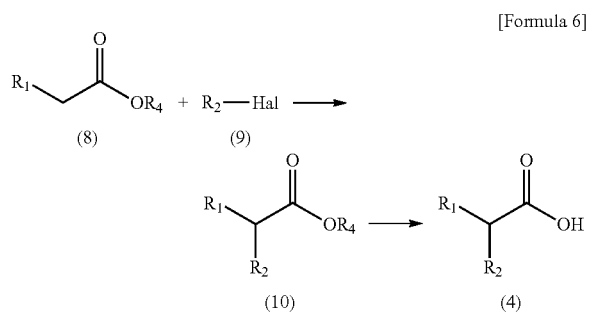

[Formula 6]

In the above synthetic scheme, $R_1$ and $R_2$ have the same definitions as those described above. $R_4$ represents an alkyl group containing 1 to 6 carbon atoms, and Hal represents a halogen atom.

Synthetic Scheme 4 is a step of subjecting the compound represented by the formula (8) to an ordinary alkylation reaction to obtain the carbonyl compound represented by the formula (4). A commercially available product can be used as the compound represented by the formula (8) that is a raw material compound. When $R_1$ is a linear alkyl group containing 10 carbon atoms, for example, ethyl dodecanoate or the like can be used. An acid ester having a desired length as a side chain alkyl of a compound of interest may be used.

Various methods, such as the method described in Creger, J. Am. Chem. Soc., Vol. 92, pp. 1397-98, 1970, can be used in the alkylation reaction. More specifically, a strong base may be added to a solution of the compound represented by the formula (8) to eliminate the hydrogen atom at position 2 and thereafter, an alkyl halide may be allowed to react with the compound represented by the formula (8). As an example, alkylation can be carried out by the following reaction.

First, the compound represented by the formula (8) is allowed to react with a strong base. The type of such a strong base is not particularly limited, as long as it has action to eliminate a hydrogen atom. Examples of such a strong base include: alkaline metal hydroxides such as sodium hydroxide and potassium hydroxide; and alkaline-earth metal hydroxides such as calcium hydroxide. These bases may be used singly or in combination of two or more types. Moreover, lithium diisopropylamide may be used in combination, so as to carry out a proton-lithium exchange reaction. The type of a solvent is not particularly limited, as long as it is an inactive solvent, which has moderate ability to dissolve a raw material compound and which does not affect the esterification reaction. A wide range of known solvents can be used. Examples of a solvent used in the above described alkylation reaction include: aromatic hydrocarbons such as benzene, toluene and xylene; aliphatic hydrocarbons such as n-hexane, cyclohexane and petroleum ether; and ethers such as diethyl ether, diisopropyl ether, dioxane, tetrahydrofuran, ethylene glycol dimethyl ether, and ethylene glycol diethyl ether. These solvents may be used singly or in combination of two or more types.

In the present reaction, the ratio between the compound represented by the formula (8) and the strong base can be appropriately selected from a wide range. In general, the strong base or the like is used in an amount of approximately 0.9 to 5 times the mole of the compound represented by the formula (8). The reaction temperature applied in this reaction is generally about −80° C. to 60° C., and preferably about 0° C. to 60° C. The reaction time is set at about 5 minutes to 6 hours, and preferably about 5 minutes to 1 hour.

Subsequently, an alkyl halide is added to the reaction mixture. As such an alkyl halide, an alkane halide having a desired length of carbon chain portion, such as 1-iodooctane, 1-iodoheptane, 1-iododecane, 1-iodoundecane, 1-iodododecane or 1-iodotridecane, may be used as an alkyl group on the side chain of a compound of interest. Halides include a chloride, an iodide, a bromide, and the like. Of these, an iodide is preferable. In the present reaction, the ratio between the compound represented by the formula (8) and the alkyl halide can be appropriately selected from a wide range. In general, the alkyl halide is used in an amount of approximately 1.1 to 3 times the mole of the compound represented by the formula (8). The reaction temperature applied in this reaction may be generally set around a room temperature. The reaction time is generally set at about 2 to 12 hours.

After completion of the reaction, a known isolation and purification method, such as silica gel column chromatography or vacuum distillation, is applied to isolate and purify the compound of interest.

Among the compounds represented by the formula (4), a compound, wherein X represents $R_1$—$CHR_2$— and n represents 0, can also be produced by the following Synthetic Scheme 5.

<Synthetic Scheme 5>

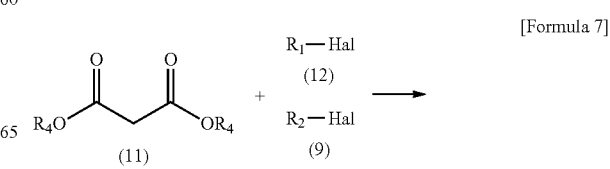

[Formula 7]

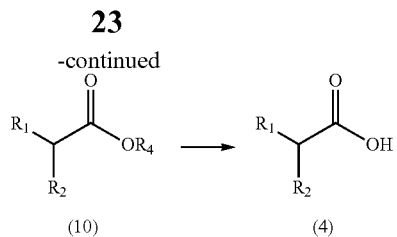

(10) → (4)

In the above synthetic scheme, $R_1$, $R_2$, $R_4$ and Hal have the same definitions as those described above.

Synthetic Scheme 5 is a step of subjecting the compound represented by the formula (11) to an ordinary alkylation reaction to obtain the carbonyl compound represented by the formula (4). A commercially available product can be used as the compound represented by the formula (11) that is a raw material compound. Examples of such a commercially available product include diethyl malonate, dimethyl malonate, dipropyl malonate, dibutyl malonate, diisopropyl malonate, di-tert-butyl malonate, dicyclohexyl malonate, diphenyl malonate, and dibenzyl malonate.

As described above, the alkylation reaction can be carried out by allowing a strong base to react with the compound represented by the formula (11) used as a raw material compound, and then allowing an alkyl halide to act on the aforementioned compound.

In the step of allowing a strong base to react with the compound represented by the formula (11), the ratio between the compound represented by the formula (11) and the strong base can be appropriately selected from a wide range. In general, the strong base or the like is used in an amount of approximately 0.9 to 5 times the mole of the compound represented by the formula (11). The reaction temperature applied in this reaction is generally about −80° C. to 60° C., and preferably about 0° C. to 60° C. The reaction time is set at about 5 minutes to 6 hours, and preferably about 5 minutes to 1 hour.

Subsequently, in the step of adding an alkyl halide to the reaction mixture, the ratio between the compound represented by the formula (11) and the alkyl halide can be appropriately selected from a wide range. In general, the alkyl halide represented by the formula (12) and the alkyl halide represented by the formula (9) are used in each amount of approximately 0.8 to 1.2 times the mole of the compound represented by the formula (11). When the compound of interest is a compound wherein $R_1$ and $R_2$ are identical to each other, only one type of alkyl halide may be used. In general, such an alkyl halide is used in an amount of approximately 2.2 to 4 times the mole of the compound represented by the formula (11). On the other hand, when the compound of interest is a compound wherein $R_1$ and $R_2$ are not identical to each other, as described above, the alkyl halide represented by the formula (12) and the alkyl halide represented by the formula (9) are allowed to simultaneously act on the compound, so that only the compound of interest can be isolated and purified. Otherwise, different alkyl halides are allowed to successively act on the compound, namely, after one type of alkyl halide has been allowed to act on the compound, the other type of alkyl halide is allowed to act thereon, and thereafter, the compound of interest may be isolated and purified. As such isolation and purification methods, known isolation and purification methods, such as silica gel column chromatography or vacuum distillation, can be applied.

Among the compounds represented by the formula (4), a compound, wherein X represents $R_1$—$CHR_2$— and n represents 1, can also be produced by the following Synthetic Scheme 6.

<Synthetic Scheme 6>
Synthetic Scheme 6 can be described in the following Synthetic Schemes 6-1 to 6-5.
<Synthetic Scheme 6-1>

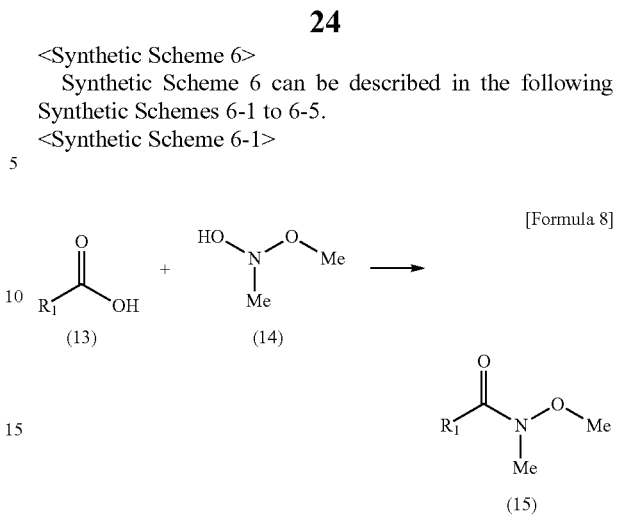

[Formula 8]

(13) (14) (15)

In the above synthetic scheme, $R_1$ has the same definitions as those described above.

Synthetic Scheme 6-1 is a reaction regarding the dehydration binding of N,O-dimethylhydroxyamine to carboxylic acid used as a raw material compound.

A basic condensing agent is allowed to act on the carboxylic acid represented by the formula (13). A wide range of known basic condensing agents can be used herein. Examples of such a basic condensing agent include carbonyldiimidazole, 4-dimethylaminopyridine, piperidine, pyrrolidine, pyridine, imidazole, N,N,N',N'-tetramethylurea, bis(pentamethylene)urea, and 1,1-carbonyldipyrrole. A commercially available product can be used as the carboxylic acid that is a raw material compound. For example, heptanoic acid, octanoic acid, decanoic acid, and undecanoic acid are used. An acid having a desired length as a side chain alkyl of a compound of interest may be used. As solvents, a wide range of solvents can be used, as long as they are inactive solvents, which have moderate ability to dissolve a raw material compound and which do not affect the esterification reaction. Examples of a solvent used in the above described esterification reaction include: aromatic hydrocarbons such as benzene, toluene and xylene; halogenated aromatic hydrocarbons such as chlorobenzene and dichlorobenzene; aliphatic hydrocarbons such as n-hexane, cyclohexane and petroleum ether; aliphatic halogenated hydrocarbons such as dichloromethane, 1,2-dichloroethane, chloroform and carbon tetrachloride; and ethers such as diethyl ether, diisopropyl ether, dioxane, tetrahydrofuran, ethylene glycol dimethyl ether and ethylene glycol diethyl ether. These solvents may be used singly or in combination of two or more types.

In the present reaction, the use ratio between the carboxylic acid represented by the formula (13) and carbonyldiimidazole or the like can be appropriately selected from a wide range. In general, it is approximately 0.8 to 2.0 moles. The reaction temperature applied in this reaction is generally about −80° C. to 60° C., and preferably about 0° C. to 60° C. The reaction time is set at about 5 minutes to 6 hours, and preferably about 30 minutes to 3 hours.

Subsequently, the N,O-dimethylhydroxyamine represented by the formula (14) is allowed to react with the reaction product. 1-hydroxybenzotriazole or the like may also be used instead of the N,O-dimethylhydroxyamine. The ratio between the carboxylic acid represented by the formula (13) and the N,O-dimethylhydroxyamine can be appropriately selected from a wide range. In general, the N,O-dimethylhydroxyamine may be used in an amount of approximately 0.8 to 1.5 moles with respect to 1 mole of the carboxylic acid represented by the formula (13). The reaction temperature is generally about −80° C. to 60° C., and preferably about 0° C. to 60° C. The reaction time may be set at about 10 minutes to 10 hours.

After completion of the reaction, a known isolation and purification method, such as silica gel column chromatography or vacuum distillation, is applied to isolate and purify the compound of interest.

<Synthetic Scheme 6-2>

[Formula 9]

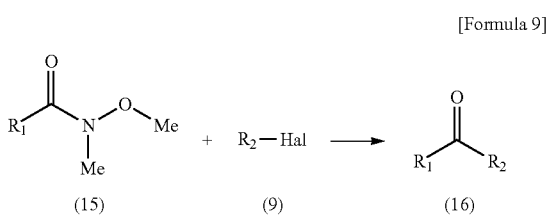

In the above synthetic scheme, $R_1$, $R_2$ and Hal have the same definitions as those described above.

Synthetic Scheme 6-2 is a reaction of allowing an alkyl halide to act on the compound represented by the formula (15) to synthesize a ketone body.

In the present reaction, the alkyl halide represented by the formula (9) may be allowed to act on metallic magnesium in an ether solvent to prepare a Grignard reagent, and the thus prepared reagent may be used in the reaction. As such a metallic magnesium, polished shaved magnesium is preferably used. In addition, lithium, sodium, zinc, indium or the like may also be used.

As the alkyl halide represented by the formula (9), the same alkyl halides as those described above can be used.

The present reaction is carried out in an ether solvent. Examples of such an ether solvent include diethyl ether, diisopropyl ether, dioxane, tetrahydrofuran, tetrahydropyran, ethylene glycol dimethyl ether and ethylene glycol diethyl ether. These solvent may be used singly or in combination of two or more types.

In the present reaction, the ratio between the compound represented by the formula (15) and the alkyl halide can be appropriately selected from a wide range. In general, the alkyl halide is used in an amount of approximately 0.8 to 5 times the mole of the compound represented by the formula (15). The reaction temperature applied in this reaction is generally about 0° C. to 80° C. The reaction time is about 5 minutes to 6 hours.

After completion of the reaction, a known isolation and purification method, such as silica gel column chromatography or vacuum distillation, is applied to isolate and purify the compound of interest.

<Synthetic Scheme 6-3>

[Formula 10]

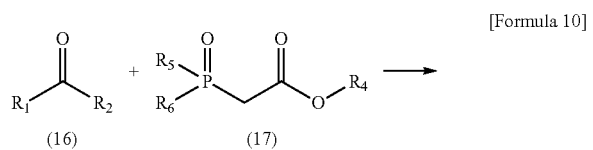

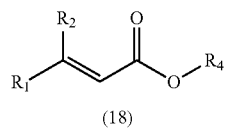

In the above synthetic scheme, $R_1$, $R_2$ and $R_4$ have the same definitions as those described above. $R_5$ and $R_6$ each represent an alkyl group, an alkoxy group, an aryl group, or an aryloxy group. These groups may be replaced by a halogen atom and the like.

Synthetic Scheme 6-3 is a reaction of allowing a Wittig reagent or a Horner-Emmons reagent to react with the ketone compound represented by the formula (16) in the presence of a strong base, so as to form a carbon-carbon double bond. The compound represented by the formula (17) in the above described synthetic scheme is a Horner-Emmons reagent. Instead of the Horner-Emmons reagent, the Wittig reagent may also be used.

The type of such a strong base is not particularly limited, as long as it has action to eliminate a hydrogen atom. Examples of such a strong base include: alkaline metal hydroxides such as sodium hydroxide and potassium hydroxide; and alkaline-earth metal hydroxides such as calcium hydroxide. These bases may be used singly or in combination of two or more types. The type of a solvent is not particularly limited, as long as it is an inactive solvent, which has moderate ability to dissolve a raw material compound and which does not affect the esterification reaction. A wide range of known solvents can be used. Examples of a solvent used in the present reaction include: aromatic hydrocarbons such as benzene, toluene and xylene; aliphatic hydrocarbons such as n-hexane, cyclohexane and petroleum ether; and ethers such as diethyl ether, diisopropyl ether, dioxane, tetrahydrofuran, ethylene glycol dimethyl ether, and ethylene glycol diethyl ether. These solvents may be used singly or in combination of two or more types.

In the present reaction, the ratio between the compound represented by the formula (16) and the strong base can be appropriately selected from a wide range. In general, the strong base or the like is used in an amount of approximately 1.1 to 8 times the mole of the compound represented by the formula (16). The reaction temperature applied in this reaction is generally about −80° C. to 60° C. The reaction time is generally set at about 5 minutes to 3 hours.

Subsequently, a Wittig reagent or a Horner-Emmons reagent is allowed to react with the reaction mixture. As such a Wittig reagent or a Horner-Emmons reagent, a wide range of known reagents can be used. The type of such an agent is not particularly limited, as long as it is able to form a carbon-carbon double bond between the ketone compound represented by the formula (16) and an acid ester. Examples of a Wittig reagent include ethoxycarbonylmethyl(triphenyl)phosphonium bromide and ethyl(triphenylphosphoranylidene)acetate. Examples of a Horner-Emmons reagent include ethyl(diaryl)phosphonoacetates such as ethyl diphenylphosphonoacetate, and ethyl(dialkyl)phosphonoacetates such as ethyl diethylphosphonoacetate. Of these, ethyl diethylphosphonoacetate is preferable.

In the present reaction, the ratio between the compound represented by the formula (16) and ethyl diethylphosphonoacetate can be appropriately selected from a wide range. In general, ethyl diethylphosphonoacetate is used in an amount of approximately 1.1 to 10 times the mole of the compound represented by the formula (16). The reaction temperature applied in this reaction may be generally set at a room temperature. The reaction time is generally set at about 2 to 30 hours.

After completion of the reaction, a known isolation and purification method, such as silica gel column chromatography or vacuum distillation, is applied to isolate and purify the compound of interest.

<Synthetic Scheme 6-4>

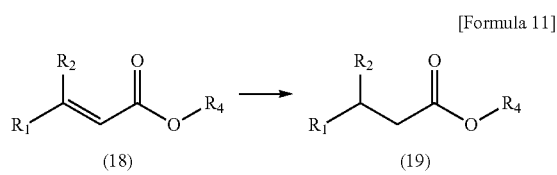

[Formula 11]

In the above synthetic scheme, $R_1$, $R_2$ and $R_4$ have the same definitions as those described above.

Synthetic Scheme 6-4 is a reaction of performing a catalytic hydrogenation reaction on the carboxylic acid ester having an unsaturated bond, represented by the formula (18), so as to convert it to a saturated carboxylic acid ester.

The catalytic hydrogenation reaction is carried out in a hydrogen atmosphere in the presence of a catalyst.

As catalysts, a wide range of known catalysts can be used, as long as they can be used in a catalytic hydrogenation reaction. Examples of such a catalyst include platinum oxide, platinum carbon, palladium hydroxide, palladium carbon, and Raney nickel.

The catalyst is used in an amount of generally about 0.001% to 50% by weight, and preferably about 0.01% to 10% by weight, with respect to the weight of the compound represented by the formula (18).

The hydrogen pressure is not particularly limited, and it can be appropriately selected from a wide range. It is generally about 0.8 to 100 atmospheres, and preferably about 1 to 3 atmospheres.

This reaction is generally carried out in a suitable solvent. As solvents, a wide range of solvents can be used, as long as they are inactive solvents that do not affect the reaction. Examples of a solvent used herein include: aliphatic halogenated hydrocarbons such as dichloromethane, 1,2-dichloroethane, chloroform and carbon tetrachloride; alcohols such as methanol, ethanol and isopropanol; esters such as methyl formate, methyl acetate and ethyl acetate; carboxylic acids such as formic acid and acetic acids; and the mixed solvents thereof.

The temperature applied in the present reaction is generally about 0° C. to 100° C., and preferably about 10° C. to 40° C. The reaction time depends on the amount of a substrate, a temperature, the type of a catalyst, etc. Using the theoretical amount of hydrogen consumption as a guideline, the reaction may be terminated. The reaction time is generally about 1 to 50 hours, and preferably 1 to 30 hours.

After completion of the reaction, common treatments such as the removal of the catalyst by filtration and distillation of the solvent are performed, and the reaction product is then purified by common methods such as solvent extraction and silica gel column chromatography.

<Synthetic Scheme 6-5>

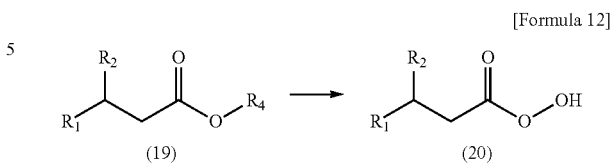

[Formula 12]

In the above synthetic scheme, $R_1$, $R_2$ and $R_4$ have the same definitions as those described above.

Synthetic Scheme 6-5 is a reaction of hydrolyzing the carboxylic acid ester represented by the formula (19) to obtain desired carboxylic acid.

As such hydrolytic reactions, various types of known reactions can be used. Such a hydroxylic reaction is carried out under acidic conditions or under basic conditions, or it may be carried out in the form of an enzyme reaction.

In order to create basic conditions, a base may be added to a solvent. As such bases, a wide range of substances can be used, as long as they generate hydride ions. Examples of such a base include: alkaline metal hydroxides such as sodium hydroxide and potassium hydroxide; alkaline-earth metal hydroxides such as calcium hydroxide; alkaline metal carbonates such as sodium carbonate and potassium carbonate; alkaline metal hydrogencarbonates such as sodium hydrogencarbonate and potassium hydrogencarbonate; alkaline metal acetates such as sodium acetate and potassium acetate; alkaline-earth metal acetates such as calcium acetate; alkaline metal hydrides such as sodium hydride and potassium hydride; alkaline-earth metal hydrides such as calcium hydride; ammonium salts such as ammonium hydroxide, ammonium carbonate and ammonium acetate; and tertiary amines such as trimethylamine, triethylamine, N,N-dimethylaniline, pyridine, 4-(dimethylamino)pyridine, diazabicyclooctane (DABCO), diazabicyclononene (DBN) and diazabicycloundecene (DBU). These bases may be used singly or in combination of two or more types.

The solvent may be an inactive solvent, which has moderate ability to dissolve a raw material compound and which does not affect the esterification reaction. A wide range of known solvents can be used. Examples of a solvent used in the above described esterification reaction include: aromatic hydrocarbons such as benzene, toluene and xylene; halogenated aromatic hydrocarbons such as chlorobenzene and dichlorobenzene; aliphatic hydrocarbons such as n-hexane, cyclohexane and petroleum ether; aliphatic halogenated hydrocarbons such as dichloromethane, 1,2-dichloroethane, chloroform and carbon tetrachloride; ethers such as diethyl ether, diisopropyl ether, dioxane, tetrahydrofuran, ethylene glycol dimethyl ether and ethylene glycol diethyl ether; ketones such as acetone, 2-butanone and methyl isobutyl ketone; nitriles such as acetonitrile, propionitrile and benzonitrile; amides such as N,N-dimethylformamide and hexamethylphosphoric triamide (HMPA); and sulfoxides such as dimethyl sulfoxide. These solvents may be used singly or in combination of two or more types.

In the present reaction, the reaction temperature, the reaction time, and the like can be appropriately selected from a wide range. The reaction temperature is generally about 0° C. to 100° C. The reaction time is generally about 30 minutes to 20 hours.

After completion of the reaction, a known isolation and purification method, such as silica gel column chromatography or vacuum distillation, is applied to isolate and purify the compound of interest.

Among the compounds represented by the formula (4), a compound, wherein X represents R$_1$-CHR$_2$- and n represents 2, can also be produced by the following Synthetic Scheme 7, for example.
<Synthetic Scheme 7>

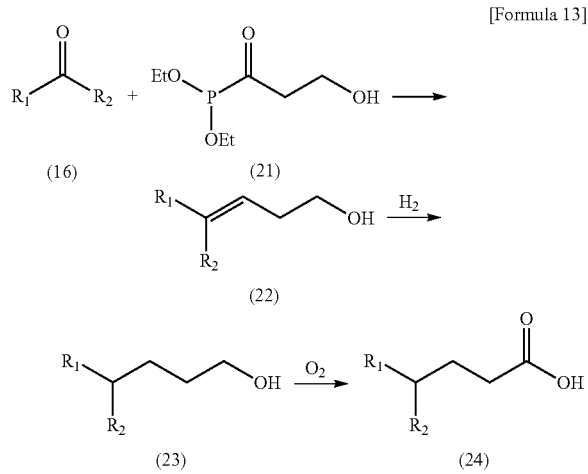

[Formula 13]

In the above synthetic scheme, R$_1$ and R$_2$ have the same definitions as those described above.

Synthetic Scheme 7 is a reaction in which the diethyl 3-hydroxypropanoylphosphonate represented by the formula (21) is allowed to react as a Horner-Emmons reagent with the ketone compound represented by the formula (16) to form a carbon-carbon double bond, so as to obtain the compound represented by the formula (22), a catalytic hydrogenation reaction is then performed thereon to obtain the compound represented by the formula (23), an oxidation reaction of alcohol is then performed thereon to obtain the compound represented by the formula (24) as a carbonyl compound. In the above synthetic scheme, only one of cis-trans stereoisomers of double bond is described with regard to the compound represented by the formula (22). However, examples of such stereoisomers are not limited to the aforementioned stereoisomer.

The reaction using a Horner-Emmons reagent and the catalytic hydrogenation reaction can be carried out in the same manner as described above, while referring to Synthetic Scheme 6-3 and Synthetic Scheme 6-4, respectively. In addition, the oxidation reaction of alcohol can be carried out by oxidizing alcohol with a strong oxidizer. Such an alcohol oxidation reaction can be carried out, as appropriate, according to a known method such as oxidation with chromic acid or Jones oxidation. As an example, oxidation with chromic acid can be carried out using the salts or complexes of chromic anhydride, chromic acid, dichromic acid, etc.

After completion of the reaction, common treatments such as the removal of the catalyst by filtration and distillation of the solvent are performed, and the reaction product is then purified by common methods such as solvent extraction and silica gel column chromatography.

In the present invention, the term "immunostimulation" means the activation of various immune actions such as cellular immunity or humoral immunity. The immunostimulator may be an agent that exhibits any of these immunostimulatory actions. The trehalose compound of the present invention is considered to carry out the activation of the immune actions of macrophages or neutrophils, which are referred to as, at least, cellular immunity in the immune system. A wide range of circumstances, in which the aforementioned cells release cytokines as a result of the activation of cellular immunity, and thereby humoral immunity is also activated, are also included in the immunostimulation.

Macrophage originally has phagocytosis to foreign matters entering from the outside. In the present specification, the term "macrophage activation" means action to enhance the phagocytosis of macrophage, and as a result, the adhesive property of macrophage to tissues and the mobility thereof are improved, and it englobes bacteria invading from the outside and degenerated self-components. In a state in which macrophages are activated, it has been known that the release of nitric oxide (NO) and the release of active oxygen are increased. The released amounts of these free substances are measured, and the obtained value can be used as an indicator of macrophage activation. In addition, acceleration in the phagocytosis itself is measured, and the obtained value can also be used as an indicator of macrophage activation.

Neutrophil itself originally has phagocytosis to foreign matters, as with macrophage. In the present specification, the term "neutrophil activation" means action to enhance the phagocytosis of neutrophil, and as a result, the neutrophil englobes bacteria and the like. Also, in a state in which neutrophils are activated, it has been known that the release of nitric oxide (NO) and the release of active oxygen are increased. It has also been known that the release of physiologically active substances is observed as a result of degranulation of microgranules and azurophile granules by neutrophil activation. The released amounts of these free substances are measured, and the obtained value can be used as an indicator of neutrophil activation. In addition, acceleration in the phagocytosis itself is measured, and the obtained value can also be used as an indicator of neutrophil activation.

In the present specification, phagocytic cells include macrophages, monocytes, polymorphonuclear leukocytes, dendritic cells, and the like. The "phagocytosis" means the action of these cells as immune-system cells to incorporate foreign matters from the outside, such as pathogen bacteria, into the vesicles thereof and to fuse the vesicles with lysosomes in the cells, so as to digest the foreign matters. Activation of the phagocytosis of phagocytic cells is not particularly limited, as long as it is action to activate any of these phagocytic cells so as to enhance the phagocytosis thereof. Such activation of the phagocytosis of phagocytic cells is preferably action to accelerate the phagocytosis of either one or both of macrophage and neutrophil.

In the present specification, the type of an anti-bacterial infection agent is not particularly limited, as long as it is able to reduce infectious disease caused by bacteria, namely, various symptoms caused by the presence of bacteria in a body. Examples of bacteria include Welch *bacillus*, *Pseudomonas aeruginosa*, and enteropathogenic *Escherichia coli*.

In the present specification, the bacterial toxin neutralizer means an agent for reducing the action of toxin generated by bacteria. Anti-bacterial infection agents include those that suppress the growth of bacteria or the release of toxin from bacteria, so as to reduce various symptoms caused by bacteria. On the other hand, toxin neutralizers include those that reduce the action of toxin even under circumstances in which only the toxin acts on a living body. Such action includes action to adsorb toxin, action to modify toxin to an inactive product, action to incorporate toxin into phagocytic cells, and further action to digest the thus incorporated toxin.

In the present invention, the anticancer agent means an agent, which has antitumor activity and is used for the prevention or treatment of cancer. The tumor, on which the anticancer agent of the present invention acts, includes both primary tumor and metastatic tumor. Accordingly, the anticancer agent of the present invention may be used not only for the treatment of primary cancer and metastatic tumor, but also for prevention of metastatic tumor at the same time of or after the treatment of primary cancer. Moreover, in the present invention, examples of the tumor, on which the anticancer agent acts, include breast cancer, testicular cancer, orchioncus, pancreatic cancer, phrenic tumor, lung cancer, ovarian cancer, stomach cancer, gallbladder cancer, kidney cancer, prostatic cancer, esophageal cancer, liver cancer, oral cancer, colonic cancer, large bowel cancer, rectal cancer, uterine cancer, bile duct cancer, islet cell adenoma, adrenal cortical carcinoma, bladder cancer, thyroid cancer, skin cancer, malignant carcinoid tumor, melanoma, glioma, osteosarcoma, myeloma, soft tissue sarcoma, neuroblastoma, malignant lymphoma, and leukemia. Of these, breast cancer, testicular cancer, pancreatic cancer or pherenic cancer is preferable.

In the present specification, the trehalose compound of the present invention, or a pharmaceutical composition comprising the aforementioned compound and a pharmaceutically acceptable carrier, can be used as a pharmaceutical product such as an immunostimulator, a bacterial toxin neutralizer or an anticancer agent.

In the present specification, a pharmaceutically acceptable carrier is not particularly limited, as long as it is pharmacologically and pharmaceutically acceptable. Examples of such a pharmaceutically acceptable carrier include: carriers commonly used in the production of pharmaceutical preparations, such as an excipient, a binder, a dispersant, a thickener, a lubricant, a pH adjuster or a solubilizer; an antibiotic; an antibacterial agent; a disinfectant; an antiseptic; a builder; a bleaching agent; an enzyme; a chelating agent; a defoaming agent; a coloring agent (a dye, a pigment, etc.); a softening agent; a moisturizing agent; a surfactant; an antioxidant; an aromatic; a corrigent; a flavoring agent; and a solvent. The pharmaceutically acceptable carrier can be mixed within the range that does not impair the activity of the trehalose compound (1) of the present invention. Addition of such a carrier may have influence on the absorbing property of the trehalose compound (1) of the present invention or the blood concentration thereof, and thus it is also possible to change the disposition of the compound.

In the present specification, the method for administering the compound of the present case means a method for administering the trehalose compound of the present invention itself or a pharmaceutical composition comprising the present compound to a human or an animal. The compound of the present case or the pharmaceutical composition can be formulated in the form of an ordinary medical preparation. Such a medical preparation can be prepared, as appropriate, using the aforementioned pharmacological carrier. The dosage form is not particularly limited, and it is selected and used, as appropriate, depending on therapeutic purpose. Representative examples of a dosage form include a tablet, a pill, a powder, a liquid agent, a suspension, an emulsion, a granule, a capsule, a suppository, an injection (an liquid agent, a suspension, an emulsion, etc.) These pharmaceutical preparations may be produced by a commonly used method.

The dose of the aforementioned medical preparation may be selected, as appropriate, depending on direction of use, the age and sex of a patient, the degree of disease, and other conditions. In general, the trehalose compound (1) used as an active ingredient is administered in a dose of 0.01 to 100 mg, and preferably 0.1 to 50 mg per day per kg of body weight, once or divided over several administrations.

The aforementioned dose may be fluctuated depending on various conditions. Thus, there is a case in which a dose smaller than the aforementioned range is sufficient. Also, there is a case in which a dose higher than the aforementioned range is necessary.

It is to be noted that the terms are used to explain specific embodiments in the present specification. Thus, they are not intended to limit the scope of the invention.

In addition, the term "include" used in the present specification intends to mean that the described matters (a member, a step, an element, a number, etc.) are present, and thus, it does not exclude the presence of other matters (a member, a step, an element, a number, etc.), with the exception that the term "include" should be contextually understood in an apparently different way.

Unless there are other definitions, all of the terms used herein (including technical terms and scientific terms) have the same meanings as those broadly understood by persons skilled in the technical field, to which the present invention pertains. Unless other definitions are clearly stated, the terms used herein should be understood to have meanings that are compatible with the meanings used in the present specification and the related technical field, and the terms should not be interpreted to have ideal meanings or excessively formal meanings.

There may be a case in which the embodiment of the present invention is described with reference to a schematic view. When such a schematic view is used, there may be a case in which exaggerated descriptions are used to provide clear explanation.

The terms such as "first" and "second" are used to indicate various elements. However, it is understood that these elements should not be restricted by such terms. These terms are used to distinguish one element from other elements. Thus, it is possible to indicate, for example, the first element as the second element, and likewise, to indicate the second element as the first element. This does not deviate from the scope of the present invention.

Hereinafter, the present invention will be more specifically described in the following examples. These examples are not intended to limit the present invention. It may also be possible to add modification to the present invention, as appropriate, within the range suitable for the above-mentioned or aftermentioned contents. Such modified inventions are also included in the technical scope of the present invention.

EXAMPLES

Example: Chemical Synthesis of trehalose diester Compound

The trehalose compound represented by the formula (3) of Synthetic Scheme 1, wherein the hydroxyl group of sugar has been protected, and a desired carbonyl compound represented by the formula (4) or the formula (6), were subjected to an esterification reaction, so as to synthesize the compound represented by the formula (7). Thereafter, the hydroxyl group of sugar was deprotected, so as to obtain a desired trehalose diester compound.

Several production examples will be described below. However, these production examples are not intended to limit the scope of the present invention.

Production Example A-1

Synthesis of 6,6'-bis-O-(2-decyldodecanoyl)-2,3,4,2',3',4'-hexabenzyl-α,α'-trehalose

[Formula 14]

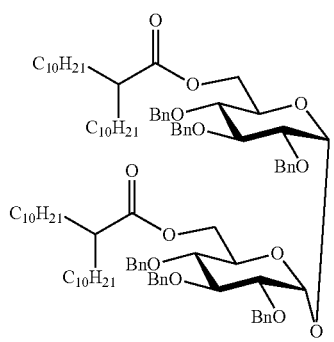

The carboxylic acid (2-decyldodecanoic acid) (145 mg, 425 μmol) obtained by the method described in Production Example C-1 and a trehalose derivative (2,3,4,2',3',4'-hexabenzoxy-α,α'-trehalose) (150 mg, 170 μmol) were dissolved in an anhydrous dichloromethane solution (2 ml). Thereafter, powdered molecular sieves 4A (0.3 g), 4-dimethylaminopyridine (20.8 mg, 170 μmol), 1-ethyl-3-(3-dimethylaminopropyl)carbodiimide hydrochloride [hereinafter abbreviated as EDCI] (97.8 mg, 510 μmol) were successively added to the solution, and the mixed solution was then heated to reflux for 4 hours. Thereafter, the reaction solution was filtrated with Celite-535, and distilled water was then added thereto, followed by extraction with dichloromethane three times. Anhydrous magnesium sulfate was added to the organic layer to dry it, and the resultant was filtrated and was then concentrated. The residue was purified using column chromatography (hexane: ethyl acetate=10:1), so as to obtain 6,6'-bis-O-(2-decyldodecanoyl)-2,3,4,2',3',4'-hexabenzyl-α,α'-trehalose (242 mg, 93%) as a diester form in the form of a colorless amorphous solid.

colorless syrup; $[\alpha]_D^{20}$+57.7° (c 0.9 CHCl$_3$); FT IR (neat) 3088, 3064, 3031, 2941, 2862, 1946, 1869, 1804, 1741 cm$^{-1}$; $^1$H NMR (300 MHz in CDCl$_3$) δ0.87 (12H, t, J=6.9 Hz), 1.14-1.32 (64H, m), 1.43 (4H, m), 1.55 (4H, m), 2.32 (2H, m), 3.54 (2H, dd, J=9.0, 3.6 Hz), 3.56 (2H, t, J=9.0 Hz), 4.04 (2H, t, J=9.0 Hz), 4.10 (2H, m), 4.19 (4H, m), 4.53 (2H, d, J=10.8 Hz), 4.67 (2H, d, J=11.7 Hz), 4.72 (2H, d, J=11.7 Hz), 4.85 (2H, d, J=10.8 Hz), 4.87 (2H, d, J=10.8 Hz), 4.99 (2H, d, J=10.8 Hz), 5.18 (2H, d, J=3.6 Hz), 7.22-7.37 (30H, m); $^{13}$C NMR (75 MHz in CDCl$_3$) δ14.13, 22.69, 27.41, 27.45, 29.33, 29.35, 29.51, 29.53, 29.63, 31.90, 32.32, 45.70, 62.07, 69.16, 73.04, 75.28, 75.71, 77.82, 79.68, 81.55, 93.78, 127.38, 127.61, 127.73, 127.86, 127.92, 128.34, 128.43, 137.79, 137.94, 138.59, 176.16.

Production Example A-2

Synthesis of 6,6'-bis-O-(2-octyldecanoyl)-2,3,4,2',3',4'-hexabenzyl-α,α'-trehalose

[Formula 15]

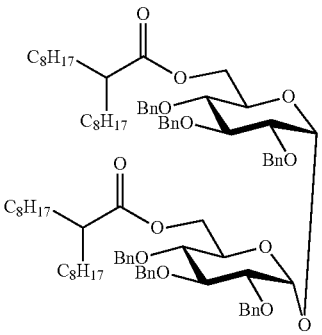

6,6'-Bis-O-(2-octyldecanoyl)-2,3,4,2',3',4'-hexabenzyl-α,α'-trehalose was obtained by the same method as that applied in Production Example A-1, using the 2-octyldecanoic acid obtained by the method described in Production Example C-2 as carboxylic acid.

colorless syrup; $[\alpha]_D^{16}$+62.3° (c 1.0 CHCl$_3$); FT IR (neat) 3088, 3064, 3031, 2927, 2855, 1947, 1868, 1808, 1737 cm$^{-1}$; $^1$H NMR (300 MHz in CDCl$_3$) δ0.85 (6H, t, J=6.9 Hz), 0.86(6H, t, J=6.9 Hz), 1.12-1.34 (48H, m), 1.43 (4H, m), 1.55 (4H, m), 2.32 (2H, m), 3.54 (2H, dd, J=9.6, 3.6 Hz), 3.57 (2H, t, J=9.3 Hz), 4.04 (2H, t, J=9.6 Hz), 4.10 (2H, m), 4.19 (4H, m), 4.53 (2H, d, J=10.5 Hz), 4.67 (2H, d, J=11.7 Hz), 4.71 (2H, d, J=11.7 Hz), 4.85 (2H, d, J=10.5 Hz), 4.87 (2H, d, J=10.5 Hz), 4.99 (2H, d, J=10.5 Hz), 5.18 (2H, d, J=3.6 Hz), 7.22-7.38 (30H, m); $^{13}$CNMR (75 MHz in CDCl$_3$) δ14.12, 22.64, 22.67, 27.40, 27.45, 29.27, 29.45, 29.48, 29.62, 31.83, 31.85, 32.34, 45.71, 62.06, 69.15, 73.04, 75.27, 75.71, 77.24, 77.82, 79.68, 81.55, 93.75, 127.37, 127.61, 127.72, 127.84, 127.91, 127.93, 128.38, 128.44, 137.80, 137.95, 138.59, 176.15; FABMS m/z (%) 1438 (M$^+$+Na); HRMS (FAB$^+$) m/z calcd for C$_{90}$H$_{126}$O$_{13}$Na (M$^+$+Na) 1437.9096, Found 1437.9126.

Production Example A-3

Synthesis of 6,6'-bis-O-(2-nonylundecanoyl)-2,3,4,2',3',4'-hexabenzyl-α,α'-trehalose

[Formula 16]

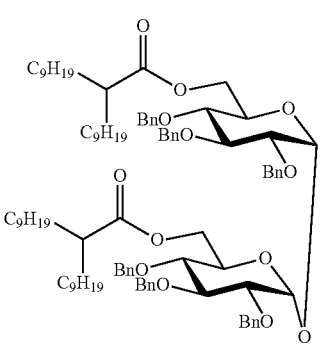

6,6'-Bis-O-(2-nonylundecanoyl)-2,3,4,2',3',4'-hexabenzyl-α,α'-trehalose was obtained by the same method as that applied in Production Example A-1, using the 2-nonylundecanoic acid obtained by the method described in Production Example C-3 as carboxylic acid.

colorless syrup; $[\alpha]_D^{16}$ +64.8° (c 1.0 CHCl$_3$); FT IR (neat) 3088, 3064, 3031, 2926, 2854, 1946, 1871, 1806, 1738 cm$^{-1}$; $^1$H NMR (300 MHz in CDCl$_3$) δ0.86 (6H, t, J=7.0 Hz), 0.87(6H, t, J=7.0 Hz), 1.10-1.34 (56H, m), 1.43 (4H, m), 1.55 (4H, m), 2.32 (2H, m), 3.55 (2H, dd, J=9.6, 3.6 Hz), 3.57 (2H, t, J=9.3 Hz), 4.04 (2H, t, J=9.6 Hz), 4.11 (2H, m), 4.19 (4H, m), 4.53 (2H, d, J=10.2 Hz),4.67 (2H, d, J=11.7 Hz), 4.72 (2H, d, J=11.7 Hz), 4.85 (2H, d, J=10.2 Hz), 4.87 (2H, d, J=10.5 Hz), 4.99 (2H, d, J=10.5 Hz), 5.18 (2H, d, J=3.6 Hz), 7.22-7.37 (30H, m); $^{13}$CNMR (75 MHz in CDCl$_3$) δ14.11, 22.67, 27.39, 27.45, 29.28, 29.30, 29.48, 29.51, 29.56, 29.57, 29.61, 31.85, 31.88, 32.33, 45.69, 62.06, 69.15, 73.03, 75.26, 75.70, 77.23, 77.82, 79.68, 81.54, 93.75, 127.36, 127.59, 127.71, 127.83, 127.90, 127.91, 128.37, 128.42, 137.79, 137.93, 138.58, 176.12; FABMS m/z (%) 1934 (M$^+$+Na); HRMS (FAB$^+$) m/z calcd for C$_{94}$H$_{134}$O$_{13}$Na (M$^+$+Na) 1493.9722, Found 1493.9701.

Production Example A-4

Synthesis of 6,6'-bis-O-(2-undecyltridecanoyl)-2,3,4,2',3',4'-hexabenzyl-α,α'-trehalose

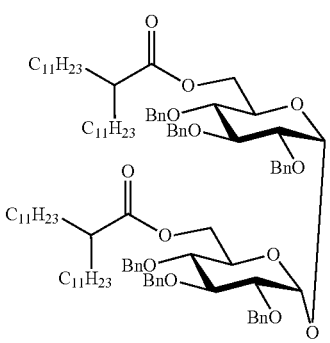

[Formula 17]

6,6'-Bis-O-(2-undecyltridecanoyl)-2,3,4,2',3',4'-hexabenzyl-α,α'-trehalose was obtained by the same method as that applied in Production Example A-1, using the 2-undecyltridecanoic acid obtained by the method described in Production Example C-4 as carboxylic acid.

colorless syrup; $[\alpha]_D^{20}$ +60.0° (c 0.9 CHCl$_3$); FT IR (neat) 3088, 3064, 3031, 2940, 2862, 1946, 1869, 1805, 1740 cm$^{-1}$; $^1$H NMR (300 MHz in CDCl$_3$) δ0.87 (12H, t, J=6.9 Hz), 1.14-1.34 (72H, m), 1.43 (4H, m), 1.56 (4H, m), 2.32 (2H, m), 3.54 (2H, dd, J=10.2, 3.6 Hz), 3.56 (2H, t, J=8.7 Hz), 4.04 (2H, t, J=10.2 Hz), 4.12 (2H, m), 4.19 (4H, m), 4.53 (2H, d, J=10.5 Hz), 4.67 (2H, d, J=12.0 Hz), 4.72 (2H, d, J=12.0 Hz), 4.85 (2H, d, J=10.8 Hz), 4.88 (2H, d, J=10.5 Hz), 4.99 (2H, d, J=10.8 Hz), 5.18 (2H, d, J=3.6 Hz), 7.22-7.37 (30H, m); $^{13}$C NMR (75 MHz in CDCl$_3$) δ14.12, 22.67, 27.40, 27.44, 29.34, 29.50, 29.52, 29.62, 31.90, 32.30, 45.68, 62.05, 69.14, 73.03, 75.25, 75.69, 77.80, 79.66, 81.52, 93.76, 127.35, 127.58, 127.70, 127.82, 127.90, 128.36, 128.40, 137.76, 137.92, 138.57, 176.12.

Production Example A-5

Synthesis of 6,6'-bis-O-(2-dodecyltetradecanoyl)-2,3,4,2',3',4'-hexabenzyl-α,α'-trehalose

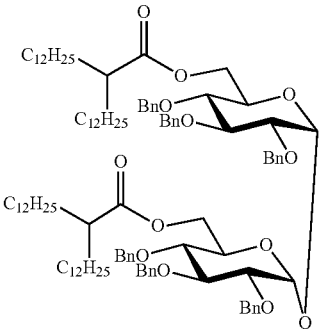

[Formula 18]

6,6'-Bis-O-(2-dodecyltetradecanoyl)-2,3,4,2',3',4'-hexabenzyl-α,α'-trehalose was obtained by the same method as that applied in Production Example A-1, using the 2-dodecyltetradecanoic acid obtained by the method described in Production Example C-5 as carboxylic acid.

colorless syrup; $[\alpha]_D^{20}$ +60.8° (c 1.0 CHCl$_3$); FT IR (neat) 3088, 3064, 3031, 2940, 2862, 1946, 1869, 1804, 1739 cm$^{-1}$; $^1$H NMR (300 MHz in CDCl$_3$) δ0.88 (12H, t, J=6.9 Hz), 1.14-1.34 (80H, m), 1.43 (4H, m), 1.56 (4H, m), 2.32 (2H, m), 3.54 (2H, dd, J=9.6, 3.6 Hz), 3.57 (2H, t, J=8.4 Hz), 4.04 (2H, t, J=9.6 Hz), 4.12 (2H, m), 4.19 (4H, m), 4.53 (2H, d, J=10.5 Hz), 4.67 (2H, d, J=12.0 Hz), 4.72 (2H, d, J=12.0 Hz), 4.86 (2H, d, J=10.8 Hz), 4.87 (2H, d, J=10.5 Hz), 4.99 (2H, d, J=10.8 Hz), 5.18 (2H, d, J=3.6 Hz), 7.24-7.37 (30H, m); $^{13}$C NMR (75 MHz in CDCl$_3$) δ14.12, 22.69, 27.41, 27.46, 29.36, 29.53, 29.66, 31.92, 32.32, 45.70, 62.09, 69.19, 73.07, 75.27, 75.71, 77.86, 79.72, 81.56, 93.78, 127.71, 127.62, 127.74, 127.86, 127.94, 128.40, 128.45, 137.83, 138.00, 138.64, 176.17.

Production Example A-6

Synthesis of 6,6'-bis-O-(2-tridecylpentadecanoyl)-2,3,4,2',3',4'-hexabenzyl-α,α'-trehalose

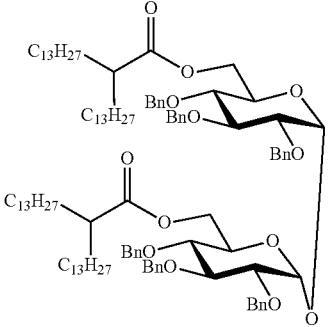

[Formula 19]

6,6'-Bis-O-(2-tridecylpentadecanoyl)-2,3,4,2',3',4'-hexabenzyl-α,α'-trehalose was obtained by the same method as that applied in Production Example A-1, using the 2-tridecylpentadecanoic acid obtained by the method described in Production Example C-6 as carboxylic acid.

colorless syrup; $[\alpha]_D^{20}$+50.2° (c 1.1 CHCl$_3$); FT IR (neat) 3088, 3064, 3031, 2929, 2855, 1945, 1868, 1804, 1739 cm$^{-1}$; $^1$H NMR (300 MHz in CDCl$_3$) δ0.88 (12H, t, J=6.6 Hz), 1.10-1.34 (88H, m), 1.44 (4H, m), 1.56 (4H, m), 2.32 (2H, m), 3.54 (2H, dd, J=9.8, 3.6 Hz), 3.58 (2H, t, J=9.8 Hz), 4.04 (2H, t, J=9.8 Hz), 4.13 (2H, m), 4.19 (4H, m), 4.53 (2H, d, J=10.8 Hz), 4.66 (2H, d, J=12.0 Hz), 4.73 (2H, d, J=12.0 Hz), 4.85 (2H, d, J=11.0 Hz), 4.87 (2H, d, J=10.8 Hz), 4.99 (2H, d, J=11.0 Hz), 5.18 (2H, d, J=3.6 Hz), 7.20-7.38 (30H, m); $^{13}$C NMR (75 MHz in CDCl$_3$) δ14.11, 22.70, 27.42, 27.46, 29.37, 29.54, 29.66, 31.93, 32.33, 45.72, 62.12, 69.23, 73.10, 75.26, 75.69, 77.23, 77.67, 77.91, 79.77, 81.58, 93.77, 127.42, 127.61, 127.74, 127.85, 127.94, 128.40, 128.44, 128.46, 137.86, 138.05, 138.68, 176.15.

Production Example A-7

Synthesis of 6,6'-bis-O-(2-pentadecylheptadecanoyl)-2,3,4,2',3',4'-hexabenzyl-α,α'-trehalose

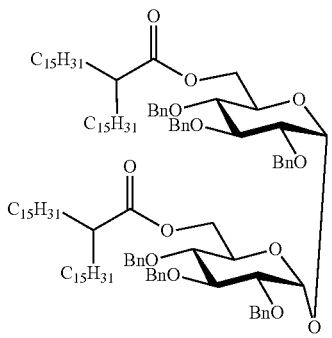

[Formula 20]

6,6'-Bis-O-(2-pentadecylheptadecanoyl)-2,3,4,2',3',4'-hexabenzyl-α,α'-trehalose was obtained by the same method as that applied in Production Example A-1, using the 2-pentadecylheptadecanoic acid obtained by the method described in Production Example C-8 as carboxylic acid.

colorless syrup; $[\alpha]_D^{20}$+44.3° (c 1.0 CHCl$_3$); FT IR (neat) 3088, 3064, 3031, 2941, 2861, 1945, 1868, 1812, 1739 cm$^{-1}$; $^1$H NMR (300 MHz in CDCl$_3$) δ0.88 (12H, t, J=7.2 Hz), 1.12-1.38 (104H, m), 1.43 (4H, m), 1.56 (4H, m), 2.32 (2H, m), 3.54 (2H, dd, J=9.6, 3.6 Hz), 3.57 (2H, t, J=8.7 Hz), 4.04 (2H, t, J=9.6 Hz), 4.12 (2H, m), 4.20 (4H, m), 4.53 (2H, d, J=10.5 Hz), 4.67 (2H, d, J=12.0 Hz), 4.72 (2H, d, J=12.0 Hz), 4.86 (2H, d, J=10.8 Hz), 4.87 (2H, d, J=10.8 Hz), 4.99 (2H, d, J=10.5 Hz), 5.18 (2H, d, J=3.6 Hz), 7.22-7.37 (30H, m); $^{13}$C NMR (75 MHz in CDCl$_3$) δ14.14, 22.70, 27.25, 27.42, 27.45, 29.38, 29.55, 29.68, 29.72, 31.94, 32.32, 45.70, 62.07, 69.16, 73.05, 75.29, 75.72, 77.82, 79.68, 81.55, 93.78, 127.40, 127.62, 127.75, 127.95, 128.41, 128.45, 137.81, 137.95, 138.61, 176.19.

Production Example A-8

Synthesis of 6,6'-bis-O-(2-hexadecyloctadecanoyl)-2,3,4,2',3',4'-hexabenzyl-α,α'-trehalose

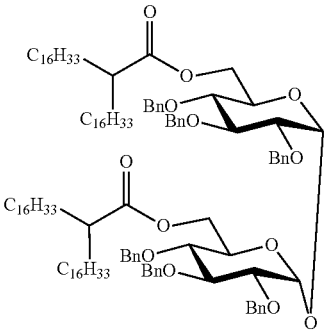

[Formula 21]

6,6'-Bis-O-(2-hexadecyloctadecanoyl)-2,3,4,2',3',4'-hexabenzyl-α,α'-trehalose was obtained by the same method as that applied in Production Example A-1, using the 2-hexadecyloctadecanoic acid obtained by the method described in Production Example C-9 as carboxylic acid.

colorless syrup; $[\alpha]_D^{20}$+48.8° (c 1.0 CHCl$_3$); FT IR (neat) 3088, 3064, 3031, 2938, 2857, 1944, 1869, 1808, 1739 cm$^{-1}$; $^1$H NMR (300 MHz in CDCl$_3$) δ0.88 (12H, t, J=6.9 Hz), 1.10-1.36 (112H, m), 1.43 (4H, m), 1.56 (4H, m), 2.32 (2H, m), 3.55 (2H, dd, J=9.3, 3.6 Hz), 3.57 (2H, t, J=9.0 Hz), 4.04 (2H, t, J=9.3 Hz), 4.11 (2H, m), 4.19 (4H, m), 4.53 (2H, d, J=10.5 Hz), 4.67 (2H, d, J=12.0 Hz), 4.72 (2H, d, J=12.0 Hz), 4.86 (2H, d, J=10.8 Hz), 4.87 (2H, d, J=10.5 Hz), 4.99 (2H, d, J=10.8 Hz), 5.18 (2H, d, J=3.6 Hz), 7.22-7.37 (30H, m); $^{13}$C NMR (75 MHz in CDCl$_3$) δ14.15, 22.71, 27.43, 29.39, 29.56, 29.69, 29.73, 31.94, 32.31, 45.70, 62.08, 69.17, 73.05, 75.31, 75.74, 77.83, 79.68, 81.56, 93.81, 127.41, 127.64, 127.76, 127.96, 128.42, 128.47, 137.83, 138.00, 138.62, 176.22.

Example 1

Production Example α-1

Synthesis of 6,6'-bis-O-(2-decyldodecanoyl)-α,α'-trehalose

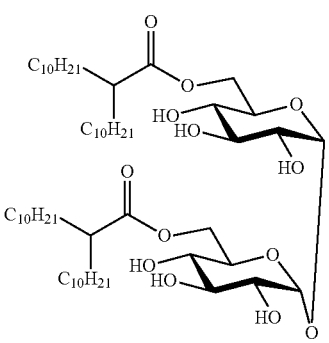

[Formula 22]

The 6,6'-bis-O-(2-decyldodecanoyl)-2,3,4,2',3',4'-hexabenzyl-α,α'-trehalose (200 mg, 131 μmol) obtained by the method described in Production Example A-1 was dissolved in a mixed solvent (4 ml) of chloroform:methanol:acetic acid (1:1:0.05), and palladium hydroxide (20 w/w %, 8 mg, 11.4 μmol) was then added to the obtained solution. The obtained mixture was stirred under 1 atmospheric pressure of hydrogen for 6 hours. Thereafter, the reaction mixture was filtrated and was then concentrated, and the residue was purified using column chromatography (dichloromethane:methanol=10:1), so as to obtain 6,6'-bis-O-(2-decyldodecanoyl)-α,α'-trehalose (125 mg, 97%) in the form of a colorless amorphous solid.

colorless syrup; $[\alpha]_D^{20}$+61.8° (c 1.0 CHCl$_3$); FT IR (neat) 3358, 2940, 2861, 1746 cm$^{-1}$; $^1$H NMR (300 MHz in C$_5$D$_5$N) δ0.88 (12H, t, J=6.9 Hz), 1.25 (56H, m), 1.45 (8H, m), 1.58 (4H, m), 1.83 (4H, m), 2.58 (2H, m), 4.18 (2H, t, J=9.3 Hz), 4.29 (2H, dd, J=9.3, 3.6 Hz), 4.73 (2H, t, J=9.3 Hz), 4.88 (2H, dd, J=11.7, 5.1 Hz), 5.07 (4H, m), 5.87 (2H, d, J=3.6 Hz); $^{13}$C NMR (75 MHz in C$_5$D$_5$N) δ14.29, 22.95, 27.75, 27.80, 29.62, 29.80, 29.90, 29.95, 32.14, 32.82, 46.16, 63.93, 71.54, 71.94, 73.31, 74.81, 95.69, 176.26; FABMS m/z (%) 1010 (M$^+$+Na); HRMS (FAB$^+$) m/z calcd for C$_{56}$H$_{106}$O$_{13}$Na (M$^+$+Na) 1009.7532, Found 1009.7498.

Example 2

Production Example α-2

Synthesis of 6,6'-bis-O-(2-octyldecanoyl)-α,α'-trehalose

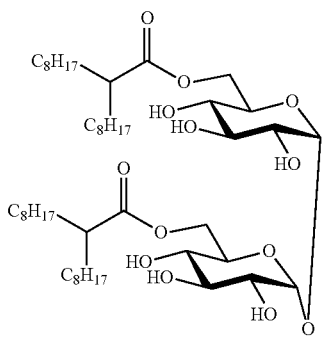

[Formula 23]

6,6'-Bis-O-(2-octyldecanoyl)-α,α'-trehalose was obtained by the same method as that applied in Production Example α-1, using the 6,6'-bis-O-(2-octyldecanoyl)-2,3,4,2',3',4'-hexabenzyl-α,α'-trehalose obtained by the method described in Production Example A-2 as a raw material compound.

colorless syrup; $[\alpha]_D^{14}$+70.2° (c 0.6 CHCl$_3$); FT IR (neat) 3300, 2929, 2856, 1743 cm$^{-1}$; $^1$H NMR (300 MHz in C$_5$D$_5$N) δ0.86 (12H, t, J=6.9 Hz), 1.21 (40H, m), 1.46 (8H, m), 1.57 (4H, m), 1.80 (4H, m), 2.56 (2H, m), 4.19 (2H, t, J=9.6 Hz), 4.29 (2H, dd, J=9.6, 3.6 Hz), 4.74 (2H, t, J=9.6 Hz), 4.88 (2H, dd, J=12.0, 4.8 Hz), 5.08 (4H, m), 5.87 (2H, d, J=3.6 Hz); $^{13}$C NMR (75 MHz in C$_5$D$_5$N) δ13.69, 22.32, 27.12, 27.19, 28.96, 29.11, 29.33, 31.47, 32.23, 45.55, 63.25, 70.94, 71.30, 72.69, 74.18, 95.14, 175.68; FABMS m/z (%) 898 (M$^+$+Na); HRMS (FAB$^+$) m/z calcd for C$_{48}$H$_{90}$O$_{13}$Na (M$^+$+Na) 897.6279, Found 897.6249.

Example 3

Production Example α-3

Synthesis of 6,6'-bis-O-(2-nonylundecanoyl)-α,α'-trehalose

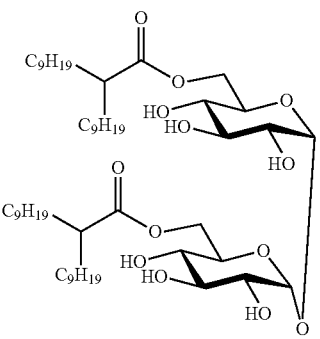

[Formula 24]

6,6'-Bis-O-(2-nonylundecanoyl)-α,α'-trehalose was obtained by the same method as that applied in Production Example α-1, using the 6,6'-bis-O-(2-nonylundecanoyl)-2,3,4,2',3',4'-hexabenzyl-α,α'-trehalose obtained by the method described in Production Example A-3 as a raw material compound.

colorless syrup; $[\alpha]_D^{14}$+64.9° (c 0.6 CHCl$_3$); FT IR (neat) 3306, 2928, 2855, 1742 cm$^{-1}$; $^1$H NMR (300 MHz in C$_5$D$_5$N) δ0.87 (12H, t, J=6.9 Hz), 1.22 (48H, m), 1.42 (8H, m), 1.54 (4H, m), 1.79 (4H, m), 2.56 (2H, m), 4.19 (2H, t, J=9.0 Hz), 4.39 (2H, dd, J=9.0, 3.6 Hz), 4.74 (2H, t, J=9.0 Hz), 4.88 (2H, dd, J=11.7, 4.8 Hz), 5.08 (4H, m), 5.88 (2H, d, J=3.6 Hz); $^{13}$C NMR (75 MHz in C$_5$D$_5$N) δ13.69, 22.32, 27.14, 27.20, 28.97, 29.17, 29.27, 29.34, 31.51, 32.22, 45.55, 63.28, 70.94, 71.31, 72.69, 74.18, 95.13, 175.67; FABMS m/z (%) 954 (M$^+$+Na); HRMS (FAB$^+$) m/z calcd for C$_{52}$H$_{98}$O$_{13}$Na (M$^+$+Na) 953.6905, Found 953.6862.

Example 4

Production Example α-4

Synthesis of 6,6'-bis-O-(2-undecyltridecanoyl)-α,α'-trehalose

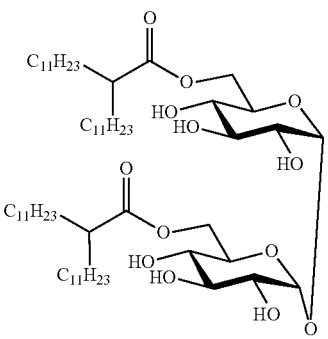

[Formula 25]

6,6'-Bis-O-(2-undecyltridecanoyl)-α,α'-trehalose was obtained by the same method as that applied in Production Example α-1, using the 6,6'-bis-O-(2-undecyltridecanoyl)-2,3,4,2',3',4'-hexabenzyl-α,α'-trehalose obtained by the method described in Production Example A-4 as a raw material compound.

colorless syrup; $[\alpha]_D^{14}$ +58.5° (c 1.0 CHCl$_3$); FT IR (neat) 3297, 2934, 2856, 1742 cm$^{-1}$; $^1$H NMR (300 MHz in C$_5$D$_5$N) δ0.88 (12H, t, J=6.6 Hz), 1.26 (64H, m),1.45 (8H, m), 1.58 (4H, m), 1.82 (4H, m), 2.58 (2H, m), 4.18 (2H, t, J=9.0 Hz), 4.29 (2H, dd, J=9.0, 3.6 Hz), 4.73 (2H, t, J=9.0 Hz), 4.88 (2H, dd, J=11.7, 5.1 Hz), 5.07 (4H, m), 5.88 (2H, d, J=3.6 Hz); $^{13}$C NMR (75 MHz in C$_5$D$_5$N) δ14.29, 22.94, 27.75, 27.80, 29.63, 29.81, 29.96, 32.14, 32.81, 46.15, 63.93, 71.54, 71.94, 73.31, 74.81, 95.67, 176.25; FABMS m/z (%) 1066 (M$^+$+Na); HRMS (FAB$^+$) m/z calcd for C$_{60}$H$_{114}$O$_{13}$Na (M$^+$+Na) 1065.8157, Found 1065.8160.

Example 5

Production Example α-5

Synthesis of 6,6'-bis-O-(2-dodecyltetradecanoyl)-α,α'-trehalose

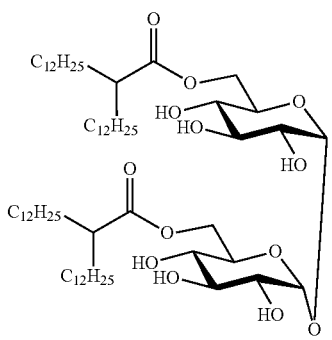

[Formula 26]

6,6'-Bis-O-(2-dodecyltetradecanoyl)-α,α'-trehalose was obtained by the same method as that applied in Production Example α-1, using the 6,6'-bis-O-(2-dodecyltetradecanoyl)-2,3,4,2',3',4'-hexabenzyl-α,α'-trehalose obtained by the method described in Production Example A-5 as a raw material compound.

colorless syrup; $[\alpha]_D^{14}$ +54.6° (c 1.0 CHCl$_3$); FT IR (neat) 3310, 2937, 2857, 1742 cm$^{-1}$; $^1$H NMR (300 MHz in C$_5$D$_5$N) δ0.88 (12H, t, J=6.9 Hz), 1.28 (72H, m),1.46 (8H, m), 1.58 (4H, m), 1.82 (4H, m), 2.59 (2H, m), 4.18 (2H, t, J=9.0 Hz), 4.29 (2H, dd, J=9.0, 3.6 Hz), 4.73 (2H, t, J=9.0 Hz), 4.88 (2H, dd, J=11.7, 5.1 Hz), 5.08 (4H, m), 5.87 (2H, d, J=3.6 Hz); $^{13}$C NMR (75 MHz in C$_5$D$_5$N) δ14.30, 22.97, 27.77, 27.82, 29.66, 29.83, 29.99, 32.17, 32.82, 46.16, 63.94, 71.53, 71.95, 73.31, 74.80, 95.66, 176.24; FABMS m/z (%) 1122 (M$^+$+Na); HRMS (FAB$^+$) m/z calcd for C$_{64}$H$_{122}$O$_{13}$Na (M$^+$+Na) 1121.8784, Found 1121.8831.

Example 6

Production Example α-6

Synthesis of 6,6'-bis-O-(2-tridecylpentadecanoyl)-α,α'-trehalose

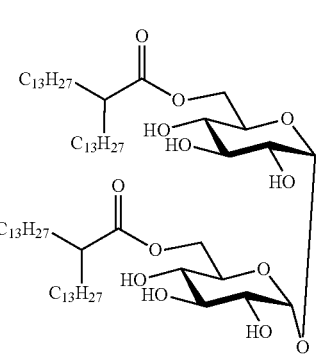

[Formula 27]

6,6'-Bis-O-(2-tridecylpentadecanoyl)-α,α'-trehalose was obtained by the same method as that applied in Production Example α-1, using the 6,6'-bis-O-(2-tridecylpentadecanoyl)-2,3,4,2',3',4'-hexabenzyl-α,α'-trehalose obtained by the method described in Production Example A-6 as a raw material compound.

colorless syrup; $[\alpha]_D^{19}$ +52.7° (c 0.6 CHCl$_3$); FT IR (neat) 3313, 2927, 2854, 1741 cm$^{-1}$; $^1$H NMR (300 MHz in C$_5$D$_5$N) δ0.88 (12H, t, J=6.9 Hz), 1.29 (80H, m),1.46 (8H, m), 1.58 (4H, m), 1.83 (4H, m), 2.59 (2H, m), 4.19 (2H, t, J=9.6 Hz), 4.29 (2H, dd, J=9.6, 3.6 Hz), 4.74 (2H, t, J=9.6 Hz), 4.89 (2H, dd, J=11.7, 5.1 Hz), 5.08 (4H, m), 5.88 (2H, d, J=3.6 Hz); $^{13}$C NMR (75 MHz in C$_5$D$_5$N) δ14.28, 22.94, 27.75, 27.80, 29.63, 29.82, 29.98, 32.14, 32.80, 46.14, 63.92, 71.53, 71.94, 73.30, 74.79, 95.66, 176.21; FABMS m/z (%) 1178 (M$^+$+Na); HRMS (FAB$^+$) m/z calcd for C$_{68}$H$_{130}$O$_{13}$Na (M$^+$+Na) 1177.9409, Found 1177.9404.

Example 7

Production Example α-7

Synthesis of 6,6'-bis-O-(2-pentadecylheptadecanoyl)-α,α'-trehalose

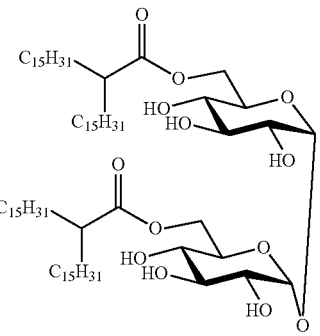

[Formula 28]

6,6'-Bis-O-(2-pentadecylheptadecanoyl)-α,α'-trehalose was obtained by the same method as that applied in Production Example α-1, using the 6,6'-bis-O-(2-pentadecylheptadecanoyl)-2,3,4,2',3',4'-hexabenzyl-α,α'-trehalose obtained by the method described in Production Example A-7 as a raw material compound.

colorless syrup; $[\alpha]_D^{19}$+44.8° (c 0.5 CHCl$_3$); FT IR (neat) 3330, 2925, 2853, 1741 cm$^{-1}$; $^1$H NMR (300 MHz in C$_5$D$_5$N) δ0.87 (12H, t, J=7.2 Hz), 1.31 (96H, m), 1.47 (8H, m), 1.58 (4H, m), 1.83 (4H, m), 2.59 (2H, m), 4.19 (2H, t, J=9.0 Hz), 4.29 (2H, dd, J=9.0, 3.6 Hz), 4.74 (2H, t, J=9.0 Hz), 4.88 (2H, dd, J=11.4, 4.8 Hz), 5.08 (4H, m), 5.87 (2H, d, J=3.6 Hz); $^{13}$C NMR (75 MHz in C$_5$D$_5$N) δ14.23, 22.89, 27.73, 27.79, 29.58, 29.80, 29.91, 29.97, 32.09, 32.78, 46.13, 63.92, 71.55, 71.95, 73.32, 74.80, 95.67, 176.21; FABMS m/z (%) 1290 (M$^+$+Na); HRMS (FAB$^+$) m/z calcd for C$_{76}$H$_{146}$O$_{13}$Na (M$^+$+Na) 1290.0661, Found 1290.0677.

Example 8

Production Example α-8

Synthesis of 6,6'-bis-O-(2-hexadecyloctadecanoyl)-α,α'-trehalose

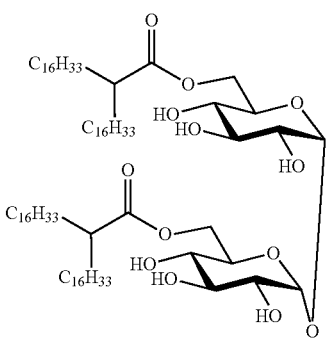

[Formula 29]

6,6'-Bis-O-(2-hexadecyloctadecanoyl)-α,α'-trehalose was obtained by the same method as that applied in Production Example α-1, using the 6,6'-bis-O-(2-hexadecyloctadecanoyl)-2,3,4,2',3',4'-hexabenzyl-α,α'-trehalose obtained by the method described in Production Example A-8 as a raw material compound.

colorless syrup; $[\alpha]_D^{17}$+45.1° (c 0.5 CHCl$_3$); FT IR (neat) 3308, 2937, 2856, 1741 cm$^{-1}$; $^1$H NMR (300 MHz in C$_5$D$_5$N) δ0.87 (12H, t, J=6.9 Hz), 1.31 (104H, m), 1.46 (8H, m), 1.57 (4H, m), 1.80 (4H, m), 2.56 (2H, m), 4.19 (2H, t, J=9.3 Hz), 4.29 (2H, dd, J=9.3, 3.6 Hz), 4.74 (2H, t, J=9.3 Hz), 4.88 (2H, dd, J=11.4, 4.8 Hz), 5.08 (4H, m), 5.87 (2H, d, J=3.6 Hz); $^{13}$C NMR (75 MHz in C$_5$D$_5$N) δ14.25, 22.90, 27.75, 27.80, 29.60, 29.82, 29.91, 29.99, 32.10, 32.80, 46.14, 63.91, 71.55, 71.95, 73.32, 74.80, 95.66, 176.24; FABMS m/z (%) 1346 (M$^+$+Na); HRMS (FAB$^+$) m/z calcd for C$_{80}$H$_{154}$O$_{13}$Na (M$^+$+Na) 1346.1288, Found 1346.1287.

Production Example B-1

Synthesis of 6,6'-bis-O-(3-nonyldodecanoyl)-2,3,4,2',3',4'-hexabenzyl-α,α'-trehalose

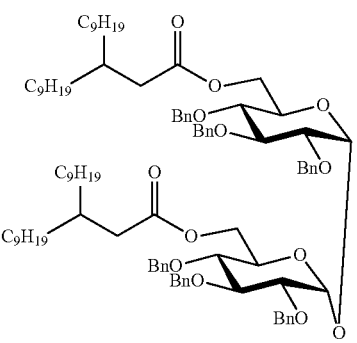

[Formula 30]

The carboxylic acid (3-nonyldodecanoic acid) (236 mg, 724 μmol) obtained by the method described in Production Example D-1 and a trehalose derivative (2,3,4,2',3',4'-hexabenzoxy-α,α'-trehalose) (256 mg, 290 μmol) were dissolved in an anhydrous dichloromethane solution (10 ml). Thereafter, powdered molecular sieves 4A (1 g), 4-dimethylaminopyridine (35.4 mg, 290 μmol), 1-ethyl-3-(3-dimethylaminopropyl)carbodiimide hydrochloride [hereinafter abbreviated as EDCI] (222 mg, 1.16 mmol) were successively added to the solution, and the mixed solution was then heated to reflux for 10 hours. Thereafter, the reaction solution was filtrated with Celite-535, and a saturated saline solution was then added thereto, followed by extraction with dichloromethane two times. Anhydrous magnesium sulfate was added to the organic layer to dry it, and the resultant was filtrated and was then concentrated. The residue was purified using column chromatography (hexane:ethyl acetate=15:1), so as to obtain 6,6'-bis-O-(3-nonyldodecanoyl)-2,3,4,2',3',4'-hexabenzyl-α,α'-trehalose (350 mg, 80%) as a diester form in the form of a colorless amorphous solid.

colorless syrup; $[\alpha]_D^{21}$+65.3° (c 1.0 CHCl$_3$); FT IR (neat) 3088, 3063, 3031, 2925, 2853, 1944, 1871, 1806, 1739 cm$^{-1}$; $^1$H NMR (300 MHz in CDCl$_3$) δ0.87 (12H, t, J=5.1 Hz), 1.20 (64H, m), 1.81 (2H, m), 2.20 (4H, d, J=6.9 Hz), 3.54 (2H, t, J=9.3 Hz), 3.56 (2H, m), 4.04 (2H, t, J=9.3 Hz), 4.09 (4H, m), 4.23 (2H, m), 4.51 (2H, d, J=10.5 Hz), 4.67 (2H, d, J=12.0 Hz), 5.17 (2H, d, J=3.6 Hz), 7.23-7.37 (30H, m); $^{13}$C NMR (75 MHz in CDCl$_3$) δ14.13, 22.68, 26.51, 29.33, 29.56, 29.64, 29.92, 31.89, 33.65, 33.76, 34.89, 39.08, 62.35, 69.12, 72.94, 75.30, 75.70, 77.60, 79.38, 81.56, 94.02, 127.44, 127.63, 127.78, 127.92, 128.09, 128.41, 128.47, 137.78, 137.84, 138.60, 173.24; FABMS m/z (%) 1522 (M$^+$+Na); HRMS (FAB$^+$) m/z calcd for C$_{96}$H$_{138}$O$_{13}$Na (M$^+$+Na) 1522.0036, Found 1522.0020.

Production Example B-2

Synthesis of 6,6'-bis-O-(3-octylundecanoyl)-2,3,4,2',3',4'-hexabenzyl-α,α'-trehalose

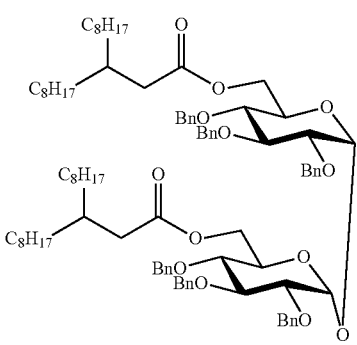

[Formula 31]

6,6'-Bis-O-(3-octylundecanoyl)-2,3,4,2',3',4'-hexabenzyl-α,α'-trehalose was obtained by the same method as that applied in Production Example B-1, using the 3-octylundecanoic acid obtained by the method described in Production Example D-2 as carboxylic acid.

colorless syrup; $[\alpha]_D^{20}$ +41.8° (c 2.0 CHCl$_3$); FT IR (neat) 3088, 3064, 3031, 2932, 2855, 1947, 1867, 1806, 1739 cm$^{-1}$; $^1$H NMR (300 MHz in CDCl$_3$) δ0.86 (6H, t, J=6.9 Hz), 80.87 (6H, t, J=6.9 Hz), 1.20 (56H, m), 1.81 (2H, m), 2.20 (4H, d, J=6.9 Hz), 3.54 (2H, t, J=8.4 Hz), 3.56 (2H, m), 4.04 (2H, t, J=9.3 Hz), 4.09 (4H, m), 4.23 (2H, m), 4.51 (2H, d, J=10.5 Hz), 4.67 (2H, d, J=12.0 Hz), 4.72 (2H, d, J=12.0 Hz), 4.86 (4H, d, J=10.5 Hz), 5.00 (2H, d, J=10.5 Hz), 5.17 (2H, d, J=3.6 Hz), 7.23-7.37 (30H, m); $^{13}$C NMR (75 MHz in CDCl$_3$) δ14.14, 22.69, 26.52, 29.32, 29.61, 29.94, 31.89, 33.69, 33.80, 34.91, 39.10, 62.38, 69.14, 72.96, 75.29, 75.70, 77.62, 79.40, 81.58, 93.95, 94.04, 127.44, 127.62, 127.77, 127.91, 128.07, 128.41, 128.46, 137.78, 137.85, 138.59, 173.23; FABMS m/z (%) 1466 (M$^+$+Na); HRMS (FAB$^+$) m/z calcd for C$_{92}$H$_{130}$O$_{13}$Na (M$^+$+Na) 1465.9409, Found 1465.9392.

Production Example B-3

Synthesis of 6,6'-bis-O-(3-decyltridecanoyl)-2,3,4,2',3',4'-hexabenzyl-α,α'-trehalose

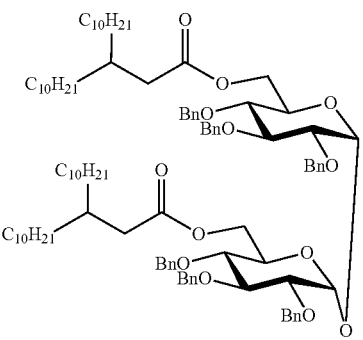

[Formula 32]

6,6'-Bis-O-(3-decyltridecanoyl)-2,3,4,2',3',4'-hexabenzyl-α,α'-trehalose was obtained by the same method as that applied in Production Example B-1, using the 3-decyltridecanoic acid obtained by the method described in Production Example D-3 as carboxylic acid.

colorless syrup; $[\alpha]_D^{20}$ +53.6° (c 1.0 CHCl$_3$); FT IR (neat) 3088, 3063, 3030, 2926, 2854, 1946, 1874, 1804, 1739 cm$^{-1}$; $^1$H NMR (300 MHz in CDCl$_3$) δ80.87 (12H, t, J=6.9 Hz), 1.21 (72H, m), 1.81 (2H, m), 2.19 (4H, d, J=6.9 Hz), 3.54 (2H,t, J=8.4 Hz), 3.56 (2H, m), 4.04 (2H, t, J=8.4 Hz), 4.11 (4H, m), 4.21 (2H,m), 4.51 (2H, d, J=10.5 Hz), 4.67 (2H, d, J=12.0 Hz), 4.72 (2H, d, J=12.0 Hz), 4.86 (4H, d, J=10.5 Hz), 5.00 (2H, d, J=10.5 Hz), 5.17 (2H, d, J=3.6 Hz), 7.23-7.36 (30H, m); $^{13}$C NMR (75 MHz in CDCl$_3$) δ14.14, 22.70, 26.51, 29.36, 29.66, 29.95, 31.93, 33.67, 77.23, 77.62, 79.40, 81.58, 94.04, 127.46, 127.65, 127.80, 127.93, 128.10, 128.43, 128.49, 137.80, 137.87, 138.62, 173.27; FABMS m/z (%) 1579 (M$^+$+H+Na); HRMS (FAB$^+$) m/z calcd for C$_{100}$H$_{147}$O$_{13}$Na (M$^+$+H+Na) 1579.0787, Found 1579.0763.

Production Example B-4

Synthesis of 6,6'-bis-O-(3-undecyltetradecanoyl)-2,3,4,2',3',4'-hexabenzyl-α,α'-trehalose

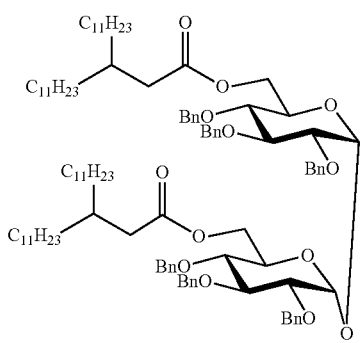

[Formula 33]

6,6'-Bis-O-(3-undecyltetradecanoyl)-2,3,4,2',3',4'-hexabenzyl-α,α'-trehalose was obtained by the same method as that applied in Production Example B-1, using the 3-undecyltetradecanoic acid obtained by the method described in Production Example D-4 as carboxylic acid.

colorless syrup; $[\alpha]_D^{20}$ +58.1° (c 1.0 CHCl$_3$); FT IR (neat) 3088, 3064, 3031, 2926, 2854, 1946, 1867, 1806, 1739 cm$^{-1}$; $^1$H NMR (300 MHz in CDCl$_3$) δ0.88 (12H, t, J=7.2 Hz), 1.21 (80H, m), 1.81 (2H, m), 2.19 (4H, d, J=6.9 Hz), 3.54 (2H,t, J=8.4 Hz), 3.55 (2H, m), 4.04 (2H, t, J=6.9 Hz), 4.10 (4H, m), 4.20 (2H,m), 4.51 (2H, d, J=10.5 Hz), 4.67 (2H, d, J=12.0 Hz), 4.71 (2H, d, J=12.0 Hz), 4.86 (4H, d, J=10.5 Hz), 5.00 (2H, d, J=10.5 Hz), 5.17 (2H, d, J=3.6 Hz), 7.19-7.36 (30H, m); $^{13}$C NMR (75 MHz in CDCl$_3$) δ14.14, 22.71, 26.53, 29.38, 29.67, 29.95, 31.93, 33.68, 33.79, 34.91, 39.10, 62.37, 69.14, 72.96, 75.31, 75.71, 77.63, 79.40, 81.58, 94.04, 127.46, 127.64, 127.80, 127.93, 128.10, 128.43, 128.49, 137.80, 137.87, 138.62, 173.27; FABMS m/z (%) 1635 (M$^+$+Na); HRMS (FAB$^+$) m/z calcd for C$_{104}$H$_{154}$O$_{13}$Na (M$^+$+Na) 1634.1288, Found 1634.1298.

Production Example B-5

Synthesis of 6,6'-bis-O-(3-dodecylpentadecanoyl)-2,3,4,2',3',4'-hexabenzyl-α,α'-trehalose

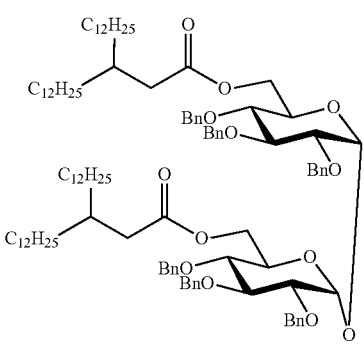

[Formula 34]

6,6'-Bis-O-(3-dodecylpentadecanoyl)-2,3,4,2',3',4'-hexabenzyl -60 ,α'-trehalose was obtained by the same method as that applied in Production Example B-1, using the 3-dodecylpentadecanoic acid obtained by the method described in Production Example D-5 as carboxylic acid.

colorless syrup; $[\alpha]_D^{20}$+68.9° (c 0.9 CHCl$_3$); FT IR (neat) 3088, 3063, 3031, 2925, 2853, 1944, 1867, 1806, 1739 cm$^{-1}$; $^1$H NMR (300 MHz in CDCl$_3$) δ0.88 (12H, t, J=6.9 Hz), 1.21 (88H, m), 1.81 (2H, m), 2.20 (4H, d, J=6.9 Hz), 3.54 (2H,t, J=8.7 Hz), 3.57 (4H, m), 4.05 (2H, t, J=8.7 Hz), 4.05 (2H, t, J=8.7 Hz), 4.11 (2H, m), 4.21 (2H, m), 4.52 (2H, d, J=10.5 Hz), 4.67 (2H, d, J=12.3 Hz), 4.72 (2H, d, J=12.3 Hz), 4.86 (4H, d, J=10.5 Hz), 5.01 (2H, d, J=10.5 Hz), 5.18 (2H, d, J=3.3 Hz), 7.21-7.37 (30H, m); $^{13}$C NMR (75 MHz in CDCl$_3$) δ14.14, 22.70, 26.53, 29.38, 29.67, 29.95, 31.92, 33.67, 33.78, 34.91, 39.10, 62.37, 69.14, 72.96, 75.30, 75.71, 77.63, 79.40, 81.57, 94.03, 127.45, 127.63, 127.79, 127.93, 128.09, 128.42, 128.48, 137.79, 137.87, 138.62, 173.26; FABMS m/z (%) 1691 (M$^+$+H+Na); HRMS (FAB$^+$) m/z calcd for C$_{108}$H$_{163}$O$_{13}$Na (M$^+$+H+Na) 1691.1993, Found 1691.1992.

Production Example B-6

Synthesis of 6,6'-bis-O-(3-tridecylhexadecanoyl)-2,3,4,2',3',4'-hexabenzyl-α,α'-trehalose

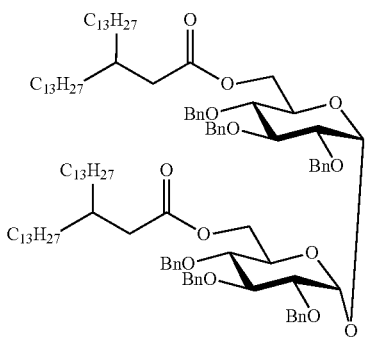

[Formula 35]

6,6'-Bis-O-(3-tridecylhexadecanoyl)-2,3,4,2',3',4'-hexabenzyl-α,α'-trehalose was obtained by the same method as that applied in Production Example B-1, using commercially available 3-tridecylhexadecanoic acid (manufactured by Wako Pure Chemical Industries, Ltd.) as carboxylic acid.

colorless syrup; $[\alpha]_D^{20}$+49.5 (c 0.9 CHCl$_3$); FT IR (neat) 3088, 3064, 3031, 2925, 2853, 1944, 1871, 1806, 1739 cm$^{-1}$; $^1$H NMR (300 MHz in CDCl$_3$) δ0.88 (12H, t, J=6.9 Hz), 1.23 (96H, m), 1.81 (2H, m), 2.20 (4H, d, J=6.9 Hz), 3.54 (4H,m), 4.04 (2H, t, J=9.3 Hz), 4.11 (4H, m), 4.21 (2H, m), 4.51 (2H, d, J=10.8 Hz), 4.67 (2H, d, J=12.0 Hz), 4.72 (2H, d, J=12.0 Hz), 4.86 (4H, d, J=10.8 Hz), 5.00 (2H, d, J=10.8 Hz), 5.17 (2H, d, J=3.6 Hz), 7.23-7.37 (30H, m); $^{13}$C NMR (75 MHz in CDCl$_3$) δ14.16, 22.72, 26.54, 29.40, 29.69, 29.72, 29.97, 31.95, 33.68, 33.79, 34.92, 39.11, 62.37, 69.14, 72.96, 75.33, 75.72, 77.24, 77.62, 79.40, 81.59, 94.07, 127.46, 127.66, 127.81, 127.94, 128.11, 128.44, 128.50, 137.80, 137.87, 138.63, 173.28; FABMS m/z (%) 1691 (M$^+$+H+Na); HRMS (FAB$^+$) m/z calcd for C$_{112}$H$_{171}$O$_{13}$Na (M$^+$+H+Na) 1747.2619, Found 1747.2618.

Production Example B-7

Synthesis of 6,6'-bis-O-(3-tetradecylheptadecanoyl)-2,3,4,2',3',4'-hexabenzyl-60 ,α'-trehalose

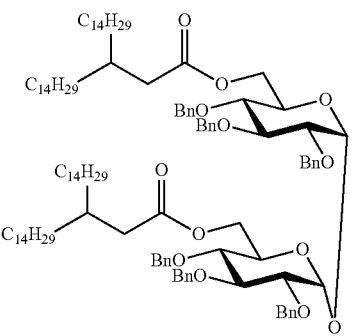

[Formula 36]

6,6'-Bis-O-(3-tetradecylheptadecanoyl)-2,3,4,2',3',4'-hexabenzyl-α,α'-trehalose was obtained by the same method as that applied in Production Example B-1, using the 3-tetradecylheptadecanoic acid obtained by the method described in Production Example D-6 as carboxylic acid.

colorless syrup; $[\alpha]_D^{20}$+43.7° (c 1.0 CHCl$_3$); FT IR (neat) 3087, 3064, 3032, 2924, 2853, 1943, 1871, 1796, 1739 cm$^{-1}$; $^1$H NMR (300 MHz in CDCl$_3$) δ0.88 (12H, t, J=6.9 Hz), 1.23 (104H, m), 1.80 (2H, m), 2.19 (4H, d, J=6.9 Hz), 3.54 (4H, m), 4.04 (2H, t, J=9.6 Hz), 4.11(4H, m), 4.21 (2H, m), 4.51 (2H, d, J=10.5 Hz), 4.67 (2H, d, J=12.0 Hz), 4.72 (2H, d, J=12.0 Hz), 4.86 (4H, d, J=10.5 Hz), 5.00 (2H, d, J=10.5 Hz), 5.17 (2H, d, J=3.3 Hz), 7.22-7.37 (30H, m); $^{13}$C NMR (75 MHz in CDCl$_3$) δ14.16, 22.72, 26.55, 29.39, 29.70, 29.73, 29.97, 31.95, 33.68, 33.79, 34.92, 39.11, 62.38, 69.15, 72.97, 75.32, 75.72, 77.23, 77.63, 79.41, 81.59, 94.06, 127.46, 127.65, 127.81, 127.94, 128.11, 128.44, 128.49, 137.81, 137.88, 138.63, 173.27; FABMS m/z (%) 1802 (M$^+$+Na); HRMS (FAB$^+$) m/z calcdfor C$_{116}$H$_{178}$O$_{13}$Na (M$^+$+Na) 1802.3185, Found 1802.3175.

Example 9

Production Example β-1

Synthesis of 6,6'-bis-O-(3-nonyldodecanoyl)-α,α'-trehalose

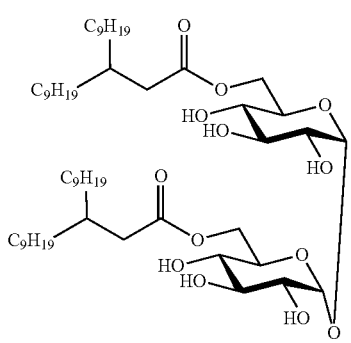

[Formula 37]

The 6,6'-bis-O-(3-nonyldodecanoyl)-2,3,4,2',3',4'-hexabenzyl-α,α-trehalose(350 mg, 233 μmol) obtained by the method described in Production Example B-1 was dissolved in a mixed solvent (5 ml) of chloroform:methanol:acetic acid (5:1:0.5), and palladium hydroxide (3 w/w %, 13 mg, 18.5 μmol) was then added to the obtained solution. The obtained mixture was stirred under 1 atmospheric pressure of hydrogen for 27 hours. Thereafter, the reaction mixture was filtrated and was then concentrated, and the residue was purified using column chromatography (dichloromethane:methanol=15:1), so as to obtain 6,6'-bis-O-(3-nonyldodecanoyl)-α,α'-trehalose (135 mg, 61%) in the form of a colorless amorphous solid.

colorless syrup; $[\alpha]_D^{21}$ +62.8° (c 0.7 $CHCl_3$); FT IR (neat) 3316, 2926, 2854, 1743 $cm^{-1}$; $^1$H NMR (300 MHz in $C_5D_5N$) δ0.81 (12H, t, J=6.9 Hz), 1.23 (64H, m),1.99 (2H, m), 2.33 (4H, d, J=6.6 Hz), 4.13 (2H, t, J=9.6 Hz), 4.25 (2H, dd,J=9.6, 3.9 Hz), 4.74 (2H, t, J=9.6 Hz), 4.78 (2H, d, J=12.3 Hz), 4.93 (2H, d, J=12.3 Hz), 4.98 (2H, m), 5.81 (2H, d, J=3.9 Hz); $^{13}$C NMR (75 MHz in $C_5D_5N$) δ14.29, 22.94, 29.84, 29.62, 29.91, 29.94, 30.22, 32.12, 34.10, 35.23, 39.33, 64.26, 71.48, 71.96, 73.35, 74.82, 95.82, 173.51; FABMS m/z (%) 982 ($M^+$+Na); HRMS ($FAB^+$) m/z calcd for $C_{54}H_{102}O_{13}Na$ ($M^+$+Na) 981.7218, Found 981.7198.

Example 15

Production Example β-2

Synthesis of 6,6'-bis-O-(3-octylundecanoyl)-α,α'-trehalose

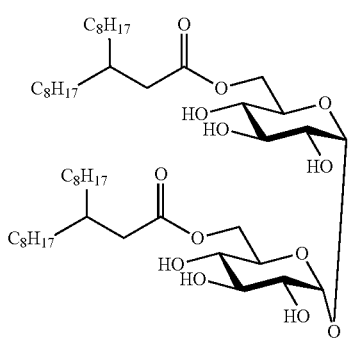

[Formula 38]

6,6'-Bis-O-(3-octylundecanoyl)-α,α'-trehalose was obtained by the same method as that applied in Production Example β-1, using the 6,6'-bis-O-(3-octylundecanoyl)-2,3,4,2',3',4'-hexabenzyl-α,α'-trehalose obtained by the method described in Production Example B-2 as a raw material compound.

colorless syrup; $[\alpha]_D^{21}$ +70.7° (c 0.4 $CHCl_3$); FT IR (neat) 3275, 2925, 2854, 1742 $cm^{-1}$; $^1$H NMR (300 MHz in $C_5D_5N$) δ0.86 (12H, t, J=7.2 Hz), 1.24 (56H, m),2.03 (2H, m), 2.37 (4H, d, J=6.6 Hz), 4.19 (2H, t, J=9.3 Hz), 4.31 (2H, dd,J=9.6, 3.6 Hz), 4.74 (2H, t, J=9.3 Hz), 4.85 (2H, dd, J=11.7, 5.7 Hz), 5.01 (2H, d, J=11.7 Hz), 5.11 (2H, m), 5.89 (2H, d, J=3.9 Hz); $^{13}$C NMR (75 MHz in $C_5D_5N$) δ14.28, 22.93, 26.83, 26.87, 29.59, 29.87, 30.21, 32.11, 34.10, 35.23, 39.32, 64.26, 71.48, 71.95, 73.35, 74.83, 95.82, 173.52; FABMS m/z (%) 926 ($M^+$+Na); HRMS ($FAB^+$) m/z calcd for $C_{50}H_{94}O_{13}Na$ ($M^+$+Na) 925.6592, Found 925.6585.

Example 10

Production Example β-3

Synthesis of 6,6'-bis-O-(3-decyltridecanoyl)-α,α'-trehalose

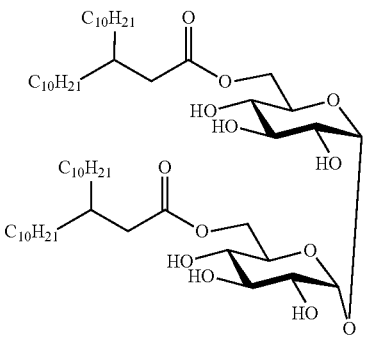

[Formula 39]

6,6'-Bis-O-(3-decyltridecanoyl)-α,α'-trehalose was obtained by the same method as that applied in Production Example β-1, using the 6,6'-bis-O-(3-decyltridecanoyl)-2,3,4,2',3',4'-hexabenzyl-α,α'-trehalose obtained by the method described in Production Example B-3 as a raw material compound.

colorless syrup; $[\alpha]_D^{21}$ +60.9° (c 0.9 $CHCl_3$); FT IR (neat) 3279, 2924, 2854, 1742 $cm^{-1}$; $^1$H NMR (300 MHz in $C_5D_5N$) δ0.83 (12H, t, J=6.9 Hz), 1.24 (72H, m),2.00 (2H, m), 2.35 (4H, d, J=6.6 Hz), 4.14 (2H, t, J=8.7 Hz), 4.26 (2H, dd,J=9.6, 3.3 Hz), 4.74 (2H, t, J=9.0 Hz), 4.78 (2H, dd, J=11.7, 5.4 Hz), 4.95 (2H, d, J=12.0 Hz), 5.01 (2H, m), 5.82 (2H, d, J=3.9 Hz); $^{13}$C NMR (75 MHz in $C_5D_5N$) δ14.10, 22.74, 26.65, 29.41, 29.73, 30.00, 31.92, 33.87, 35.03, 39.16, 64.10, 71.10, 71.57, 72.92, 74.38, 95.14, 173.52; FABMS m/z (%) 1037 ($M^+$+Na); HRMS ($FAB^+$) m/z calcd for $C_{58}H_{110}O_{13}Na$ ($M^+$+Na) 1037.7903, Found 1037.7874.

Example 11

Production Example β-4

Synthesis of 6,6'-bis-O-(3-undecyltetradecanoyl)-α,α'-trehalose

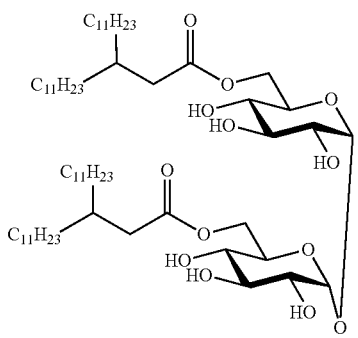

[Formula 40]

6,6'-Bis-O-(3-undecyltetradecanoyl)-α,α'-trehalose was obtained by the same method as that applied in Production Example β-1, using the 6,6'-bis-O-(3-undecyltetradecanoyl)-2,3,4,2',3',4'-hexabenzyl-α,α'-trehalose obtained by the method described in Production Example B-4 as a raw material compound.

colorless syrup; $[\alpha]_D^{21}$ +60.6° (c 0.5 CHCl$_3$); FT IR (neat) 3289, 2925, 2853, 1743 cm$^{-1}$; $^1$H NMR (300 MHz in C$_5$D$_5$N) δ0.86 (12H, t, J=6.9 Hz), 1.28 (80H, m), 2.04 (2H, m), 2.38 (4H, d, J=6.6 Hz), 4.19 (2H, t, J=9.0 Hz), 4.31 (2H, dd, J=9.0, 3.6 Hz), 4.74 (2H, t, J=9.0 Hz), 4.85 (2H, dd, J=11.7, 5.1 Hz), 5.05 (2H, d, J=11.7 Hz), 5.01 (2H, m), 5.89 (2H, d, J=3.9 Hz); $^{13}$C NMR (75 MHz in C$_5$D$_5$N) δ14.30, 22.96, 26.92, 29.64, 30.00, 30.27, 32.14, 34.14, 35.26, 39.37, 64.30, 71.52, 72.00, 73.40, 74.87, 95.86, 173.53; FABMS m/z (%) 1094 (M$^+$+Na); HRMS (FAB$^+$) m/z calcd for C$_{62}$H$_{118}$O$_{13}$Na (M$^+$+Na) 1093.8470, Found 1093.8458.

Example 12

Production Example β-5

Synthesis of 6,6'-bis-O-(3-dodecylpentadecanoyl)-α,α'-trehalose

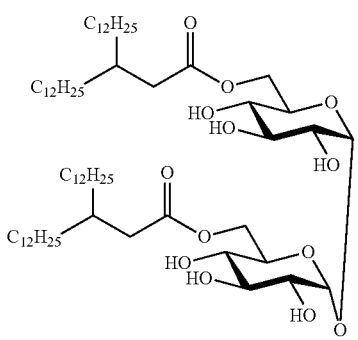

[Formula 41]

6,6'-Bis-O-(3-dodecylpentadecanoyl)-α,α'-trehalose was obtained by the same method as that applied in Production Example β-1, using the 6,6'-bis-O-(3-dodecylpentadecanoyl)-2,3,4,2',3',4'-hexabenzyl-α,α'-trehalose obtained by the method described in Production Example B-5 as a raw material compound.

colorless syrup; $[\alpha]_D^{21}$ +52.5° (c 0.3 CHCl$_3$); FT IR (neat) 3271, 2923, 2853, 1743 cm$^{-1}$; $^1$H NMR (300 MHz in C$_5$D$_5$N) δ0.84 (12H, t, J=6.3 Hz), 1.25 (88H, m), 2.02 (2H, m), 2.36 (4H, d, J=6.6 Hz), 4.15 (2H, t, J=9.0 Hz), 4.27 (2H, dd, J=9.9, 3.6 Hz), 4.74 (2H, t, J=9.6 Hz), 4.81 (2H, dd, J=11.4, 4.8 Hz), 4.97(2H, d, J=11.4 Hz), 5.02 (2H, m), 5.84 (2H, d, J=2.4 Hz); $^{13}$C NMR (75 MHz in C$_5$D$_5$N) δ14.18, 22.82, 26.73, 29.50, 29.87, 30.12, 32.01, 33.97, 35.12, 39.25, 64.18, 71.25, 71.71, 73.06, 74.51, 95.38, 173.52; FABMS m/z (%) 1150 (M$^+$+Na); HRMS (FAB$^+$) m/z calcd for C$_{66}$H$_{126}$O$_{13}$Na (M$^+$+Na) 1149.9110, Found 1149.9103.

Example 13

Production Example β-6

Synthesis of 6,6'-bis-O-(3-tridecylhexadecanoyl)-α,α'-trehalose

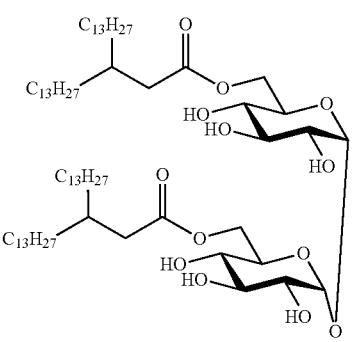

[Formula 42]

6,6'-Bis-O-(3-tridecylhexadecanoyl)-α,α'-trehalose was obtained by the same method as that applied in Production Example β-1, using the 6,6'-bis-O-(3-tridecylhexadecanoyl)-2,3,4,2',3',4'-hexabenzyl-α,α'-trehalose obtained by the method described in Production Example B-6 as a raw material compound.

colorless syrup; $[\alpha]_D^{21}$ +42.3° (c 0.5 CHCl$_3$); FT IR (neat) 3321, 2925, 2853, 1742 cm$^{-1}$; $^1$H NMR (300 MHz in C$_5$D$_5$N) δ0.83 (12H, t, J=6.6 Hz), 1.27 (96H, m), 2.02 (2H, m), 2.36 (4H, d, J=6.9 Hz), 4.15 (2H, t, J=9.3 Hz), 4.27 (2H, dd, J=9.3, 3.3 Hz), 4.75 (2H, t, J=9.3 Hz), 4.80 (2H, dd, J=12.0, 5.4 Hz), 4.97 (2H, d, J=12.0 Hz), 5.02 (2H, m), 5.84 (2H, d, J=3.6 Hz); $^{13}$C NMR (75 MHz in C$_5$D$_5$N) δ14.30, 22.96, 26.91, 29.65, 30.03, 30.28, 32.15, 34.12, 35.25, 39.36, 64.28, 71.51, 71.99, 73.38, 74.85, 95.83, 173.51; FABMS m/z (%) 1206 (M$^+$+Na); HRMS (FAB$^+$) m/z calcd for C$_{70}$H$_{134}$O$_{13}$Na (M$^+$+Na) 1205.9770, Found 1205.9746.

Example 14

Production Example β-7

Synthesis of 6,6'-bis-O-(3-tetradecylheptadecanoyl)-α,α'-trehalose

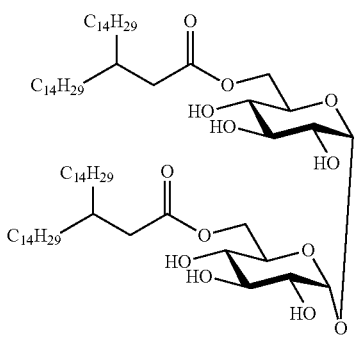

[Formula 43]

6,6'-Bis-O-(3-tetradecylheptadecanoyl)-α,α'-trehalose was obtained by the same method as that applied in Production Example β-1, using the 6,6'-bis-O-(3-tetradecylheptadecanoyl)-2,3,4,2',3',4'-hexabenzyl-α,α'-trehalose obtained by the method described in Production Example B-7 as a raw material compound.

colorless syrup; $[\alpha]_D^{21}$ +55.7° (c 1.0 CHCl$_3$); FT IR (neat) 3310, 2925, 2853, 1743 cm$^{31\ 1}$; $^1$H NMR (300 MHz in C$_5$D$_5$N) δ0.84 (12H, t, J=6.9 Hz), 1.26 (104H, m), 2.03 (2H, m), 2.37 (4H, d, J=6.6 Hz), 4.15 (2H, t, J=9.9 Hz), 4.28 (2H, dd, J=9.6, 3.9 Hz), 4.74 (2H, t, J=9.9 Hz), 4.81 (2H, dd, J=11.7, 5.4 Hz), 4.97 (2H, d, J=11.7 Hz), 5.03 (2H, m), 5.84 (2H,d, J=3.6 Hz); $^{13}$C NMR (75 MHz in C$_5$D$_5$N) δ14.05, 22.67, 26.55, 29.36, 29.67, 29.74, 29.94, 31.87, 33.74, 34.95, 39.14, 64.02, 70.91, 71.46, 72.77, 74.20, 94.69, 173.45; FABMS m/z (%) 1262 (M$^+$+Na); HRMS (FAB$^+$) m/z calcd for C$_{74}$H$_{142}$O$_{13}$Na (M$^+$+Na) 1262.0348, Found 1262.0348.

[Synthesis of Carboxylic Acid Used as Raw Material]

Production Example C-1

Synthesis of 2-decyl dodecanoate

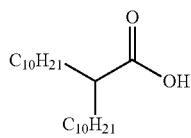

[Formula 44]

Anhydrous THF (11 ml) was added to a dried double-necked flask, and sodium hydride (60 w/w %, 397 mg, 9.93 mmol) was then added thereto. The obtained mixture was cooled to 0° C., and diethyl malonate (530 mg, 3.31 mmol) was then added dropwise thereto. The obtained mixture was stirred at 0° C. for 10 minutes, and 1-iododecane (2.22 g, 8.28 mmol) was then added thereto, followed by stirring at a room temperature for 6 hours. Thereafter, a saturated ammonium chloride aqueous solution was added to the reaction solution, and the resultant was then extracted with ether three times. The organic layer was dried over anhydrous magnesium sulfate, and it was filtrated and was then concentrated. The obtained residue was dissolved in a mixed solvent of a 10 N sodium hydroxide aqueous solution (4 ml) and n-butanol (8 ml), and the solution was then heated to reflux for 6 hours. Thereafter, the reaction solution was cooled to a room temperature, and 1 N hydrochloric acid was then added thereto, followed by extraction with ether three times. The organic layer was dried over anhydrous sodium sulfate, and it was filtrated and was then concentrated. The obtained residue was dissolved in acetic acid (3.3 ml), and the mixed solution was then heated to reflux for 18 hours. After cooling the reaction solution, it was concentrated under a reduced pressure to remove acetic acid. The residue was purified by silica gel column chromatography (hexane :ethyl acetate=7:1), so as to obtain carboxylic acid (2-decyl dodecanoate) (710 mg, 63%) in the form of a white amorphous powder.

white powder; FT IR (neat) 3041, 2943, 2857, 2689, 1714 cm$^{-1}$; $^1$H NMR (300 MHz in CDCl$_3$) δ0.88 (6H, t, J=7.6Hz), 1.21 (32H, m), 1.48 (2H, m), 1.61 (2H, m),2.34 (1H, m); $^{13}$C NMR (75 MHz in CDCl$_3$) δ14.13, 22.72, 27.40, 29.37, 29.50, 29.64, 31.95, 32.19, 45.61, 183.22; CIMS m/z (%) 341 (M$^+$+H); HRMS (CI$^+$) m/z calcd for C$_{22}$H$_{45}$O$_2$(M$^+$+H) 341.3420, Found 341.3421.

Production Example C-2

Synthesis of 2-octyl decanoate

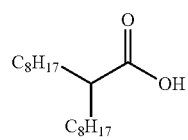

[Formula 45]

2-Octyl decanoate was obtained by the same method as that applied in Production Example C-1, using 1-iodooctane instead of 1-iododecane.

white powder; FT IR (neat) 3032, 2927, 2856, 1707 cm$^{-1}$; $^1$H NMR (300 MHz in CDCl$_3$) δ0.88 (6H, t, J=6.9 Hz), 1.26 (24H, m), 1.48 (2H, m), 1.63 (2H, m), 2.34 (1H, m); $^{13}$C NMR (75 MHz in CDCl$_3$) δ14.12, 22.70, 27.40, 29.30, 29.45, 29.60, 31.90, 32.20, 45.66, 183.50; CIMS m/z (%) 285 (M$^+$+H); HRMS (CI$^+$) m/z calcd for C$_{18}$H$_{37}$O$_2$(M$^+$+H) 285.2794, Found 285.2772.

Production Example C-3

Synthesis of 2-nonyl undecanoate

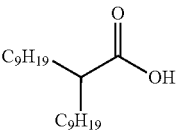

[Formula 46]

2-Nonyl undecanoate was obtained by the same method as that applied in Production Example C-1, using 1-iodononane instead of 1-iododecane.

white powder; FT IR (neat) 3019, 2934, 2858, 1712 cm$^{-1}$; $^1$H NMR (300 MHz in CDCl$_3$) δ0.88 (6H, t, J=6.9 Hz), 1.26 (28H, m), 1.48 (2H, m), 1.61 (2H, m), 2.33 (1H, m); $^{13}$C NMR (75 MHz in CDCl$_3$) δ14.14, 22.72, 27.40, 29.34, 29.50, 29.60, 31.92, 32.20, 45.60, 183.11; CIMS m/z (%) 313 (M$^+$+H); HRMS (CI$^+$) m/z calcd for C$_{20}$H$_{41}$O$_2$ (M$^+$+H) 313.3106, Found 313.3111.

Production Example C-4

Synthesis of 2-undecyl tridecanoate

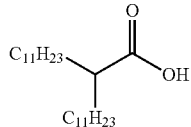

[Formula 47]

2-Undecyl tridecanoate was obtained by the same method as that applied in Production Example C-1, using 1-iodoundecane instead of 1-iododecane.

white powder; FT IR (neat) 3028, 2941, 2858, 1712 cm$^{-1}$; $^1$H NMR (300 MHz in CDCl$_3$) δ0.88 (6H, t, J=6.9 Hz), 1.25 (36H, m), 1.48 (2H, m), 1.61 (2H, m), 2.35 (1H, m); $^{13}$C NMR (75 MHz in CDCl$_3$) δ14.17, 22.74, 27.41, 29.40, 29.51, 29.61, 29.65, 29.69, 29.72, 31.97, 32.20, 45.55, 182.81; CIMS m/z (%) 369 (M$^+$+H); HRMS (CI$^+$) m/z calcd for C$_{24}$H$_{49}$O$_2$(M$^+$+H) 369.3732, Found 369.3731.

Production Example C-5

Synthesis of 2-dodecyl tetradecanoate

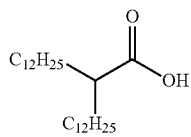

[Formula 48]

2-Dodecyl tetradecanoate was obtained by the same method as that applied in Production Example C-1, using 1-iodododecane instead of 1-iododecane.

white powder; FT IR (neat) 3028, 2943, 2860, 2691, 1714 cm$^{-1}$; $^1$H NMR (300 MHz in CDCl$_3$) δ0.88 (6H, t, J=7.1Hz), 1.25 (40H, m), 1.48 (2H, m), 1.61 (2H, m), 2.34 (1H, m); $^{13}$C NMR (75 MHz in CDCl$_3$) δ14.16, 22.76, 27.43, 29.43, 29.54, 29.64, 29.68, 29.71, 29.72, 31.99, 32.22, 45.68, 183.46; CIMS m/z (%) 397 (M$^+$+H); HRMS (CI$^+$) m/z calcd for C$_{26}$H$_{53}$O$_2$(M$^+$+H) 397.4045, Found 397.4043.

Production Example C-6

Synthesis of 2-tridecyl pentadecanoate

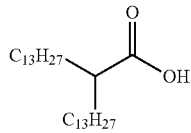

[Formula 49]

2-Tridecyl pentadecanoate was obtained by the same method as that applied in Production Example C-1, using 1-iodotridecane instead of 1-iododecane.

white powder; FT IR (neat) 3032, 2922, 2851, 2691, 1712 cm$^{-1}$; $^1$H NMR (300 MHz in CDCl$_3$) δ0.88 (6H, t, J=6.9 Hz), 1.25 (44H, m), 1.48 (2H, m), 1.61 (2H, m), 2.35 (1H, m); $^{13}$C NMR (75 MHz in CDCl$_3$) δ14.14, 22.72, 27.40, 29.39, 29.50, 29.60, 29.64, 29.69, 31.96, 32.19, 45.54, 182.79; CIMS m/z (%) 425 (M$^+$+H); HRMS (CI$^+$) m/z calcd for C$_{28}$H$_{57}$O$_2$(M$^+$+H) 425.4358, Found 425.4341.

Production Example C-7

Synthesis of 2-tetradecyl hexadecanoate

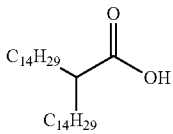

[Formula 50]

2-Tetradecyl hexadecanoate was obtained by the same method as that applied in Production Example C-1, using 1-iodotetradecane instead of 1-iododecane.

white powder; FT IR (neat) 3028, 2928, 2854, 2684, 1706 cm$^{-1}$; $^1$H NMR (300 MHz in CDCl$_3$) δ0.88 (6H, t, J=7.2Hz), 1.25 (48H, m), 1.48 (2H, m), 1.60 (2H, m), 2.34 (1H, m); $^{13}$C NMR (75 MHz in CDCl$_3$) δ14.13, 22.72, 27.40, 29.40, 29.50, 29.60, 29.64, 29.73, 31.96, 32.19, 45.57, 182.87; CIMS m/z (%) 453 (100 M$^+$+H); HRMS (CI$^+$) m/z calcd for C$_{30}$H$_{61}$O$_2$ (M$^+$+H) 453.4671, Found 453.4677.

Production Example C-8

Synthesis of 2-pentadecyl heptadecanoate

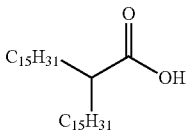

[Formula 51]

2-Pentadecyl heptadecanoate was obtained by the same method as that applied in Production Example C-1, using 1-iodopentadecane instead of 1-iododecane.

white powder; FT IR (neat) 3028, 2911, 2848, 2650, 1703 cm$^{-1}$; $^1$H NMR (300 MHz in CDCl$_3$) δ0.88 (6H, t, J=6.9 Hz), 1.25 (52H, m), 1.48 (2H, m), 1.61 (2H, m), 2.35 (1H, m); $^{13}$C NMR (75 MHz in CDCl$_3$) δ14.05, 22.65, 27.33, 29.33, 29.43, 29.53, 29.57, 29.66, 31.90, 32.14, 45.43, 182.41; CIMS m/z (%) 481 (M$^+$+H); HRMS (CI$^+$) m/z calcd for C$_{32}$H$_{65}$O$_2$(M$^+$+H) 481.4984, Found 481.4977.

Production Example C-9

Synthesis of 2-hexadecyl octadecanoate

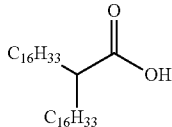

[Formula 52]

2-Hexadecyl octadecanoate was obtained by the same method as that applied in Production Example C-1, using 1-iodohexadecane instead of 1-iododecane.

white powder; FT IR (neat) 3028, 2914, 2848, 2691, 1705 cm$^{-1}$; $^1$H NMR (300 MHz in CDCl$_3$) δ0.88 (6H, t, J=6.9 Hz), 1.25 (56H, m), 1.48 (2H, m), 1.61 (2H, m), 2.35 (1H, m); $^{13}$C NMR (75 MHz in CDCl$_3$) δ14.14, 22.72, 27.40, 29.40, 29.50, 29.60, 29.64, 29.73, 31.96, 32.20, 45.51, 182.51; CIMS m/z (%) 509 (M$^+$+H); HRMS (CI$^+$) m/z calcd for C$_{34}$H$_{69}$O$_2$(M$^+$+H) 509.5297, Found 509.5298.

Production Example D-1

Synthesis of 3-nonyl dodecanoate

3-Nonyl dodecanoate was synthesized by the following Production Examples D-1-1 to D-1-5.

Production Example D-1-1

Synthesis of N-methoxy-N-methyldecanamide

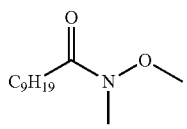

[Formula 53]

Decanoic acid (4 g, 23.2 mmol) was dissolved in an anhydrous dichloromethane solution (80 mL), and 1,1-carbonyldiimidazole (4.5 g, 27.9 mmol) was then added to the solution, followed by stirring for 1.5 hours. Subsequently, N,O-dimethylhydroxyamine hydrochloride (2.7 g, 27.9 mmol) was added to the reaction solution, and the obtained mixture was further stirred for 3 hours. After addition of distilled water, the reaction solution was extracted with dichloromethane two times. Anhydrous magnesium sulfate was added to the organic layer to dry it, and the resultant was filtrated and was then concentrated. The obtained residue was purified using column chromatography (hexane:ethyl acetate=8:1), so as to obtain N-methoxy-N-methyldecanamide (4.8 g, 97%) as an amide body in the form of a colorless transparent liquid.

colorless oil; FT IR (neat) 2927, 2854, 1731 cm$^{-1}$; $^1$H NMR (300 MHz in CDCl$_3$) δ0.88 (3H, t, J=6.9 Hz), 1.27 (12H, m), 1.63 (2H, m), 2.41 (2H, t, J=7.8 Hz), 3.18 (3H, s), 3.68 (3H, s); $^{13}$C NMR (75 MHz in CDCl$_3$) δ14.09, 22.65, 24.65, 29.28, 29.45, 31.86, 61.17, 174.77; CIMS m/z (%) 215 (M$^+$); HRMS (CI$^+$) m/z calcd for C$_{12}$H$_{25}$NO$_2$(M$^+$) 215.1921, Found 215.1903.

Production Example D-1-2

Synthesis of 10-nonadecanone

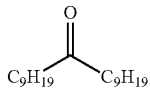

[Formula 54]

Polished shaved magnesium (3.2 g, 134 mmol) was heated, and thereafter, an anhydrous THF solution (68 ml) of 1-bromononane (12.9 ml, 67.5 mmol) was slowly added dropwise thereto. After heating to reflux for 1.5 hours, the reaction solution was cooled to a room temperature, and it was then added dropwise to a THF (80 mL) solution of the N-methoxy-N-methyldecanamide (4.8 g, 22.5 mmol) obtained by the method described in Production Example D-1-1. After the obtained mixture had been stirred for 30 minutes, 1 N hydrochloric acid was added to the reaction solution, followed by extraction with diethyl ether two times. Anhydrous magnesium sulfate was added to the organic layer to dry it, and the resultant was filtrated and was then concentrated. The obtained residue was purified using column chromatography (hexane:dichloromethane=8:1), so as to obtain 10-nonadecanone (6.0 g, 95%) as a ketone body in the form of a white amorphous solid.

colorless solid; FT IR (neat) 2953, 2916, 2847, 1698 cm$^{-1}$; $^1$H NMR (300 MHz in CDCl$_3$) δ0.88 (6H, t, J=6.9 Hz), 1.26 (24H, m), 1.55 (4H, m), 2.38 (4H, t, J=7.5 Hz); $^{13}$C NMR (75 MHz in CDCl$_3$) δ14.03, 22.63, 23.84, 29.24, 29.41, 31.84, 42.74, 211.49; CIMS m/z (%) 282 (M$^+$); HRMS (CI$^+$) m/z calcd for C$_{19}$H$_{38}$O (M$^+$) 282.2882, Found 282.2902.

Production Example D-1-3

Synthesis of ethyl 3-nonyl-2-dodecanoate

[Formula 55]

Sodium hydride (60 w/w %, 6 g, 142 mmol) was dissolved in anhydrous THF (200 ml), and the obtained mixture was then cooled to 0° C. Ethyl diethylphosphonoacetate (34 ml, 171 mmol) was added dropwise to the reaction solution, and the obtained mixture was then stirred for 30 minutes. Thereafter, the temperature of the obtained reaction solution was increased to a room temperature, and the 10-nonadecanone (6.0 g, 21.3 mmol) obtained by the method described in Production Example D-1-2 was then added to the reaction solution. The obtained mixture was further heated to reflux for 18 hours. Thereafter, distilled water was added to the reaction solution, followed by extraction with diethyl ether two times. Anhydrous magnesium sulfate was added to the organic layer to dry it, and the resultant was filtrated and was then concentrated. The obtained residue was purified using column chromatography (hexane:dichloromethane=6:1), so as to obtain ethyl 3-nonyl-2-dodecanoate (7.6 g, 99%) as an ester form in the form of a colorless transparent liquid.

colorless oil; FT IR (neat) 2928, 2855, 1718 cm$^{-1}$; $^1$H NMR (300 MHz in CDCl$_3$) δ0.88 (6H, t, J=6.9 Hz), 1.27 (27H, m), 1.44 (4H, m), 2.12 (2H, t, J=7.8 Hz), 2.58 (2H, t, J=8.1 Hz), 4.14 (2H, q, J=7.2 Hz), 5.61 (1H, br s); $^{13}$C NMR (75 MHz in CDCl$_3$) δ14.14, 14.35, 22.70, 27.68, 28.75, 29.34, 29.49, 29.52, 29.60, 30.01, 31.92, 32.19, 38.44, 59.42, 114.98, 165.07, 166.66; CIMS m/z (%) 352 (M$^+$); HRMS (CI$^+$) m/z calcd for C$_{23}$H$_{44}$O$_2$ (M$^+$) 352.3349, Found 352.3345.

Production Example D-1-4

Synthesis of ethyl 3-nonyldodecanoate

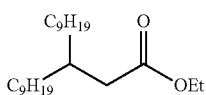

[Formula 56]

The ethyl 3-nonyl-2-dodecanoate (7.6 g, 21.7 mmol) obtained by the method described in Production Example D-1-3 was dissolved in a mixed solvent (100 ml) of chloroform:methanol (5:1). A PtO$_2$ catalyst (3 w/w %, 223 mg, 983 μmol) was added to the solution, and the obtained mixture was then stirred under 1 atmospheric pressure of hydrogen for 23 hours. Thereafter, the PtO$_2$ catalyst was removed using a filter paper, and the residue was then concentrated. The obtained residue was purified using column chromatography (hexane:diethyl ether=50:1), so as to obtain ethyl 3-nonyldodecanoate (7.1 g, 92%) in the form of a colorless transparent liquid.

colorless oil; FT IR (neat) 2929, 2855, 1739 cm$^{-1}$; $^1$H NMR (300 MHz in CDCl$_3$) δ0.88 (6H, t, J=6.6 Hz), 1.26 (35H, m), 1.84 (1H, m), 2.21 (2H, d, J=6.6 Hz), 4.12 (2H, q, J=7.2 Hz); $^{13}$C NMR (75 MHz in CDCl$_3$) δ14.16, 14.32, 22.73, 26.55, 29.38, 29.64, 29.66, 29.93, 31.95, 33.91, 35.10, 39.40, 60.07, 173.73; CIMS m/z (%) 354 (M$^+$); HRMS (CI$^+$) m/z calcd for C$_{23}$H$_{46}$O$_2$ (M$^+$) 354.3508, Found 354.3503.

Production Example D-1-5

Synthesis of 3-nonyl dodecanoate

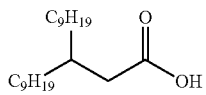

[Formula 57]

The ethyl 3-nonyldodecanoate (6.3 g, 17.7 mmol) obtained by the method described in Production Example D-1-4 was dissolved in a water-saturated butanol solution (80 ml), and KOH (10 g, 177 mmol) was then added to the solution, followed by heating to reflux for 4.5 hours. Thereafter, 1 N hydrochloric acid was added to the reaction solution, and the obtained mixture was then extracted with diethyl ether two times. Anhydrous magnesium sulfate was added to the organic layer to dry it, and the resultant was filtrated and was then concentrated. The obtained residue was purified using column chromatography (hexane:ethyl acetate=10:1), so as to obtain 3-nonyl dodecanoate (6.3 g, 99%) in the form of a colorless transparent liquid.

colorless oil; FT IR (neat) 2925, 2854, 1709 cm$^{-1}$; $^1$H NMR (200 MHz in CDCl$_3$) δ0.88 (6H, t, J=6.6 Hz), 1.26 (32H, m), 1.85 (1H, m), 2.27 (2H, d, J=6.9 Hz); $^{13}$C NMR (75 MHz in CDCl$_3$) δ14.16, 22.73, 26.52, 29.38, 29.65, 29.89, 31.95, 33.79, 34.87, 39.00, 179.94; CIMS m/z (%) 326 (M$^+$); HRMS (CI$^+$) m/z calcd for C$_{21}$H$_{42}$O$_2$(M$^+$) 326.3129, Found 326.3157.

Production Example D-2

Synthesis of 3-octyl undecanoate

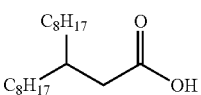

[Formula 58]

As starting compounds, using octanoic acid instead of the decanoic acid described in Production Example D-1-1, also using 1-bromooctane instead of the 1-bromononane described in Production Example D-1-2, and using the compound produced in each step in the subsequent step, 3-octyl undecanoate was synthesized by the same methods as those described in Production Examples D-1-1 to D-1-5.

colorless oil; FT IR (neat) 2926, 2855, 1712 cm$^{-1}$; $^1$H NMR (300 MHz in CDCl$_3$) d 0.88 (6H, t, J=6.6 Hz), 1.26 (28H, m), 1.85 (1H, m), 2.27 (2H, d, J=6.9 Hz); $^{13}$C NMR (75 MHz in CDCl$_3$) d 14.16, 22.71, 26.52, 29.34, 29.61, 29.89, 31.93, 33.80, 34.88, 38.94, 179.58; CIMS m/z (%) 298 (M$^+$); HRMS (CI$^+$) m/z calcd for C$_{19}$H$_{38}$O$_2$(M$^+$) 298.2876, Found 298.2874.

Production Example D-3

Synthesis of 3-decyl tridecanoate

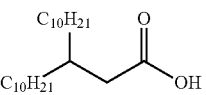

[Formula 59]

As starting compounds, using undecanoic acid instead of the decanoic acid described in Production Example D-1-1, also using 1-bromodecane instead of the 1-bromononane described in Production Example D-1-2, and using the compound produced in each step in the subsequent step, 3-decyl tridecanoate was synthesized by the same methods as those described in Production Examples D-1-1 to D-1-5.

colorless oil; FT IR (neat) 2935, 2857, 1711 cm$^{-1}$; $^1$H NMR (300 MHz in CDCl$_3$) δ0.88 (6H, t, J=6.6 Hz), 1.26 (36H, m), 1.85 (1H, m), 2.27 (2H, d, J=6.9 Hz); $^{13}$C NMR (75 MHz in CDCl$_3$) δ14.15, 22.72, 26.51, 29.38, 29.66, 29.88, 31.94, 33.78, 34.86, 38.95, 179.79; CIMS m/z (%) 354 (M$^+$); HRMS (CI$^+$) m/z calcd for C$_{23}$H$_{46}$O$_2$(M$^+$) 354.3498, Found 354.3503.

Production Example D-4

Synthesis of 3-undecyl tetradecanoate

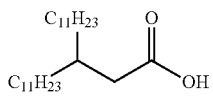

[Formula 60]

As starting compounds, using dodecanoic acid instead of the decanoic acid described in Production Example D-1-1, also using 1-bromoundecane instead of the 1-bromononane described in Production Example D-1-2, and using the compound produced in each step in the subsequent step, 3-undecyl tetradecanoate was synthesized by the same methods as those described in Production Examples D-1-1 to D-1-5.

colorless solid; FT IR (neat) 2923, 2853, 1707 cm$^{-1}$; $^1$H NMR (300 MHz in CDCl$_3$) δ0.88 (6H, t, J=6.9 Hz), 1.26 (40H, m), 1.85 (1H, m), 2.27 (2H, d, J=6.9 Hz); $^{13}$C NMR (75 MHz in CDCl$_3$) δ14.17, 22.74, 26.53, 29.40, 29.69, 29.72, 29.89, 31.96, 33.79, 34.88, 38.98, 179.82; CIMS m/z (%) 382 (M$^+$); HRMS (CI$^+$) m/z calcd for C$_{25}$H$_{50}$O$_2$(M$^+$) 382.3811, Found 382.3816.

Production Example D-5

Synthesis of 3-dodecyl pentadecanoate

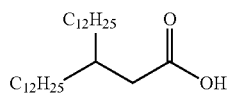

[Formula 61]

Using the ethyl 3-dodecyl pentadecanoate obtained by the method described in Production Example D-5-4 instead of the ethyl 3-nonyl dodecanoate described in Production Example D-1-5, 3-dodecyl pentadecanoate was obtained by the same method as that described in Production Example D-1-5.

As starting compounds, using tridecanoic acid instead of the decanoic acid described in Production Example D-1-1, also using 1-bromododecane instead of the 1-bromononane described in Production Example D-1-2, and using the compound produced in each step in the subsequent step, 3-dodecyl pentadecanoate was synthesized by the same methods as those described in Production Examples D-1-1 to D-1-5.

colorless solid; FT IR (neat) 2928, 2854, 1709 cm$^{-1}$; $^1$H NMR (300 MHz in CDCl$_3$) δ0.88 (6H, t, J=6.6 Hz), 1.26 (44H, m), 1.85 (1H, m), 2.27 (2H, d, J=6.9 Hz); $^{13}$C NMR (75 MHz in CDCl$_3$) δ14.15, 22.72, 26.51, 29.39, 29.68, 29.71, 29.88, 31.96, 33.78, 34.86, 39.00, 180.00; CIMS m/z (%) 410 (M$^+$); HRMS (CI$^+$) m/z calcd for C$_{27}$H$_{54}$O$_2$(M$^+$) 410.4066, Found 410.4095.

Production Example D-6

Synthesis of 3-tetradecyl heptadecanoate

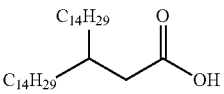

[Formula 62]

As starting compounds, using pentadecanoic acid instead of the decanoic acid described in Production Example D-1-1, also using 1-bromotetradecane instead of the 1-bromononane described in Production Example D-1-2, and using the compound produced in each step in the subsequent step, 3-tetradecyl heptadecanoate was synthesized by the same methods as those described in Production Examples D-1-1 to D-1-5.

colorless solid; FT IR (neat) 2915, 2849, 1704 cm$^{-1}$; $^1$H NMR (300 MHz in CDCl$_3$) δ0.88 (6H, t, J=6.9 Hz), 1.26 (52H, m), 1.85 (1H, m), 2.27 (2H, d, J=6.9 Hz); $^{13}$C NMR (75 MHz in CDCl$_3$) δ14.15, 22.73, 26.52, 29.41, 29.73, 29.90, 31.96, 33.78, 34.88, 38.99, 179.72; CIMS m/z (%) 466 (M$^+$); HRMS (CI$^+$) m/z calcd for C$_{31}$H$_{62}$O$_2$(M$^+$) 466.4685, Found 466.4717.

[Synthesis of Other Compounds]

The compounds of Examples 16 to 22 were obtained by the same manner as in the above described production examples. These are compounds wherein, in the formula (1) of the present invention, X, X', n and n' are as shown in Table 1 below.

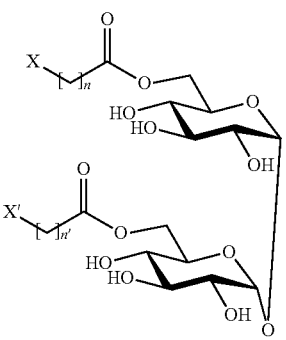

[Formula 63]

(Formula 1)

TABLE 1

|  | X | n | X' | n' |
|---|---|---|---|---|
| Example 16 | Phenyl | 0 | Phenyl | 0 |
| Example 17 | Naphthyl | 0 | Naphthyl | 0 |
| Example 18 | Cyclohexyl | 0 | Cyclohexyl | 0 |
| Example 19 | Cycloheptyl | 0 | Cycloheptyl | 0 |
| Example 20 | CH(C$_{14}$H$_{29}$C$_{16}$H$_{33}$) | 0 | CH(C$_{14}$H$_{29}$C$_{16}$H$_{33}$) | 0 |
| Example 21 | C$_{14}$H$_{29}$ | 0 | C$_{14}$H$_{29}$ | 0 |
| Example 22 | C$_{16}$H$_{33}$ | 0 | C$_{16}$H$_{33}$ | 0 |
| Example 23 | CH(C$_{12}$H$_{24}$OCH$_3$)$_2$ | 0 | CH(C$_{12}$H$_{24}$OCH$_3$)$_2$ | 0 |
| Example 24 | CH(C$_{13}$H$_{26}$OH)$_2$ | 0 | CH(C$_{13}$H$_{26}$OH)$_2$ | 0 |

[Measurement of Physiological Activity]

The following test was carried out on the compound of the present invention, so as to measure its activity.

With regard to the compounds of the present invention, which are described in Examples, Example numbers, Production Example numbers, and chemical structure formulae thereof are shown in Table 2 below. The compounds described in Examples are all the compound represented by the formula (1) of the present invention, and in the formula (1), X, X', $R_1$, $R_1'$, $R_2$, $R_2'$, n and n' are as shown in Table 2 below.

[Formula 64]

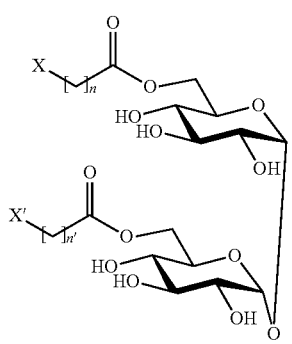

(Formula 1)

TABLE 2

| Example | Production Example | X: $R_1$—$CHR_2$— X': $R_1'$—$CHR_2'$— | | n and n' |
|---|---|---|---|---|
| | | $R_1$ and $R_1'$ | $R_2$ and $R_2'$ | |
| 2 | α-2 | n-$C_8H_{17}$ | n-$C_8H_{17}$ | 0 |
| 3 | α-3 | n-$C_9H_{19}$ | n-$C_9H_{19}$ | 0 |
| 1 | α-1 | n-$C_{10}H_{21}$ | n-$C_{10}H_{21}$ | 0 |
| 4 | α-4 | n-$C_{11}H_{23}$ | n-$C_{11}H_{23}$ | 0 |
| 5 | α-5 | n-$C_{12}H_{25}$ | n-$C_{12}H_{25}$ | 0 |
| 6 | α-6 | n-$C_{13}H_{27}$ | n-$C_{13}H_{27}$ | 0 |
| 7 | α-7 | n-$C_{15}H_{31}$ | n-$C_{15}H_{31}$ | 0 |
| 8 | α-8 | n-$C_{16}H_{33}$ | n-$C_{16}H_{33}$ | 0 |
| 15 | β-2 | n-$C_8H_{17}$ | n-$C_8H_{17}$ | 1 |
| 9 | β-1 | n-$C_9H_{19}$ | n-$C_9H_{19}$ | 1 |
| 10 | β-3 | n-$C_{10}H_{21}$ | n-$C_{10}H_{21}$ | 1 |
| 11 | β-4 | n-$C_{11}H_{23}$ | n-$C_{11}H_{23}$ | 1 |
| 12 | β-5 | n-$C_{12}H_{25}$ | n-$C_{12}H_{25}$ | 1 |
| 13 | β-6 | n-$C_{13}H_{27}$ | n-$C_{13}H_{27}$ | 1 |
| 14 | β-7 | n-$C_{14}H_{29}$ | n-$C_{14}H_{29}$ | 1 |

In the test, a known natural compound derived from tubercle *bacillus*, TDCM, was used as a positive control. It is to be noted that TDCM is represented by the following chemical formula.

[Formula 65]

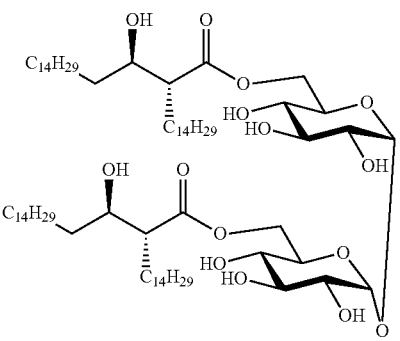

Test Example 1

Measurement of Ability to Activate Macrophages

Test Example 1

(1) Measurement of Active Oxygen Released from Mouse Intraperitoneal Macrophages Using Fluorescence Intensity Measurement Apparatus <Preparation of Phosphate Buffer (PBS)>

8.0 g of sodium chloride, 0.2 g of potassium chloride, 1.15 g of disodium hydrogen phosphate, and 0.2 g of potassium dihydrogen phosphate were dissolved in 1000 ml of distilled water (D.W.).

<Preparation of Mouse Intraperitoneal Macrophages>

3 ml of 5% thioglycolate medium (Difco, BD, code. 225640, Lot. 6192372) was administered into the abdominal cavity of a mouse (ICR mouse (SPF), 5-week-old, male). Four days after the administration, the mouse was sacrificed with the use of diethyl ether. The epidermis in the center of abdomen was partially cut with scissors, and thereafter, the abdomen was picked up and the epidermis thereof was then peeled off. Thereafter, using a 10-ml syringe equipped with a 26G needle, 5 ml of 0.05% EDTA-containing PBS (−) (EDTA 2Na, nuclease and protease tested, Nacalai Tesque) was totally injected into the abdominal cavity. Thereafter, the abdomen was massaged about 40 to 50 times by picking up the side of the abdomen. Using a 23G injection needle, liquid in the abdominal cavity was slowly collected into a small centrifuge tube. This operation was repeatedly carried out two times. The collected microphages were centrifuged at 1000 rpm for 8 minutes. The supernatant was discarded, and the precipitate was then suspended in an RPMI 1640 medium (RPMI-1640 containing L-glutamine and phenol red, Wako, 189-02025, Lot. WRM8043, which contained 10.61% inactivated serum (Bio West) and 1% *penicillin streptomycin* (GIBCO)). The centrifuge tube was filled with the RPMI 1640 medium, and it was then centrifuged again at 1000 rpm for 8 minutes. The supernatant was discarded, and the precipitate was then suspended in an RPMI 1640 medium. Thereafter, the number of macrophages was counted with One Cell Counter (Wakenyaku Co., Ltd.). The obtained macrophages were diluted with an RPMI-1640 medium to have any given concentration. The thus obtained mouse intraperitoneal macrophages were used in the subsequent test.

<Preparation of 40 mM Test Compound Solution>

A 40 mM test compound solution was prepared as follows.

0.7 g of BSA was weighed into a large test tube. Then, 10 ml of sterilized PBS (−) was added to the test tube, and the obtained mixture was fully stirred. Thereafter, using an LPS removal column (Endo Trap (trademark) red 1/1 (proofs)), impurities were removed from the BSA solution. Thereafter, the thus treated BSA solution was filtrated through a sterile filter (0.2 μm). Subsequently, protein was quantified using Nano Drop ND-1000, and it was then diluted with sterilized PBS (−) so as to result in a final concentration of 2%. The weighed test compound and 250 μl of 2% BSA (prepared by dissolving 2% BSA in PBS (−)) were placed in a homogenizer, and they were then treated with a bath type ultrasonicator for 150 seconds, while they were placed in the homogenizer. The thus prepared solution was transferred into an Eppendorf tube, and was then used in the subsequent test. A positive control was prepared using TDCM as a test compound in the same manner as described above. A negative control was prepared without adding test compounds in the same manner as described above. Hereinafter, a prepared solution, which contains no test compounds, is referred to as a "vehicle."

<Preparation of Hank's Balanced Salt Solution (HBS)>

0.4 g of potassium chloride, 0.06 g of potassium dihydrogen phosphate, 0.107 g of disodium hydrogen phosphate, and 8 g of sodium chloride were dissolved in distilled water (D.W.), and the solution was adjusted to pH 7.4 with 1 N sodium hydroxide, and the total amount of the solution was adjusted to 1000 ml with distilled water (D.W.), so as to prepare a Hank's balanced salt solution (HBS).

<Preparation of Glucose- and BSA-Containing Hank's Balanced Salt Solution (HBSG-BSA)>

0.1 g of glucose and 0.03 g of BSA (Sigma) were dissolved in 100 ml of the above prepared HBS, so as to prepare a glucose- and BSA-containing Hank's balanced salt solution (HBSG-BSA) (prepared when used).

<Measurement of Active Oxygen Released from Macrophages>

Mouse intraperitoneal macrophages, a 40 mM test compound solution, and a BSA-containing Hank's balanced salt solution (HBSG-BSA) were prepared in the same manner as described above.

After the macrophages had been washed with HBSG-BSA, they were then suspended in approximately 5 mL of HBSG-BSA, and 100 of the obtained suspension was then dispensed into each well of a 96-well Collagen Well (TC-PLATE 96 WELL, STERILE WITH LID, IND PACKED). Thereafter, it was incubated at 37° C. for 1 hour, so that the cells were adhered to the well. The supernatant was removed, and 100 μl of HBSG-BSA was then added to the residue. Then, 1 μl of 10 mM H$_2$DCFDA (2',7'-dichlorodihydrofluorescein diacetate, Invitrogen) was added to the reaction solution. The reaction solution was incubated at 37° C. for 1 hour. The supernatant was removed, and HBSG-BSA that contained a test compound or a vehicle used as a negative control was added to the residue, so that the final concentration of the test compound could be 50 μM. One hour later, the amount of active oxygen was measured using Genios fluorescence intensity measurement apparatus.

The above-mentioned H$_2$DCFDA is a fluorescent probe, and its fluorescence intensity is increased in the presence of hydrogen peroxide (H$_2$O$_2$). Thus, by measuring such fluorescence intensity, the amount of hydrogen peroxide (H$_2$O$_2$) generated can be measured. Hydrogen peroxide (H$_2$O$_2$) is derived from superoxide (O$^{2-}$) generated by macrophages, and thus, using the amount of hydrogen peroxide (H$_2$O$_2$) generated as an indicator, the activation level of macrophages can be measured.

The measurement results are shown in FIG. 1.

FIG. 1 <Amount of Active Oxygen from Mouse Intraperitoneal Macrophages>

As shown in FIG. 1, all of the test compounds of the present invention exhibited action to promote the generation of active oxygen from mouse intraperitoneal macrophages, at a level equivalent to or higher than that of TDCM. Among the test compounds of the present invention, in particular, the compound of Example 1 and the compound of Example 9 exhibited high activity that was two times higher than the activity of TDCM.

Test Example 1

(2)

<Measurement of Phagocytic Ability of Mouse Intraperitoneal Macrophages>

Mouse intraperitoneal macrophages, a 40 mM test compound solution, and an RPMI1640 medium were prepared in the same manner as described above.

In the following experiment, Fluoresbrite (trademark) Carboxylate Microspheres (2.58% Solids-Latex) YG (Polysciences, Inc.) were used as fluorescent beads.

Macrophages were added to a TC-Plate (TC-PLATE 24 WELL, STERILE WITH LID, IND PACKED, greiner bio-one), so that they became 80% confluent. The macrophages were incubated at 37° C. for 2 hours. Thereafter, the supernatant was discarded, and the cells were then washed with 500 μl of RPMI 1640 medium two times. Each composition shown in Table 3 below was added to the TC-Plate, and it was then incubated at 37° C. for 2 hours. Thereafter, the supernatant was discarded, and the cells were then washed with 300 μl of sterilized PBS (−). In order to remove fluorescent beads that had not been incorporated into the cells, the aforementioned washing operation was repeatedly carried out two times. Macrophages were peeled off with 200 μl of sterilized PBS (−), and were then transferred into an Eppendorf tube. The macrophages were centrifuged at 1,500 rpm for 8 minutes. Thereafter, the supernatant was removed, and the residue was then fully suspended in 100 μl of sterilized PBS (−). The suspension was again centrifuged at 1,500 rpm for 8 minutes. Thereafter, the supernatant was removed, and the residue was then fully suspended in 100 μl of sterilized PBS (−).

Using FUJI FILM FLA-2000, the amount of fluorescent beads incorporated into the cells was measured [fluorescence intensity (Fluor 473 nm, Y520 Filter)]. For analysis, Image Reader V1.4J was used.

TABLE 3

|  | 1 | 2 |
|---|---|---|
| Test compound (final concentration: 50 μM) | — | 0.45 |
| LPS (—) 2% BSA in PBS | 0.45 | — |
| Fluorescent beads (2.0 × 10$^7$ beads/mL) | 100 | 100 |
| RPMI 1640 medium | 199.5 | 199.5 |

Figure 2:
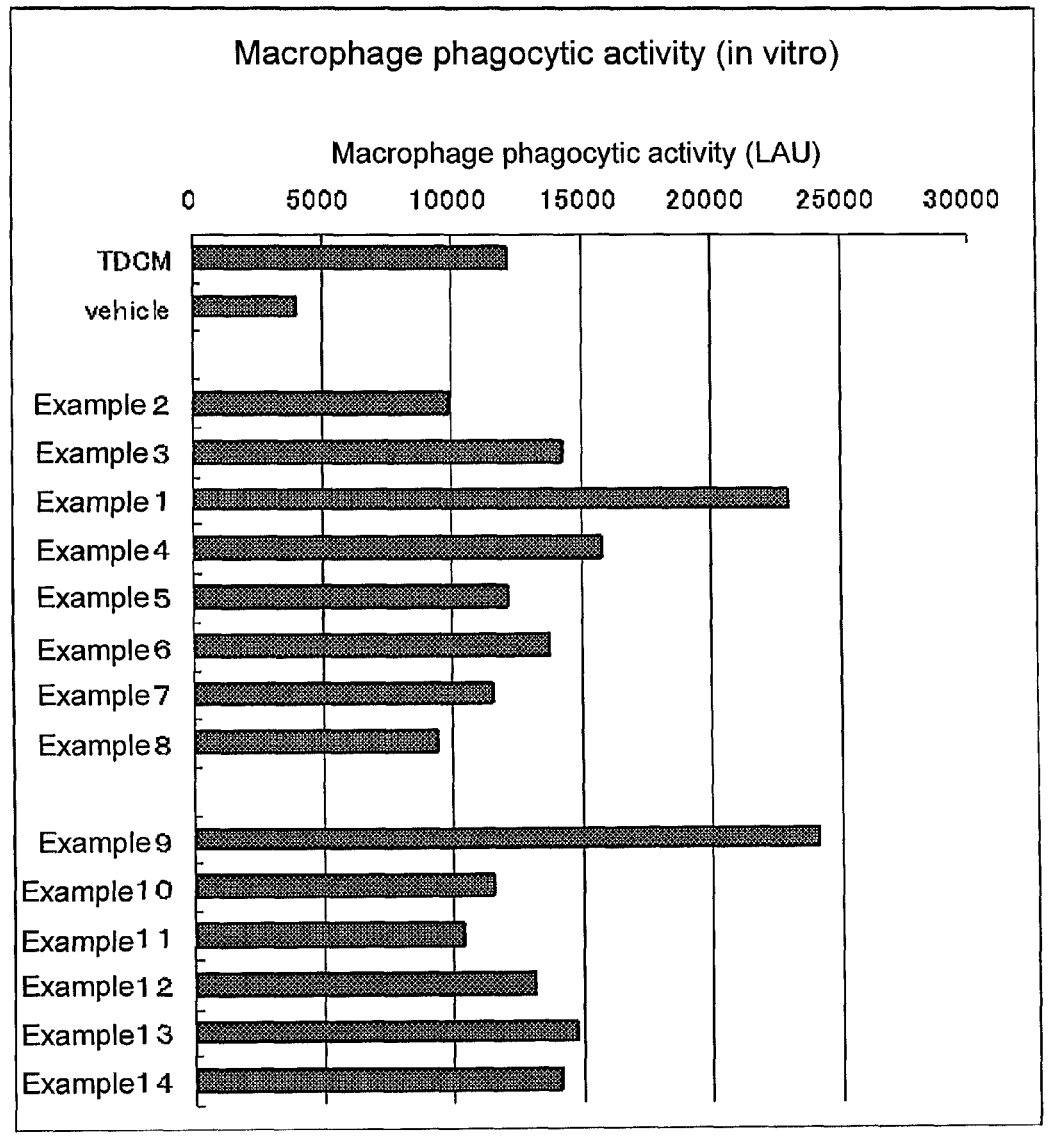
FIG. 2 shows the phagocytic ability of mouse intraperitoneal macrophages in a case in which TDCM, a vehicle or the test compound of the present invention was allowed to act on the mouse intraperitoneal macrophages.

The measurement results are shown in FIG. 2.

FIG. 2 <Phagocytic Ability of Mouse Intraperitoneal Macrophages>

As shown in FIG. 2, all of the test compounds of the present invention exhibited action to activate the phagocytosis of mouse intraperitoneal macrophages, at a level equivalent to or higher than that of TDCM. Among the test compounds of the present invention, in particular, the compound of Example 1 and the compound of Example 9 exhibited high activity that was approximately two times higher than the activity of TDCM.

Test Example 2

Measurement of Ability to Activate Neutrophils

<Preparation of Rabbit Neutrophil Suspension>
A Hank's balanced salt solution (HBS) and a glucose- and BSA-containing Hank's balanced salt solution (HBSG-BSA) were prepared in the same manner as that in Test Example 1 (1).
<Preparation of Citric Acid-Glucose Solution (ACD Solution)>
6.25 g of sodium citrate, 3.125 g of citric acid, and 5 g of glucose were dissolved in 250 ml of distilled water (D.W.), and the obtained solution was preserved at 4° C. before use.
<Preparation of Erythrolysis Solution (Lysis Solution)>
0.037 g of EDTA, 1 g of potassium hydrogen carbonate, and 8.3 g of ammonium chloride were dissolved in 1000 ml of distilled water (D.W.), and the obtained solution was preserved at 4° C. before use.
<Preparation of Phosphate Buffer (PBS)>
A phosphate buffer was prepared in the same manner as that in Test Example 1 (1).
<Preparation of 1.2% Dextran-PBS Solution>
1.2 g of dextran T500 (Pharmacia) was dissolved in 100 ml of distilled water (D.W.), and the obtained solution was then sterilized in an autoclave (121° C., 20 minutes). The solution was preserved at 4° C. before use.
<Method for Preparing Rabbit Neutrophil Suspension>
5 ml of the ACD solution was placed in a 20-ml syringe (injection needle [Nipro]), so that the inside of the syringe was entirely rinsed therewith. 20 ml of blood was collected from the central auricular artery of a rabbit using the syringe, and the collected blood was gently shaken upside down. Thereafter, the blood was dispensed into three centrifuge tubes (15 ml type; Falcon), and each tube was then subjected to centrifugation at 4° C. at 1,500 rpm for 5 minutes. Thereafter, the supernatant was recovered into a centrifuge tube (50 ml type; Falcon). A 1.2% dextran-PBS solution was added to the recovered supernatant in an amount equal the supernatant, and the obtained mixture was then gently shaken upside down. Thereafter, the mixture was left at a room temperature for 30 minutes or more. The emergence of an interface was confirmed, and the supernatant was placed in a new centrifuge tube (50 ml type; Falcon). A 1.2% dextran-PBS solution was added to the remaining solution in an amount equal the remaining solution, and the obtained mixture was then gently shaken upside down. Thereafter, the mixture was left at a room temperature for 30 minutes or more. The emergence of an interface was confirmed, and the supernatant was placed in a new centrifuge tube (50 ml type; Falcon). The recovered supernatant was centrifuged at 4° C. at 2,000 rpm for 10 minutes, and the supernatant was then removed. 15 ml of the Lysis solution was added to the precipitate, and the obtained mixture was then gently suspended. Thereafter, 5 ml of the Lysis solution was further added to the suspension, and the obtained mixture was then gently shaken upside down. The reaction solution was left in ice for 5 minutes. Thereafter, HBSG-BSA was added to the reaction solution to a total amount of 50 ml, and the obtained solution was then centrifuged at 4° C. at 2,000 rpm for 10 minutes, followed by the removal of the supernatant. The precipitate was suspended in 2 ml of HBSG-BSA, and the obtained cell suspension was gently laminated on an upper layer of 2 ml of Lymphoprep [Nycomed, 808068] (centrifuge tube, 15 ml type). It was then centrifuged at 1200 rpm for 20 minutes (conditions of the centrifugal machine: accel 0.5, break Off), and the supernatant was then removed using an aspirator. In order to remove the remaining Lyphoprep, the precipitate (neutrophils) was suspended in HBSG-BSA, and it was then centrifuged again at 1,500 rpm for 5 minutes. Then, the supernatant was removed. The neutrophils were suspended in HBSG-BSA, and the number of cells was then counted using a cell number counting machine "Celltac" [Nihon Kohden Corporation].
<Preparation of Emulsion Solution of Test Compound>
An emulsion solution of a test compound and an emulsion solution of TDCM were prepared in the same manner as that in Test Example 1 (1).
<Preparation of 10 mM $H_2$DCFDA (2',7'-dichlorodihydrofluorescein diacetate (Molecular Probes)>
4.86 mg of $H_2$DCFDA was dissolved in 1 ml of DMSO.

Test Example 2(1)

Figure 3:
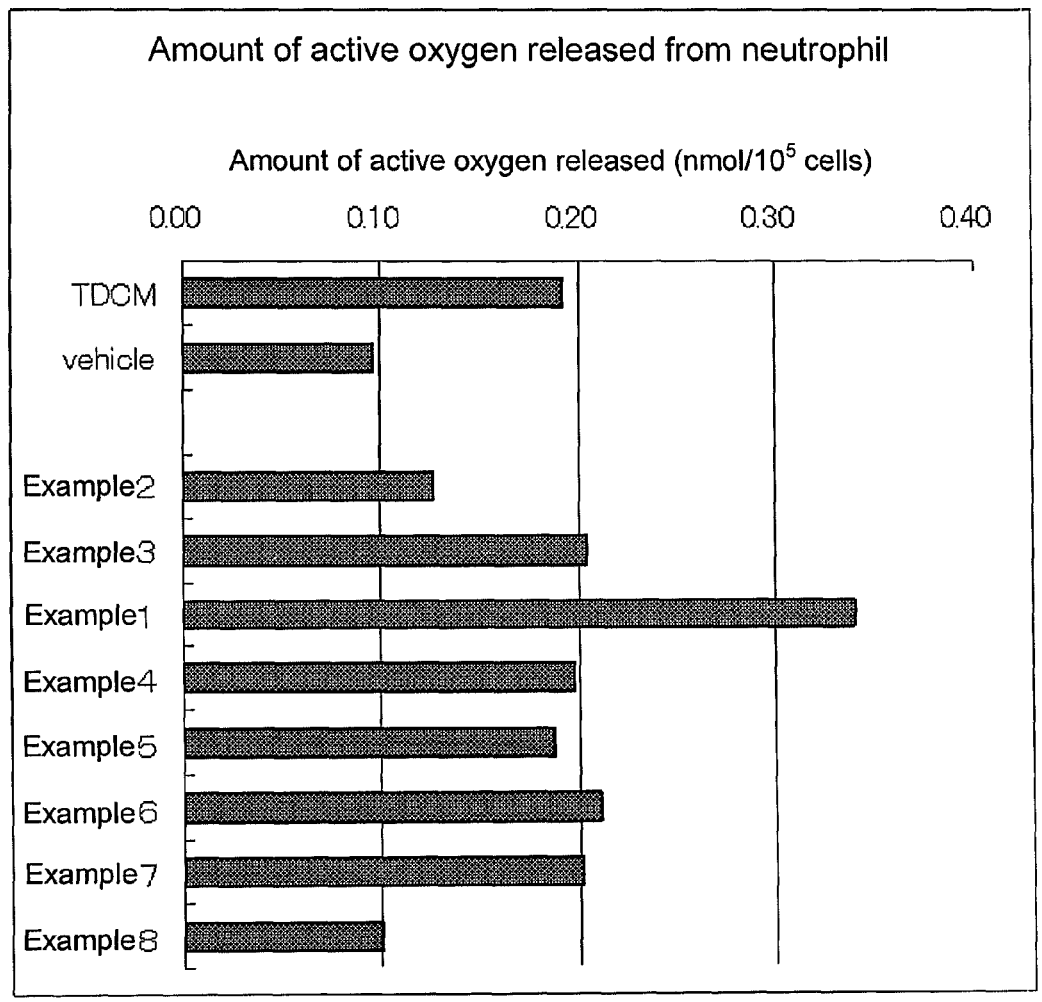
FIG. 3 shows the amount of active oxygen released from rabbit neutrophils in a case in which TDCM or the test compound of the present invention was allowed to act on the rabbit neutrophils.

<Measurement of Amount of Active Oxygen Released from Rabbit Neutrophils>
The influence of the test compound on the release of active oxygen from rabbit neutrophils was measured by the following procedures.
Neutrophils ($1.0 \times 10^5$ cells/100 µl) were plated on a 96-well plate (Falcon). To this plate, 1 µl of 10 mM $H_2$DCFDA was added, and it was then incubated at 37° C. for 1 hour. In order to remove residual $H_2$DCFDA, 300 µl of HBS was added to the reaction product so as to suspend it, and the obtained suspension was then centrifuged at 8000 rpm for 5 minutes. The supernatant was removed, and the residue was then suspended in HBS. Then, HBS was added to the suspension to a final concentration of 50 µM. The obtained mixture was incubated at 37° C. for 2 hours, and the amount of active oxygen released was measured using a fluorescence measurement apparatus (Ex: 485 nm, Em: 535 nm).
The results are shown in FIG. 3.
FIG. 3 <Amount of Active Oxygen Released from Rabbit Neutrophils>
As shown in FIG. 3, almost of the test compounds of the present invention exhibited action to activate the release of active oxygen from rabbit neutrophils, at a level equivalent to or higher than that of TDCM. Among the test compounds of the present invention, in particular, the compound of Example 1 exhibited the activity was approximately two times higher than the activity of TDCM.

Test Example 2(2)

<Measurement of Phagocytic Ability of Rabbit Neutrophils>
(2) Method for Producing Ampicillin-Resistant *Escherichia coli* and Opsonized *Escherichia coli*
<Preparation of L-Broth>
10 g of tryptophan, 5 g of NaCl, 5 g of Yeast Extract, and 1 ml of $MgSO_4$ were dissolved in 1 L of distilled water (D.W.).
<Preparation of Opsonizing Reagent>
10 mg of an opsonizing reagent (BioParticles Opsonizing Reagent (Molecular Probes)) was dissolved in 500 µl of ultrapure water.
<Production of Ampicillin-Resistant *Escherichia coli*>
Cells (JM109) used for electroporation were dissolved in ice, and in order to introduce an ampicillin-resistant gene into *Escherichia coli*, 2 µl of an ampicillin-resistant plasmid (pT7Blue, Novagen, 100 ng/μl) was added to the JM109, followed by suspension. The obtained suspension was transferred to a cuvette used for electroporation, and it was then pulsed (2.5 kV, 200Ω, 25 mF). The pulsed cell mass solution was transferred into a 5-ml tube containing 1 ml of L-broth medium, and it was then cultured at 37° C. for 3 hours. The resultant solution was applied to a L-broth agar medium containing 0.005% ampicillin, and it was then cultured at 37° C. overnight (wherein, before the solution was dispersed on the medium, it was centrifuged at 3,500 rpm for 5 minutes, 800 μl of the supernatant was removed, the precipitate was then suspended, and the suspension was then dispersed on a petri dish). On the following day, a small amount of bacteria growing from the petri dish was scraped off, and it was then dissolved in 2 ml of L-broth medium, followed by a shaking culture for approximately 4 hours.

<Method for Producing Opsonized *Escherichia coli*>

100 μl of the above produced ampicillin-resistant *Escherichia coli* solution and 100 μl of the dissolved opsonizing reagent were suspended in an Eppendorf tube. The obtained suspension was incubated at 37° C. for 1 hour, and it was then suspended in 300 μl of PBS. The suspension was centrifuged at 1200 G for 15 minutes, and the supernatant was then removed. The obtained solution was further suspended in 300 μl of PBS, and the suspension was then centrifuged at 1200 G for 15 minutes, followed by the removal of the supernatant. This operation was repeatedly carried out two times. Thereafter, 1 μl of the cell solution was added to 100 μl of L-broth, and it was fully suspended. Then, the suspension was 100-fold diluted. The thus 100-fold diluted cell solution was added to 10-μl OneCell Counter, and the number of cells was then counted under a microscope.

<Measurement of Phagocytic Ability of Rabbit Neutrophils>

$1.0 \times 10^5$ neutrophils prepared by the above described method were fractionated into an Eppendorf tube, and the cells were then suspended in HBS. Thereafter, it was treated with an emulsion solution of a 50-μM test compound or an emulsion solution of TDCM for 1 hour. Using a 2% BSA solution as a control, and the same treatment as described above was performed on the neutrophils. 300 μl of HBS was added to the reaction solution so as to suspend it, and the obtained suspension was then centrifuged at 1200 G for 10 minutes, followed by the removal of the supernatant. Further, 300 μl of HBS was added to the obtained solution so as to suspend it, and the obtained suspension was then centrifuged at 1200 G for 10 minutes, followed by the removal of the supernatant. $1.0 \times 10^7$ cells of opsonized ampicillin-resistant *Escherichia coli* were fully suspended in the treated neutrophils, and the obtained suspension was then incubated at 37° C. for 1 hour. After the removal of residual *Escherichia coli*, 100 μl of 0.5% Triton X-100 (in a normal saline solution) was added to the residue, and it was then fully suspended therein. The obtained suspension was incubated at 37° C. for 30 minutes. Subsequently, in order to comparatively quantify the amount of *Escherichia coli* incorporated into the inside of the neutrophils by disintegrating the neutrophils by a treatment with Triton X-100, the Triton X-100-treated solution as a whole was dispersed on a 0.005% ampicillin-containing common agar medium, and it was then spread with the use of a bacteria spreader. Thereafter, it was incubated at 37° C. for 24 hours, and the number of colonies of *Escherichia coli* incorporated into the neutrophils was counted.

Figure 4:
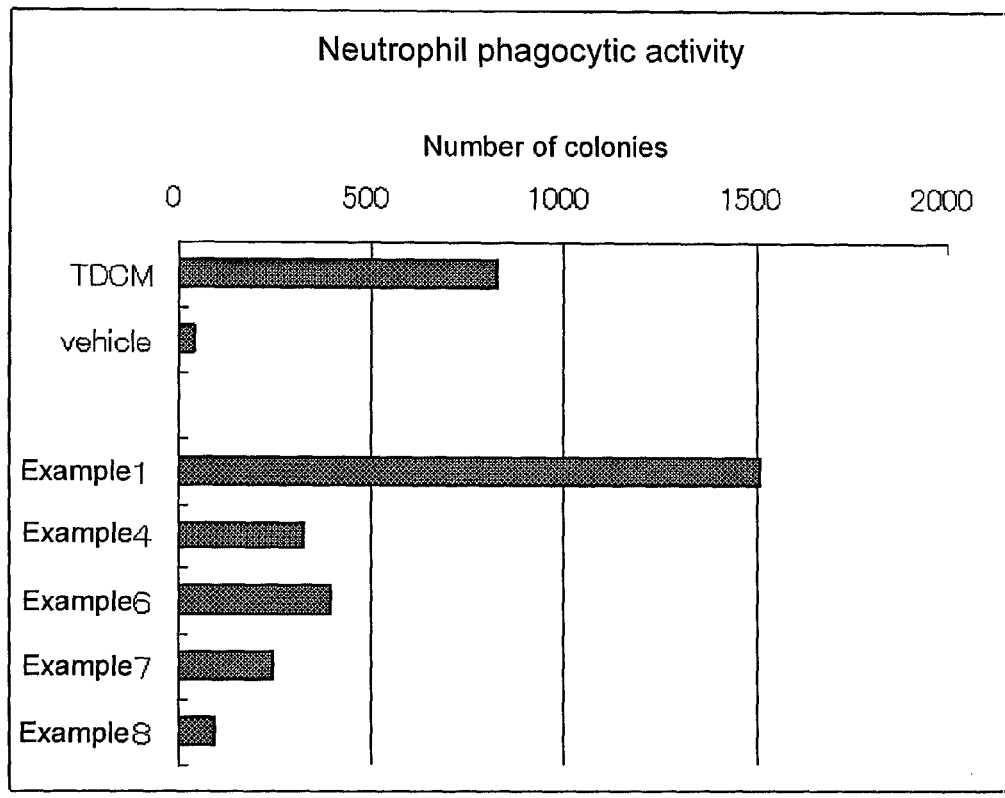
FIG. 4 shows the phagocytic ability of rabbit neutrophils in a case in which TDCM or the test compound of the present invention was allowed to act on the rabbit neutrophils.

The results are shown in FIG. 4.

FIG. 4 <Phagocytic Activity of Rabbit Neutrophils>

As shown in FIG. 4, all of the compounds of the present invention exhibited action to activate the phagocytic ability of rabbit neutrophils. Among the compounds of the present invention, in particular, the compound of Example 1 exhibited the activity that was approximately 2 times higher than that of TDCM.

Test Example 3

<Measurement of Cytokine Released from Mouse Intraperitoneal Macrophages by Treatment with Test Compound>

Mouse intraperitoneal macrophages, a 40 mM test compound solution, and an RPMI 1640 medium were prepared in the same manner as described above.

Macrophages were added to a TC-Plate, so that they became 80% confluent. The macrophages were incubated at 37° C. for 2 hours. Thereafter, the supernatant was discarded, and the cells were then washed with 500 μl of RPMI 1640 medium. This washing operation was repeatedly carried out two times. An emulsion solution of the test compound (final concentration: 100 μM) was allowed to act on the macrophages, and two hours later, the medium was transferred into another Eppendorf tube. It was centrifuged at 10,000 rpm for 10 minutes, and the supernatant was further transferred into another Eppendorf tube. This supernatant was used as a sample, and the released cytokines were analyzed using ELISA kit (IL-6, TNF-α Quantikine Immunoassay (R & D System (trademark)).

With regard to the release of IL-6 from mouse intraperitoneal macrophages, the amount of IL-6 released was approximately 15 pg/ml in the case of using a vehicle as a negative control. In contrast, the compound of Example 1, which seemed to have particularly high activity among the compounds of the present invention, exhibited an activity of approximately 200 pg/ml. Moreover, with regard to the release of TNF-α from mouse intraperitoneal macrophages, the amount of TNF-α released was approximately 80 pg/ml in the case of using a vehicle as a negative control. In contrast, the compound of Example 1 exhibited an activity of approximately 1000 pg/ml.

Test Example 4

<Method for Measuring IL-8 Released from THP-1 Cells, which Involves Treatment with Test Compound>

An RPMI medium solution was prepared in the same manner as described above. Using this medium solution, an RPMI medium solution of the test compound was prepared as follows.

1.0 mg of the test compound was dissolved in 25 μl of DMSO by an ultrasonic treatment for approximately 1 minute. The thus obtained 40 mM test compound stock solution was added to 100 μl of RPMI medium to a final concentration of 50 μM. The obtained mixture was treated with ultrasonic wave for 5 seconds. In the case of preparing the vehicle used as a control, instead of the 40 mM test compound stock solution, only the solvent was added in the same amount as described above to the RPMI medium, and it was then treated with ultrasonic wave for 5 seconds.

THP-1 cells (purchased from Cell Bank, RIKEN BioResource Center) were added to an RPMI medium to a cell density of $1.0 \times 10^6$ cells/100 μl and 100 μl each of the obtained solution was dispensed into a sterile Eppendorf tube. 100 μl of the RPMI medium solution of the test compound as prepared above was treated with ultrasonic wave for 5 seconds, and the total amount of the solution was then added to the Eppendorf tube, into which the cells had been dispensed. Two hours later, the reacted Eppendorf tube was centrifuged at 5000 rpm for 5 minutes, and the amount of IL-8 released into the supernatant was then measured using ELISA kit (human IL-8 ELISA kit (R & D Systems (trademark)).

Figure 5:
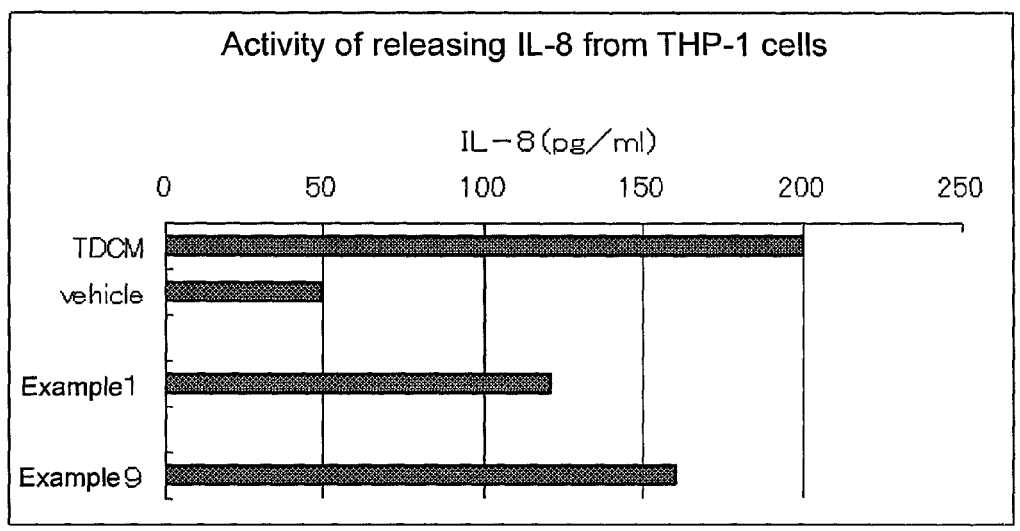
FIG. 5 shows the amount of IL-8 released from human-derived THP-1 cells in a case in which TDCM, a vehicle or the test compound of the present invention was allowed to act on the human-derived THP-1 cells.

The test results are shown in FIG. 5.

Among the compounds of the present invention, the compounds, which seemed to have particularly high immunostimulatory activity, were measured. As a result, as shown in FIG. 5, the compound of Example 1 and the compound of Example 9 exhibited activities that were approximately 0.6 times and approximately 0.8 times higher than the activity of TDCM, respectively.

Test Example 5

<Measurement of IL-6, TNF-α, and IFN-γ Released into Peripheral Blood of Test Compound Administered Mouse>

An emulsion solution of the test compound was prepared as follows.

Hereinafter, the term "test compound" is used to include all of compounds synthesized in Production Examples α-1 to -8, compounds synthesized in Production Examples β-1 to -7, and TDCM used as a comparative example.

A test compound was weighed (100 μg/mouse), and using a micro spatula, the total amount of the test compound was placed at the bottom of a homogenizer (WEATON U.S.A., 10 ml). A droplet of mineral oil (Nacalai Tesque) was added dropwise thereto, followed by homogenization. The obtained mixture was treated with a bath-type ultrasonic wave generator for 150 seconds. Thereafter, 1.0 ml of normal saline solution containing 1.1% Tween 80 (polyoxyethylene sorbitan monooleate, Nacalai Tesque) and 5.6% mannitol was further added to the homogenizer. The components were homogenized several times, so that the mineral oil, in which the test compound was dissolved, was well mixed with the solvent. The resultant solution was transferred into an Eppendorf tube, and it was then subjected to pasteurization at 62° C. for 30 minutes.

Homogenizers had previously been immersed in ice for 3 minutes. Various test compounds (1.0 mg each) were each placed in such a homogenizer, mineral oil was then added to the homogenizer, and the obtained mixture was treated with ultrasonic wave for 150 seconds. After confirming that the oil became sticky, 1.0 ml of normal saline solution (containing 1.1% Tween and 5.6% mannitol) was added to the homogenizer, and the obtained mixture was then homogenized for approximately 1 minute. The sample was transferred into an Eppendorf tube, and it was then subjected to pasteurization at 62° C. for 30 minutes.

The thus prepared emulsion solution of test compound (100 μg/mouse) was administered via an intravenous injection to a group of two mice. Two hours later, blood collected from the heart (heparin blood collection). The collected blood was centrifuged at 10,000 rpm for 10 minutes, and using only plasma, the amounts of various types of cytokines were measured using ELISA kit (IL-6, TNF-α, IFN-γ Quantikine Immunoassay (R & D Systems (trademark)).

Figure 6:
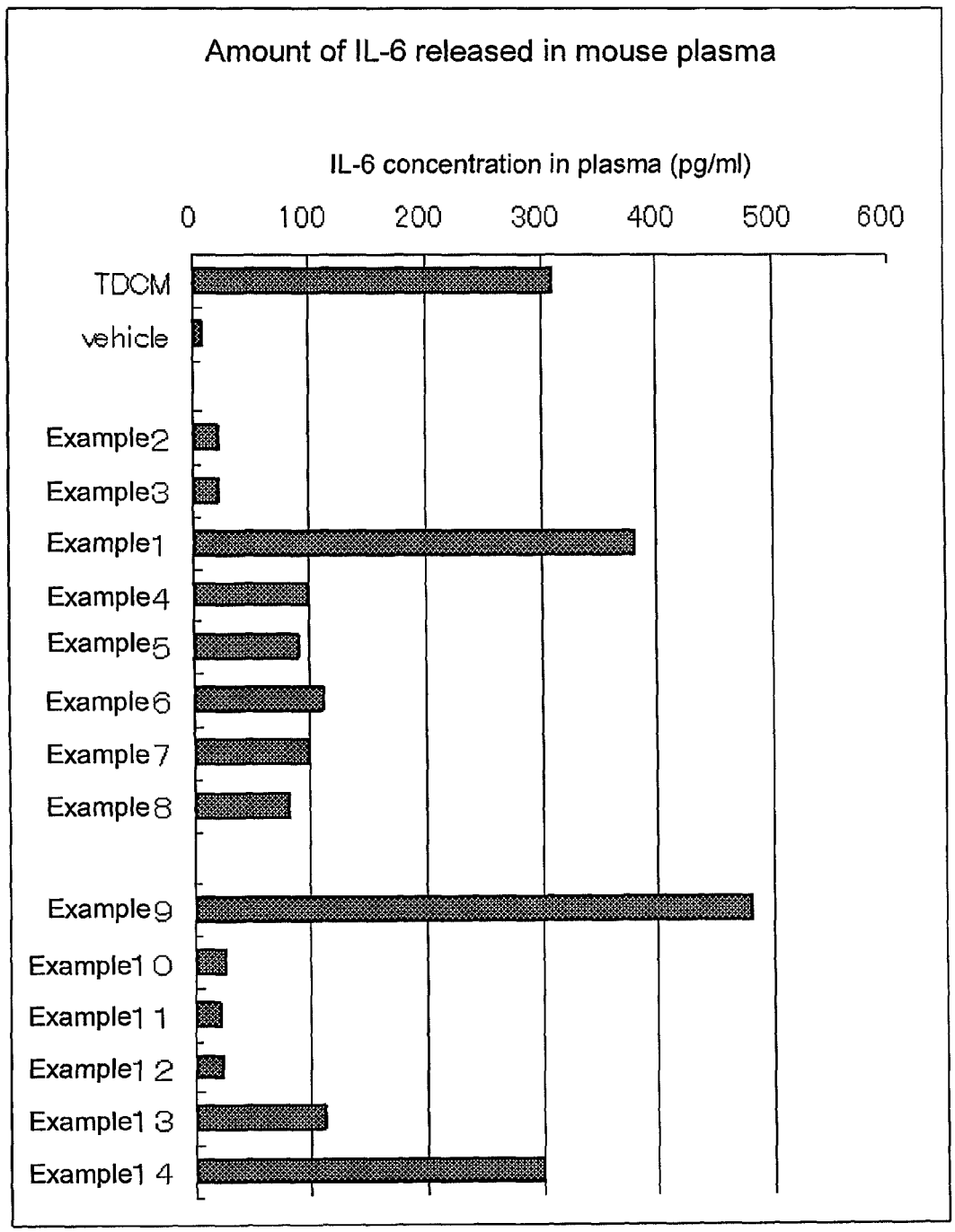
FIG. 6 shows the concentration of IL-6 in mouse plasma in a case in which TDCM, a vehicle or the test compound of the present invention was administered to mice.
Figure 7:
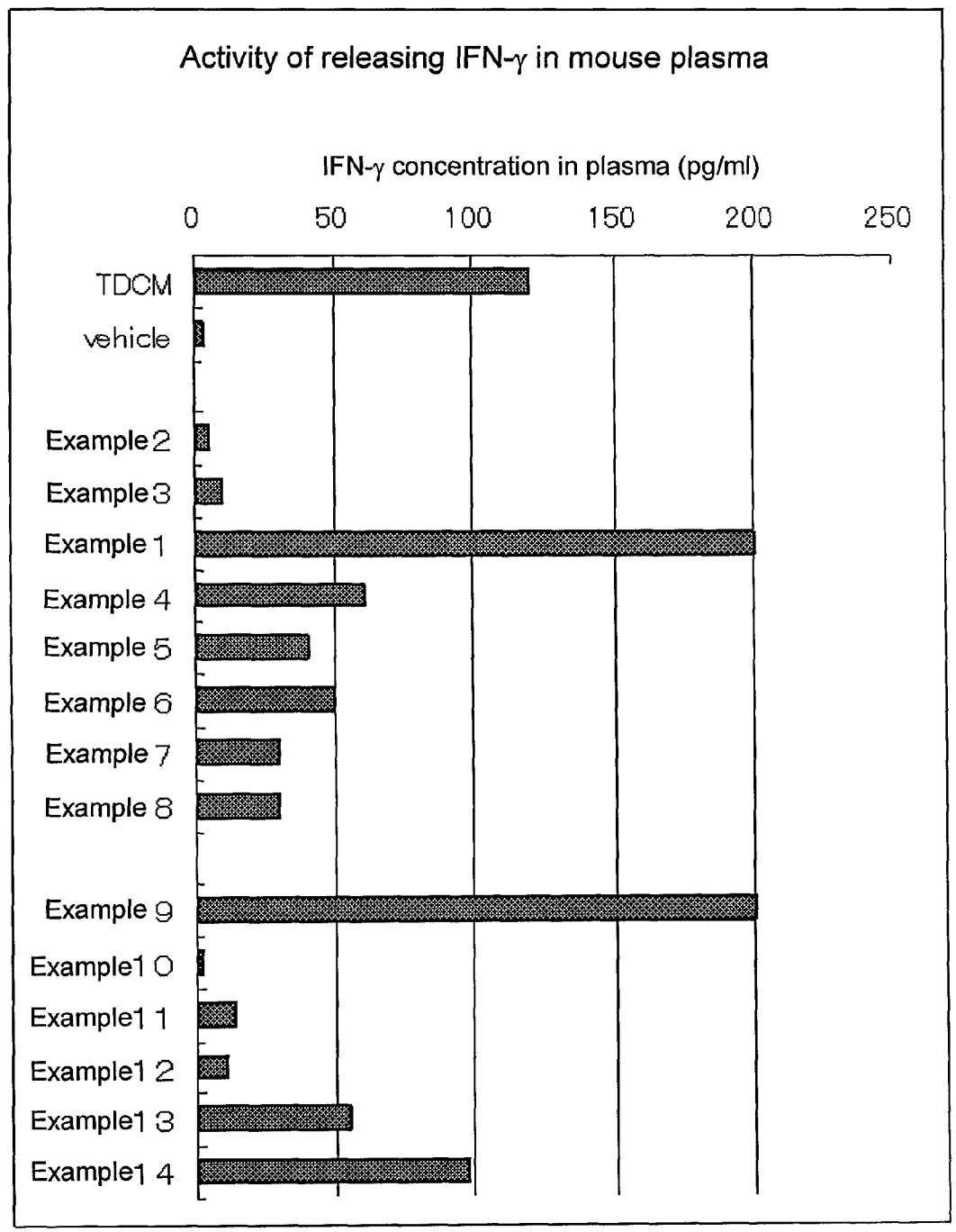
FIG. 7 shows the concentration of IFN-γ in mouse plasma in a case in which TDCM, a vehicle or the test compound of the present invention was administered to mice.
Figure 8:
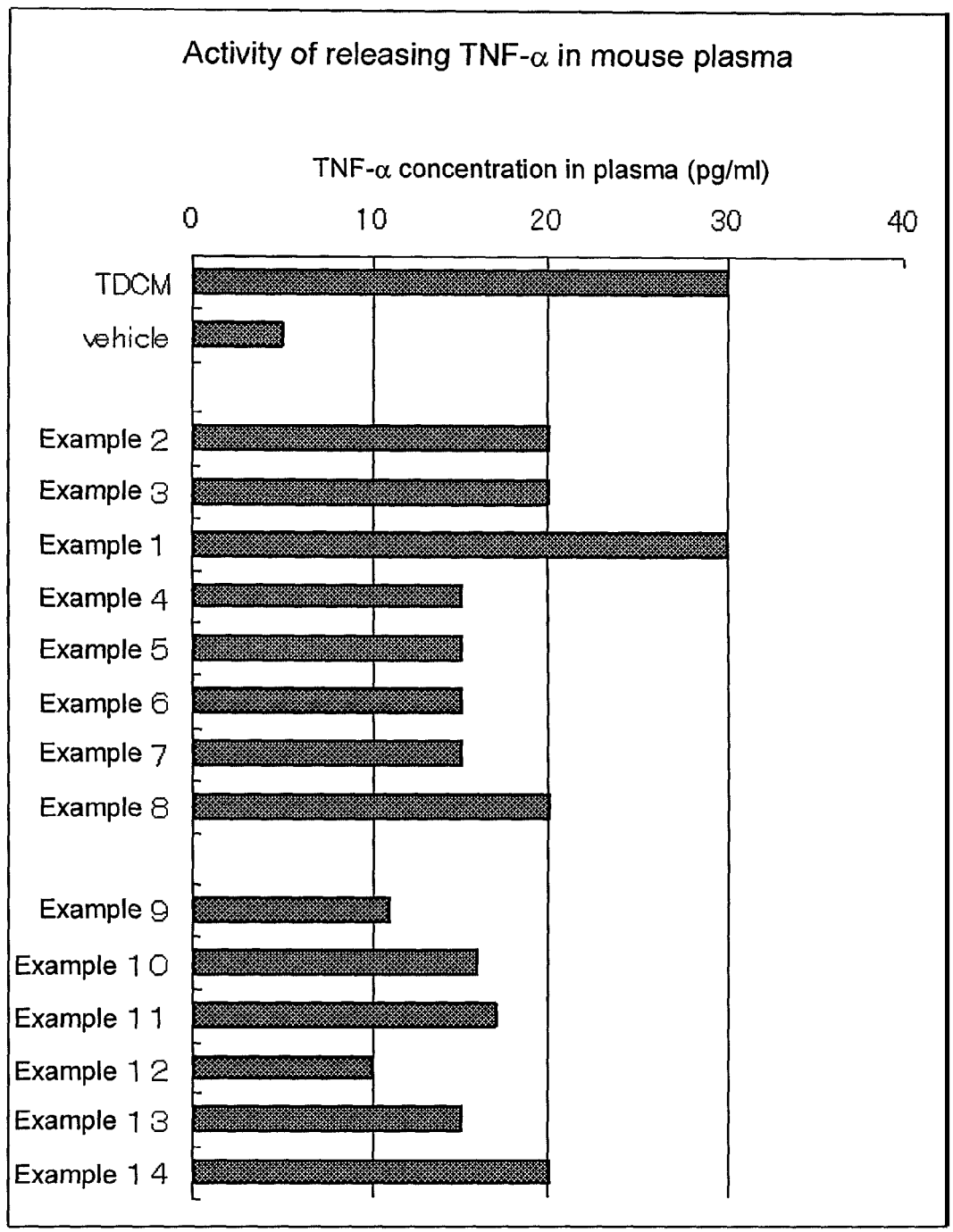
FIG. 8 shows the concentration of TNF-α in mouse plasma in a case in which TDCM, a vehicle or the test compound of the present invention was administered to mice.

The measurement results are shown in FIGS. 6, 7 and 8.

FIG. 6 <IL-6 concentration (pg/ml) in mouse plasma>

FIG. 7 <IFN-γ concentration (pg/ml) in mouse plasma>

FIG. 8 <TNF-α concentration (pg/ml) in mouse plasma>

As shown in FIG. 6, an increase in the plasma IL-6 concentration was observed in mice, to which the test compounds of the present invention had been administered. Among the test compounds of the present invention, in particular, the compound of Example 1 and the compound of Example 9 exhibited high IL-6-releasing activities, which were, respectively, approximately 1.2 times and approximately 1.5 times higher than that of TDCM as a known trehalose diester compound from nature, which was used as a positive control. The compound of Example 13 and the compound of Example 14 also exhibited activities, which were, respectively, approximately a half of and approximately equivalent to that of TDCM.

As shown in FIG. 7, an increase in the plasma IFN-γ concentration was observed in mice, to which the test compounds of the present invention had been administered. Among the test compounds of the present invention, in particular, the compound of Example 1 and the compound of Example 9 each exhibited IFN-γ-releasing activity, which was approximately 1.5 times higher than that of TDCM used as a positive control. The compound of Example 13 and the compound of Example 14 also exhibited activities, which were, respectively, approximately a half of and approximately equivalent to that of TDCM.

As shown in FIG. 8, an increase in the plasma TNF-α concentration was observed in mice, to which the test compounds of the present invention had been administered. However, even the activity of the compound of Example 1 was the same level as that of TDCM used as a positive control. Other compounds of the present invention generally exhibited approximately ½ of that of TDCM.

Test Example 6

<Mouse Survival Test Involving Administration of Welch bacillus (Compound of Example 1)>

As test compounds, 1 mg each of the compound synthesized by the method described in Production Example α-1 and TDCM were weighed. Emulsion solutions of the test compounds (1 mg/ml) were prepared in the same manner as described above.

Welch bacillus (Type A; NTCT8237) was prepared as follows.

<Method for Preparing Welch bacillus>

7.4 mg of Brain Heart Infusion (BHI) (Difco) powders were dissolved in 200 ml of distilled water. 40 ml of the obtained solution (hereinafter this solution is referred to as a "BHI medium") was withdrawn with a measuring pipette, and it was then added to a 200-ml flask, followed by performing a high-pressure steam sterilization (121° C., 20 minutes). In addition, 5 ml of the BHI medium was added to two screw-top test tubes, and they were then subjected to a high-pressure steam sterilization. Moreover, a glass tube-equipped rubber plug (with a cotton plug) and a glass tube were also subjected to a high-pressure steam sterilization. In a clean bench, an appropriate amount of bacteria for preservation, which had grown on a cooked meat medium, was collected with a sterilized Pasteur pipette, and it was then inoculated on the BHI medium in the aforementioned sterilized screw-top test tube. Subsequently, it was incubated at 37° C. overnight.

In a clean bench, bacteria that had grown in the screw-top test tube (wherein the inside of the clean bench in which bacteria had grown became clouded, and gas was generated) was transferred into a 200-ml Erlenmeyer flask, which contained 40 ml of BHI medium. A glass tube was inserted into the medium, so as to carry out nitrogen substitution for 10 minutes. Subsequently, the glass tube-equipped rubber plug (with a cotton plug) was equipped in the Erlenmeyer flask (since Welch bacillus generates gas, it is necessary to make an air vent), and incubation was then carried out at 37° C. for 4 to 5 hours. Thereafter, the cultured Welch bacillus was transferred into a centrifuge tube, it was then centrifuged (9000 rpm, 15 minutes), and the supernatant was then removed. 20 ml of sterilized normal saline solution was added to the precipitate, so that the bacteria were suspended therein. The suspension was centrifuged (9000 rpm, 15 minutes), and the supernatant was then removed. The obtained precipitate was added to the BHI medium in the sterilized screw-top test tube, and the number of cells was then counted using OneCell Counter (manufactured by OneCell Inc.).

<Method for Conducting Survival Test Involving Administration of Welch *bacillus*>

Mice (ICR, 6-week-old) were divided into three groups, and the following test was then carried out.

An emulsion solution containing the test compound, an emulsion solution containing TDCM, or an emulsion solution alone, which was to be used as a control, was intraperitoneally administered in an amount of 100 μg/mouse to a group of four mice (100 μl/mouse, in the case of the emulsion solution alone). Three hours later, Welch *bacillus* (2.4×10$^7$ cells/mouse) was intraperitoneally administered to the mice. Thereafter, the condition of the mice was observed.

The results are shown in Table 4.

TABLE 4

Mouse survival rate after administration of Welch *bacillus*

| Test compound | Number of surviving mice/number of treated mice | | | | |
|---|---|---|---|---|---|
| | 2 hours later | 6 hours later | 12 hours later | 24 hours later | 48 hours later |
| Example 1 | 4/4 | 4/4 | 4/4 | 3/4 | 3/4 |
| TDCM | 4/4 | 4/4 | 4/4 | 4/4 | 4/4 |
| Control | 4/4 | 3/4 | 0/4 | 0/4 | 0/4 |

As shown in Table 4, in Welch *bacillus* lethal models, three out of the four mice, to which the compound of Example 1 (the compound of the present invention) had been administered, escaped death.

Test Example 7

<Mouse Survival Test Involving Administration of Welch *bacillus* Toxin (Compound of Example 1)>

Emulsion solutions of the test compounds were prepared in the same manner as described above.

A Welch *bacillus* toxin was prepared as follows.

<Method for Preparing Welch *bacillus* Toxin>

A *Bacillus subtilis* α-toxin gene transformant was cultured in L-Broth at 37° C. for 14 hours, while stirring. Thereafter, the culture was centrifuged at 4° C. at 8,000 rpm for 20 minutes, and while stirring the culture supernatant under cooling on ice, a small amount of ammonium sulfate (Nacalai Tesque) was periodically added thereto. Thereafter, the reaction solution was adjusted to contain saturated ammonium sulfate having a final concentration of 70% (472 g/L), and it was then left overnight. Subsequently, the reaction solution was centrifuged at 4° C. at 9,500 rpm for 30 minutes, and the generated precipitate was dissolved in 0.02 M TB (pH 7.5). It was dialyzed against the same buffer as described above at 4° C. overnight. After completion of the dialysis, the reaction solution was centrifuged at 4° C. at 15,000 rpm for 30 minutes, and the obtained supernatant was used as a crude toxin (ammonium sulfate toxin) sample. This crude toxin sample was diluted with 1 M NaCl-TB (pH 7.5) so as to have a final concentration of 0.5 M NaCl. Thereafter, the crude toxin sample was applied to a copper chelate affinity column (1.5×9 cm) that had previously been equilibrated with 0.5 M NaCl-TB (pH 7.5), and then, 100 ml each of 0.5 M NaCl-TB (pH 7.5), 0.5 M NaCl-0.1 M PB (pH 6.5), 0.5 M NaCl-0.02 M acetate buffer (pH 4.5), and 0.5 M NaCl-0.1 M PB (pH 6.5) were successively applied to the column. Subsequently, toxin bound into the column was eluted with 100 ml of 15 mM L-histidine (Nacalai-Tesque)-0.5 M NaCl-0.1 M PB (pH 6.5), and the eluant was then filtrated with a syringe filter (DISMIC-ADVANTEC). The filtrate was subjected to centrifugal concentration using an ultrafiltration filter Amicon (trademark) Ultra-15-30K (Millipore), and the concentrate was then dialyzed against 0.02 M TB (pH 8.0) at 4° C. overnight. Thereafter, the resultant was centrifuged at 15,000 rpm for 30 minutes, and it was then applied to UNO (trademark) Q-1 R Column (BIO-RAD). Elution was carried out by linearly changing a sodium chloride concentration in 0.02 M TB (pH 8.0) from 0 M to 0.05 M at a flow rate of 1.0 ml/min. Elution (0.5 ml) fractions, in each of which a preparation line was observed in an Ouchterlony reaction with respect to an anti-α-toxin serum and each of which was found to contain an approximately 43-kDa single band corresponding to the α-toxin by SDS-PAGE, were collected, and the gathered fraction was then concentrated to approximately 1.0 ml. This concentrate was dialyzed against 0.02 M TB (pH 7.5) at 4° C. overnight, and it was then centrifuged at 4° C. at 15,000 rpm for 30 minutes. The supernatant (a recombinant α-toxin) was fractionated. The presence or absence of impurities contained in the obtained recombinant α-toxin was confirmed by SDS-PAGE, and it was then preserved at −80° C. before use.

<Survival Test Method Involving Administration of Welch *bacillus* Toxin>

Mice (ICR, 6-week-old) were divided into three groups, and the following test was then carried out.

An emulsion solution containing the test compound, an emulsion solution containing TDCM, or an emulsion solution alone, which was to be used as a control, was intraperitoneally administered in an amount of 100 μg/mouse to a group of four mice (100 μl/mouse, in the case of the emulsion solution alone). Three hours later, Welch *bacillus* toxin (200 ng/mouse) was intraperitoneally administered to the mice. Thereafter, the condition of the mice was observed.

The results are shown in Table 5.

TABLE 5

Mouse survival rate after administration of Welch *bacillus* toxin

| Test compound | Number of surviving mice/number of treated mice | | | | |
|---|---|---|---|---|---|
| | 2 hours later | 6 hours later | 12 hours later | 24 hours later | 48 hours later |
| Example 1 | 4/4 | 4/4 | 4/4 | 3/4 | 3/4 |
| TDCM | 4/4 | 4/4 | 4/4 | 2/4 | 2/4 |
| Control | 4/4 | 3/4 | 0/4 | 0/4 | 0/4 |

As shown in Table 5, in Welch *bacillus* toxin lethal models, three out of the four mice, to which the compound of Example 1 (the compound of the present invention) had been administered, escaped death.

Test Example 8

<Mouse Survival Test Involving Administration of *Pseudomonas aeruginosa* (Compound of Example 1)>

As a test compound, 1 mg of the compound synthesized by the method described in Production Example α-1 was weighed. An emulsion solution of the test compound was prepared in the same manner as described above.

*Pseudomonas aeruginosa* (Fhu-071115 strain) derived from patients was used, and it was prepared as follows.

<Method for Preparing *Pseudomonas aeruginosa*>

L-broth was withdrawn with a 40-ml measuring pipette and was then added to a 200-ml flask, and the flask was then sealed with a sponge plug. At the same time, 5 ml of L-broth was added to each of two other screw-top test tubes. The thus prepared flask and screw-top test tubes were subjected to an autoclave at 121° C. for 20 minutes. After the L-broth medium had been cooled to a room temperature, *Pseudomonas aeruginosa*, which had been stored in an ultra low temperature freezer, was added into 40 ml of the L-broth the medium in a clean bench. The obtained mixture was shaken in an incubator overnight. Thereafter, the resultant was centrifuged at 9000 rpm for 15 minutes, and the supernatant was then removed. Thereafter, 20 ml of sterilized normal saline solution was added to the precipitate, the mixture was then blended with the use of a Vortex mixer, and it was then centrifuged at 9000 rpm for 15 minutes, followed by the removal of the supernatant. This process was carried out three times. Thereafter, 4.5 ml of sterilized normal saline solution was added to the resultant, and the mixture was then blended with the use of a Vortex mixer. The obtained solution was used as a strain stock solution. Using a 1000-fold diluted strain solution, the number of cells was counted with OneCell Counter. Thereafter, the strain stock solution was diluted to a desired concentration, and the thus diluted solution was then used in the subsequent test.

<Survival Test Method Involving Administration of *Pseudomonas aeruginosa*>

Mice were divided into two groups, and the following two types of experiments were carried out.

(A) The aforementioned emulsion solution containing the test compound (100 μg/mouse) was intraperitoneally administered to a group of three mice (ICR, 5-week-old). Three hours later, *Pseudomonas aeruginosa* ($5.0 \times 10^7$ cells/mouse) was intraperitoneally administered to the mice. Thereafter, the condition of the mice was observed. (B) *Pseudomonas aeruginosa* ($2.0 \times 10^7$ cells/mouse) was intraperitoneally administered to a group of three mice (ICR, 5-week-old). Three hours later, the aforementioned emulsion solution containing the test compound (100 μg/mouse) was intraperitoneally administered to the mice. Thereafter, the condition of the mice was observed.

The results are shown in Table 6 and Table 7.

TABLE 6

(Group A) Mouse survival rate obtained in the case of pre-administration of test compound and administration of *Pseudomonas aeruginosa*

| Test compound | Number of surviving mice/number of treated mice | | | | |
|---|---|---|---|---|---|
| | 2 hours later | 4 hours later | 15 hours later | 24 hours later | 48 hours later |
| Example 1 | 3/3 | 3/3 | 2/3 | 2/3 | 2/3 |
| Control | 3/3 | 3/3 | 0/3 | 0/3 | 0/3 |

As shown in Table 6, in group A to which the test compound had previously been administered before administration of *Pseudomonas aeruginosa*, two out of the three mice escaped death caused by *Pseudomonas aeruginosa*. At the beginning of infection, there was no significant difference from the control group. However, from approximately 8 hours after the infection, the surviving mice were able to walk.

TABLE 7

(Group B) Mouse survival rate obtained in the case of administration of *Pseudomonas aeruginosa* and administration of test compound

| Test compound | Number of surviving mice/number of treated mice | | | | |
|---|---|---|---|---|---|
| | 2 hours later | 4 hours later | 15 hours later | 24 hours later | 48 hours later |
| Example 1 | 3/3 | 3/3 | 3/3 | 1/3 | 1/3 |
| Control | 3/3 | 3/3 | 0/3 | 0/3 | 0/3 |

As shown in Table 7, in group B to which the test compound was administered after administration of *Pseudomonas aeruginosa*, one out of the three mice escaped death caused by *Pseudomonas aeruginosa*.

Test Example 9

<Release of Cytokine from THP-1 Cells>

The amounts of various types of cytokines and chemokines from human monocytic leukemia cell-derived THP-1 cells, which had been treated with the test compound obtained in Example 9, were measured by the ELISA method. In addition, the same analysis was performed also on human lung cancer cell-derived A549 cells and human colon cancer cell-derived DLD-1 cells.

<Method for Culturing THP-1 Cells>

(1) Serum Lot Check

The cultured THP-1 cells were transferred into a 15-ml centrifuge tube in a clean bench. The cells were centrifuged at 1,000 rpm for 5 minutes at 20° C., and the supernatant was then removed. The precipitate was suspended in 1 ml of RPMI 1640 medium (containing FBS for use in 10% lot check), and the number of cells was then counted using a hemocytometer (Kayagaki Irika Kogyo Co., Ltd.) and a cover glass (Sansyo Co., Ltd.). Thereafter, the solution was diluted with a medium to a cell density of $2.5 \times 10^5$ cells/ml. 0.5 ml each of the cell suspension was dispensed into MULTI WELL PLATE 24 wells (SUMILON) used for suspension culture. The cell growth and the shape thereof were observed once a day. Two or three days later, the culture solution was 100-fold diluted with a medium, and then, the number of cells in 4 μl of the solution was counted using a counting slide. The cell growth conditions were compared. Cells, the growth and shape of which were good, were recovered from the well, and they were then washed with the same medium. Thereafter, the cell solution was diluted again to a cell density of $2.5 \times 10^5$ cells/ml. 1 ml of the cell suspension was dispensed into MULTI WELL PLATE 6 wells (SUMILON) used for suspension culture, and it was then incubated at 37° C. in a 5% $CO_2$ atmosphere. The medium was exchanged with a new one every 24 hours. The plate itself was centrifuged (TOMY) at 1,800 rpm for 5 minutes, the medium was then slowly removed, and 1 ml of new medium was then added. Such a medium exchange operation was carried out two times. On the third day or later, after the medium had been exchanged with a new one, the cells were 100-fold diluted, and the number of cells was then counted using a counting slide. The degree of cell growth was measured. Thereafter, this operation was repeatedly carried out for several days, and media, the growth and shape of which were good, were selected.

(2) Inactivation and Dispending of Serum 500 ml of fetal bovine serum (FBS) (Biowest) that had been thawed at 4° C. was incubated for 30 minutes, while stirring it sometimes at 56° C., so as to inactivate it. Thereafter, 30 ml each of the serum was dispensed in a 50-ml centrifuge tube in a clean bench without filtrating it, and it was then preserved at −80° C. The preserved serum was thawed at 4° C. when used.

(3) RPMI 1640 Medium (10% inactivated FBS+1% *penicillin streptomycin*)

60 ml of the inactivated FBS and 5.6 ml of *penicillin streptomycin* (GIBCO) that had been filtrated with Acrodisc 25 mm Syringe Filter (Pall Corporation) were added to 500 ml of RPMI 1640 liquid medium (Wako) in a clean bench, and they were then mixed so that they became homogeneous. The prepared medium was directly used without filtrating it. The medium was preserved at 4° C., and it was returned to a room temperature when used.

(4) Subculture of Cells

THP-1 cells were cultured in a 75-cm$^2$ suspension culture flask (SUMILON) (had grown at 90% or more), and the shape and growth of the cells were observed. When the cell shape was good and the cell growth rate was high, the cell suspension was transferred into another flask, or a new medium was added to the used flask in an amount of two times the amount of the cell suspension, so as to carry out subculture. When the cell growth rate was low, the condition was continuously observed, or a new medium was added to the cell suspension in an equal amount thereof, so as to carry out subculture.

(5) Preservation of Cells 10 to 15 ml of the cells that had been cultured in the 75-cm$^2$ suspension culture flask (had grown at 90% or more) were transferred into a centrifuge tube, and it was then centrifuged at 1,000 rpm for 5 minutes. Then, the supernatant was removed. Thereafter, 1 ml of cell cryopreservation solution, Cell banker (Nippon Zenyaku Kogyo Co., Ltd.) was added to the precipitate, followed by suspension. The obtained suspension was dispensed into a serum tube, and it was then preserved at −80° C.

(6) Re-Culture of Preserved Cells

The cells that had been frozen at −80° C. were quickly thawed in a 37° C. water bath. The cell preservation solution was immediately added to a 15-ml centrifuge tube, to which 9 to 10 ml of RPMI 1640 medium had previously been added, and the obtained mixture was then blended by shaking it upside down. The mixture was centrifuged at 1,000 rpm for 5 minutes, and the supernatant was then removed. The precipitate was resuspended in 10 ml of new medium, and the cell suspension was then transferred into a 75-cm$^2$ suspension culture flask. Thereafter, a new medium was added to the cell suspension to a total amount of 20 to 30 ml, and the obtained mixture was then cultured at 37° C. in a 5% CO$_2$ atmosphere.

<Preparation of ELISA Kit Reagents>

Preparation of Washing Solution

A washing solution was 25-fold diluted with sterile distilled water (S.D.W.), and it was then used at a room temperature.

Preparation of Standard Substrate Solution

600 μL of diluent solution for standard substrate solution had previously been added to two microtubes. A standard substrate was dissolved in 1 mL of diluent solution for standard substrate solution (2450 pg/mL), 100 μL of the obtained solution was then transferred into a microtube, and it was then dissolved therein (350 pg/mL). 100 μL of the solution was further transferred into another microtube, it was then dissolved therein (50 pg/mL), followed by dilution. The diluent solution for standard substrate solution was used as a control (0 pg/mL).

Preparation of Coloring Solution

Color reagent A and color reagent B were mixed in equal amounts. A coloring solution in an amount of 100 μl/well×the number of wells to be measured, was added to the mixture. This solution was prepared within 15 minutes before use.

<Measurement of Sample>

An ELISA kit reagent to be used was returned to a room temperature. A standard substrate solution having a different concentration and an assay buffer (50 μL) were added to each well, and 50 μL of sample was further added thereto. The plate was gently tapped for 1 minute, and a cover was applied onto the plate, followed by incubation at a room temperature for 2 hours. Thereafter, the resultant was washed with a washing solution five times (wherein an aspirator was usable), and 100 μL of the prepared conjugate solution was then added to each well. A cover was applied onto the plate, and it was then incubated at a room temperature for 2 hours. Thereafter, the resultant was washed with a washing solution five times, and under light-shielded conditions, 100 μL of mixed solution consisting of color reagent solutions A and B was added to each well. The plate was incubated at a room temperature in a dark place for 30 minutes. Finally, 100 μL of reaction termination solution was added to each well, and within 30 minutes after the addition, absorbance was measured using a microplate reader (Molecular Devices spectra MAX 340PC) (450 nm-550 nm). From a straight line graph of standard substrate solution, the amount of cytokine released from each sample was calculated.

<Experimental Method>

The cultured THP-1 cells were transferred into a 50-ml centrifuge tube in a clean bench. The cells were centrifuged at 1,000 rpm for 5 minutes at 20° C., and the supernatant was then removed. The precipitate was suspended in 1 ml of new serum-free RPMI 1640 medium (Wako), and 10 μl of the cell suspension was then added to a sterile Eppendorf tube, to which 990 μl of serum-free RPMI 1640 medium had previously been added, so that the solution was 100-fold diluted. The number of cells in 4 μl of the 100-fold diluted solution was counted with a blood cell counter, and the cell suspension was then diluted with serum-free RPMI 1640 medium to a cell density of 1×10$^7$ cells/ml. 100 μL of RPMI medium was added to an Eppendorf tube, and a 40 mM test compound (Example 9)/DMSO solution was added thereto to a concentration of 200 μM. Thereafter, ultrasonic wave was applied to the mixture for 5 seconds. 100 μl of THP-1 cells were added thereto (final concentration of the test compound: 100 μM). The obtained mixture was incubated at 37° C. for 2 hours, and it was then centrifuged at 5000 rpm for 10 minutes. The supernatant was transferred into another Eppendorf tube, and the sample was then measured using the ELISA kit.

It is to be noted that a test compound, 6,6'-bis-O-(2-tetradecylhexanoyl)-α,α'-trehalose (hereinafter referred to as a "control compound A"), and TDCM were used as positive controls, and that these compounds were also measured in the same manner as described above. In addition, a negative control was prepared by adding no test compounds (vehicle).

<Experimental Results>

Figure 9:
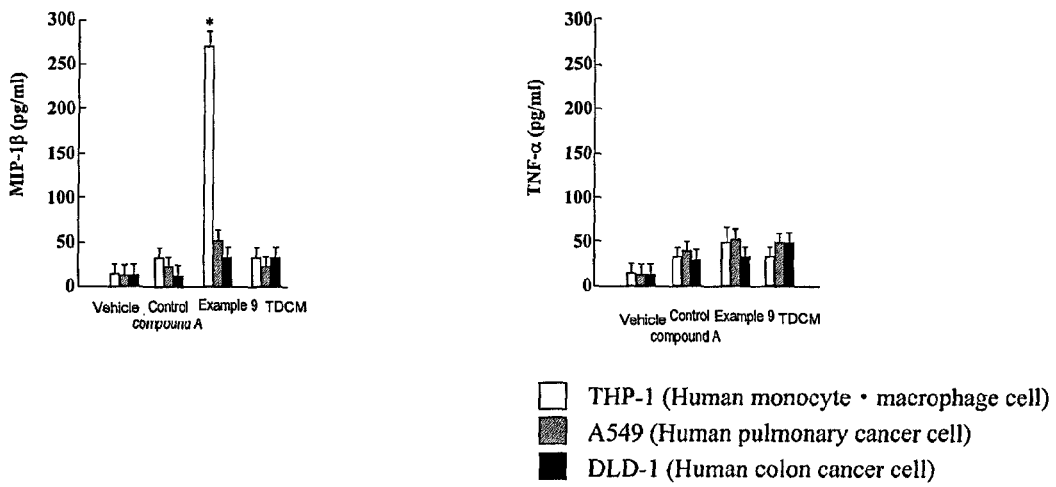
FIG. 9 shows the amount of MIP-1β and the amount of TNF-α released from human-derived cells in a case in which TDCM, a vehicle or the test compound of the present invention was allowed to act on the human-derived cells. The value was indicated with a mean±S.D. (n=5). The symbol * indicates the case of P<0.01, compared with the control.

It became clear that MIP-1β was released from THP-1 cells that had been treated with the compound of Example 9 at a level that was approximately 8 to 10 times higher than that of THP-1 cells that had been treated with the positive control. Moreover, the release level of TNF-α from THP-1 cells treated with the compound of Example 9 was almost equivalent to the release level of TNF-α from THP-1 cells treated with the negative control. The results are shown in FIG. 9. The release level of MIP-1β from THP-1 cells treated with the compound of Example 1 was higher than the release level of MIP-1β from THP-1 cells treated with the positive control. On the other hand, the release level of TNF-α from THP-1 cells treated with the compound of Example 1 was almost equivalent to the release level of TNF-α from THP-1 cells treated with the negative control (data not shown).

Text Example 10

<Analysis of Cytotoxicity to THP-1 Cells and Mutagenicity Test>
<Analysis of Cytotoxicity to THP-1 Cells Using Trypan Blue>
Preparation of Reagent
Preparation of 0.3% Trypan Blue/PBS (−)
  0.3 g of trypan blue (Nacalai) was dissolved in 100 ml of PBS (−).
Preparation of THP-1 Cells
  The cultured THP-1 cells were transferred into a 50-ml centrifuge tube in a clean bench. The cells were then centrifuged at 1,000 rpm for 5 minutes at 20° C., and the supernatant was then removed. The precipitate was suspended in 1 ml of new serum-free RPMI 1640 medium (Wako). 10 μl of this cell suspension was added to a sterile Eppendorf tube, to which 990 μl of serum-free RPMI 1640 medium had previously been added, so that the solution was 100-fold diluted. The number of cells in 10 μl of the 100-fold diluted solution was counted with a blood cell counter, and the cell suspension was diluted with serum-free RPMI 1640 medium to a cell density of $1 \times 10^7$ cells/ml.
<Experimental Method>
  A test compound (Example 9)/DMSO solution, or DMSO was added to 100 μl of RPMI medium to a concentration of 200 μM. Thereafter, ultrasonic wave was applied to the mixture for 5 seconds. It is to be noted that a test compound, 6-O-(2-decyldecanoyl)-α-glucose (hereinafter referred to as a "control compound B"), and TDCM were used to prepare positive controls in the same manner as described above. In addition, a negative control was prepared by adding no test compounds (vehicle). 100 μl of THP-1 cells, which had been adjusted to a cell density of $1 \times 10^7$ cells/ml, were added thereto, and the obtained mixture was then incubated at 37° C. for 2 hours or 24 hours. Subsequently, 20 μl of 0.3% trypan blue/PBS (−) was added to the reaction solution so as to suspend the reaction solution therein, and thereafter, the survival rate of the cells was immediately analyzed using a cell number measuring apparatus (CYRORECON).
<Mutagenicity Test (Ames Test)>
Preparation of Reagent
Preparation of 0.1 M Sodium Phosphate Buffer
  5.68 g of $Na_2HPO_4$ was dissolved in 200 mL of distilled water. Thereafter, $NaH_2HPO_4.2H_2O$ dissolved in 100 ml of distilled water was gradually added to the obtained solution, so as to adjust the solution to pH 7.4. The solution was then subjected to high-pressure steam sterilization.
Preparation of Minimal Glucose Agar Medium
(1) VB medium: 0.4 g of $MgSO_4.7H_2O$, 4 g of citric acid $H_2O$, 20 g of $K_2HPO_4$, and 7 g of $NaNH_4HPO_4.4H_2O$ were dissolved in 200 mL of distilled water, and the obtained solution was then subjected to high-pressure steam sterilization.
(2) 40 g of glucose was dissolved in 200 mL of distilled water, and the obtained solution was then subjected to high-pressure steam sterilization.
(3) 30 g of powdered agar was suspended in 1600 mL of distilled water, and the obtained suspension was then subjected to high-pressure steam sterilization.
  After the reagent of (3) had been cooled to approximately 60° C., the reagent of (1) was mixed with the reagent of (2), and the approximately 30 mL each of the obtained mixture was dispersed on a Petri dish.

Figure 10:
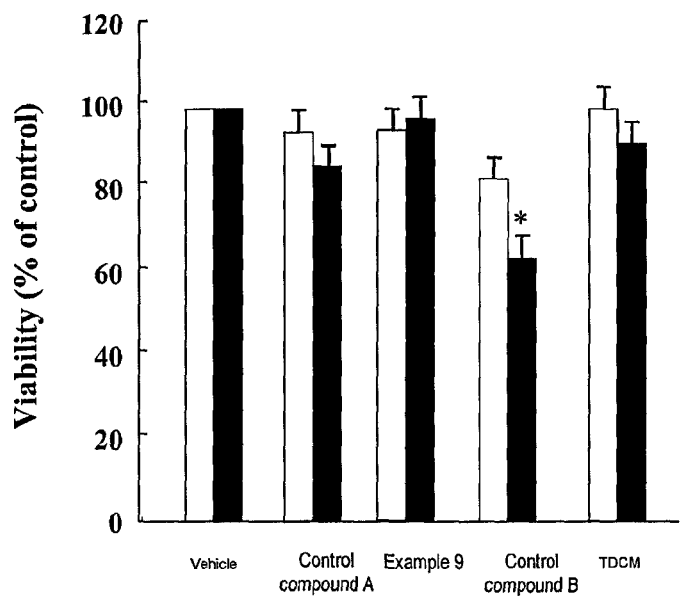
FIG. 10 shows the cytotoxicity of TDCM, a vehicle or the test compound of the present invention in human-derived THP-1 cells. The white bar shows the results obtained by treating the cells with the test compound for 2 hours, whereas the black bar shows the results obtained by treating the cells with the test compound for 24 hours. The value was indicated with a mean±S.D. (n=5). The symbol * indicates the case of P<0.01, compared with the control.
Figure 11:
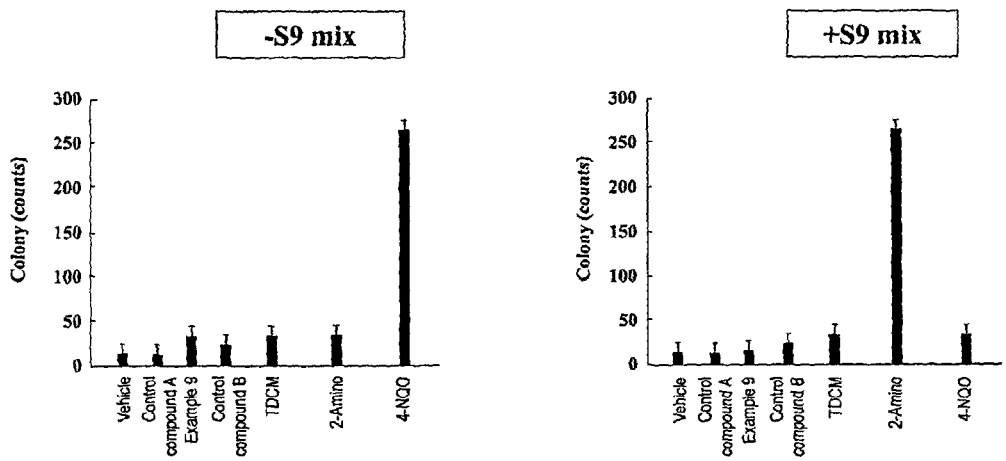
FIG. 11 shows the measurement results of the mutagenicity of TDCM, a vehicle or the test compound of the present invention according to an Ames test.

Preparation of Upper-Layer Agar Medium
  1.2 g of powdered agar and 1 g of NaCl were suspended in 200 mL of water, and the obtained suspension was then subjected to high-pressure steam sterilization. Thereafter, the resultant was transferred into a 50-ml tube. Before use, 20 mL of 0.5 mM histidine/biotin solution was mixed with it, and the obtained mixture was kept warm at 47° C.
Preparation of Oxoid Nutrient Broth Medium Used for Culture of *Salmonella typhii*
  2.5 g of Oxoid Nutrient Broth medium (Difco) was dissolved in 100 ml of distilled water, and 5 ml of the obtained solution was then placed in a screw-top test tube, followed by sterilization. Thereafter, approximately 10 μL of cell solution of TA98 (*Salmonella typhmurium* TA98) was inoculated into the test tube, and the obtained mixture was then subjected to a shaking culture at 37° C. overnight, so as to prepare a cell suspension.
Preparation of S9 Mix
  9 ml of Co factor A mix (ORIENTAL YEAST) was added to 1 ml of S9.
Preparation of Standard Mutagenic Substance
Preparation of 4-NQO/DMSO
  0.3 mg of 4-Nitroquinoline N-oxide (4-NQO) (Tokyo Chemical Industry Co., Ltd.) was dissolved in 10 ml of DMSO.
Preparation of 2-aminoanthracene/DMSO
  0.5 mg of 2-aminoanthracene (ALDRICH) was dissolved in 30 ml of DMSO.
<Experimental Method>
  10 μL each of the standard mutagenic substance, the test compound of Example 9, the control compound B, and TDCM were each placed in an Eppendorf tube. Two Eppendorf tubes were prepared for each of the aforementioned compounds. 0.5 mL of S9 mix or 100 mM phosphate buffer was added to each tube, and 100 μL of the cell suspension was also added thereto, followed by preincubation (shaking at 37° C. for 20 minutes). Thereafter, 2 mL of soft agar containing histidine-biotin (which was incubated at 47° C.) was added to the reaction solution, followed by moderate suspension. The obtained solution was dispersed on a minimal glucose agar medium, and it was then incubated (37° C., 2 days). Thereafter, the number of His colonies was counted.
<Experimental Results>
  In order to examine cytotoxicity to THP-1 cells, the survival rates of THP-1 cells, which had been treated with the test compound obtained in Example 9 for 2 hours and for 24 hours, were analyzed by trypan blue staining. As a result, cytotoxicity was observed in the cells, which had been treated with the control compound B. In contrast, such cytotoxicity was not observed in the cells, which had been treated with the compound obtained in Example 9. The results are shown in FIG. 10. Moreover, in the case of the compound obtained in Example 1 as well, significant results could be obtained (data not shown).
  Furthermore, an Ames test was carried out on the test compound obtained in Example 9 in the presence or absence of S9 mix. In both cases, the test compound did not exhibit mutagenicity. Further, the mutagenicity of the standard substance (2-aminoanthracene, 4NQO) was positive under the present analytical conditions (FIG. 11). Still further, in the case of the compound obtained in Example 1 as well, significant results could be obtained (data not shown).

Test Example 11

<Cell Infiltration into Mouse Abdominal Cavity>
<Preparation of PBS (−) Solution>
  4 g of NaCl, 1.45 g of $Na_2HPO_4.12H_2O$, 0.1 g of $KH_2PO_4$, and 0.1 g of KCl were dissolved in 500 ml of distilled water, and the obtained solution was then subjected to high-pressure steam sterilization at 121° C. for 20 minutes.

<Preparation of 0.05% EDTA/PBS (−) Solution>

50 mg of EDTA (Nacalai Tesque code. 151-30) was dissolved in 100 ml of PBS (−), and the obtained solution was then subjected to mechanical sterilization using a 0.2-μm filter.

<Preparation of 1 mg/mL Emulsion Solution>

0.9 g of NaCl, 1.1 ml of Polyoxyethylene Sorbitan Monooleate (Tween 80), and 5.6 g of D (−)-Mannitol were dissolved in 100 ml of distilled water, and the obtained solution was then subjected to mechanical sterilization using a 0.2-μm filter. 1 mg of the test compound obtained in Example 9 was placed at the bottom of a homogenizer (WEATON U.S.A., 10 mL, AS ONE Corp.). A droplet of mineral oil was added thereto, and the obtained mixture was then homogenized while applying ultrasonic wave thereto for 2 minutes. Thereafter 1 mL of 1.1% Tween-5.6% Mannitol Saline was added to the reaction solution, and the obtained mixture was then homogenized until it became clouded and homogeneous. The total amount of the solution of the test compound was transferred into an Eppendorf test tube, and it was then treated at 62° C. for 30 minutes for pasteurization. The control compound A and TDCM were used as test compounds (positive controls). On the other hand, no test compounds were added to the emulsion solution to prepare a negative control (vehicle).

<Recovery of Intraperitoneal Infiltrating Cells>

A solution containing the 1 mg/mL test compound (Example 9) was intraperitoneally administered to mice (ICR mice (SPF) (4-week-old, male, body weight: 20-22 g) to a concentration of 100 μg/mouse.

The mice, to which the test compound had been intraperitoneally administered, were sacrificed with the use of diethyl ether, 2 hours or 24 hours after the administration. The epidermis in the center of abdomen was partially cut with scissors, and thereafter, the abdomen was picked up and the epidermis thereof was then peeled off. The peritoneum was lightly picked up with tweezers, and 5 mL of 0.05% EDTA in PBS (−) was injected in the total amount into the abdominal cavity, using a 10-mL syringe equipped with a 26 G needle, while paying attention not to inject the needle into organs. Thereafter, the abdomen was massaged about 40 to 50 times by picking up the side of the abdomen. Thereafter, liquid in the abdominal cavity was slowly collected into a small size centrifuge tube. This operation was carried out again. The collected cells were centrifuged at 1,000 rpm for 10 minutes. The supernatant was removed, and the precipitate was then suspended in an RPMI 1640 medium. The centrifuge tube was filled with an RPMI 1640 medium, and it was then centrifuged at 1,000 rpm for 10 minutes again. The supernatant was discarded, and the precipitate was then suspended in an RPMI 1640 medium. Thereafter, the number of cells was counted using a cell counter. The suspension was then diluted with an RPMI-1640 medium to any given concentration.

<Giemsa Staining of Cells>

<Preparation of ¹⁄₁₅ M Sodium Phosphate Buffer (pH 6.4)>

6.0g of $NaH_2PO_4$ and 7.06 g of $Na_2HPO_4$ were each dissolved in 250 ml of distilled water, and a sodium dihydrogen phosphate solution was then added to a disodium hydrogen phosphate solution, while measuring the pH thereof, so as to adjust the pH value to pH 6.4. Thereafter, the obtained solution was sterilized in an autoclave at 121° C. for 20 minutes.

A 1 mg/mL test compound solution was intraperitoneally administered to mice to a concentration of 100 μg/mouse. Twenty-four hours later, cells infiltrating into the abdominal cavity were recovered using EDTA/PBS (−). Thereafter, the cells were centrifuged at 1000 rpm for 8 minutes, and the supernatant was then removed. The cells were suspended in 100 μL of phosphate buffer, and the obtained suspension was placed on a slide glass for staining. After confirming the evaporation of water content, 10 to 15 droplets of May-Grunwald solution were added dropwise thereto on a staining vat, and it was then left for 2 to 3 minutes. Without throwing away the May-Grunwald solution, 10 to 15 droplets of phosphate buffer were added dropwise thereto, and it was then left for 2 to 3 minutes. An adequate amount of Giemsa staining solution was added to the reaction solution, and the obtained mixture was then left for 30 minutes. Thereafter, the slide glass was turned over, and water was then supplied thereto. The slide glass was dried, and it was then observed under a microscope.

<Analysis of CD8-Positive Cells in Mouse Abdominal Cavity by Flow Cytometry>

Preparation of Reagents

Preparation of PBS (−) Solution

A PBS (−) solution was prepared by the same method as that applied in Test Example 11.

Preparation of 1 mg/mL Test Compound (Emulsion Solution)

An emulsion solution containing a 1 mg/mL test compound was prepared by the same method as that applied in Test Example 11.

Preparation of 0.05% EDTA/PBS (−) Solution 50 mg of EDTA 2Na was dissolved in 100 ml of PBS (−), and the obtained solution was then sterilized in an autoclave at 121° C. for 20 minutes.

Preparation of 0.5% BSA-0.05% EDTA/PBS (−) Solution 50 mg of EDTA 2Na was dissolved in 100 ml of PBS (−), and the obtained solution was then sterilized in an autoclave at 121° C. for 20 minutes. Thereafter, 0.5% BSA was dissolved in the reaction solution when used.

<Experimental Method>

A 1 mg/mL test compound emulsion solution was intraperitoneally administered to mice (100 μg/mouse). Twenty-four hours later, cells infiltrating in the abdominal cavity were recovered using 0.05% EDTA/PBS (−). Thereafter, the collected peritoneal cells were centrifuged at 300 g for 10 minutes, and the supernatant was then removed. The prepared peritoneal cells were suspended in 1 ml of 0.05% EDTA (dissolved in 0.5% BSA/PBS). The cell suspension was filtrated with a mesh used for flow cytometry, and the number of cells was then counted in a 100-fold diluted cell suspension. Cells in each sample were adjusted to a cell density of $10^7$ cells/sample, and they were then centrifuged at 300 g for 10 minutes, followed by the removal of the supernatant. The precipitate was suspended in 100 μl of 0.05% EDTA (dissolved in 0.5% BSA/PBS), and 10 μl each of CD11b, CD4 and CD8 antibodies (FITC anti-mouse CD11b/Mac-1 (BECKMAN), FITC anti-mouse CD4 (BECKMAN COULTER) and PE anti-mouse CD8a (BD Pharmingen), respectively) were added. The obtained mixture was incubated at 2° C. to 8° C. in a dark place for 10 minutes, and the cells were then suspended in 1 to 2 ml of 0.05% EDTA (dissolved in 0.5% BSA/PBS). The cell suspension was centrifuged at 300 g for 10 minutes, and the supernatant was then removed. The precipitate was suspended in 1 ml of 0.05% EDTA (dissolved in 0.5% BSA/PBS), and the solution was then analyzed by flow cytometry.

<Experimental Results>

The cells were suspended in 1 mL of PBS (−). 100 μL of Hemolynac (hemolytic hemoglobin reagent) was added to the cell suspension so as to destroy erythrocytes. Thereafter, the number of cells was counted using a cell measurement apparatus (CYTORECON, GE Healthcare).

Moreover, the prepared cells were inoculated on a 24-well Collagen Well (Greiner), and were incubated for 2 hours. Thereafter, the supernatant was aspirated, and then, the cells were repeatedly washed with an RPMI medium two times. 300 of RPMI medium was added to the resultant cells, and the cells were then observed under an inverted microscope.

Figure 12:
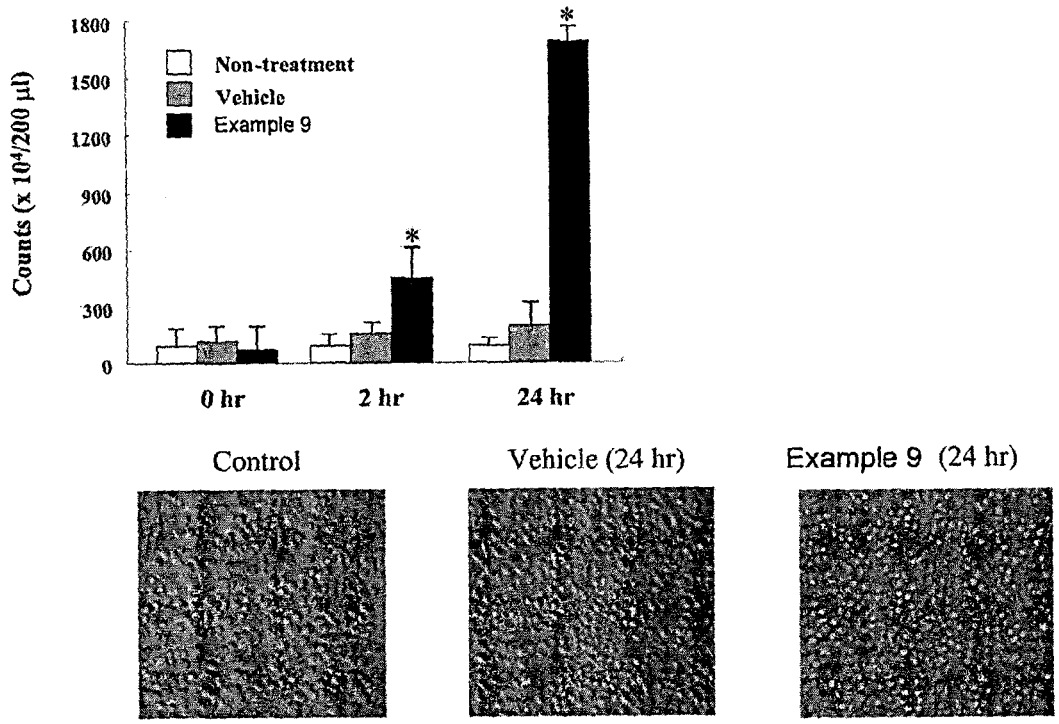
FIG. 12 shows the number of cells and microscopic images obtained in a case in which TDCM, a vehicle or the test compound of the present invention was allowed to act on mouse intraperitoneal infiltrating cells. The value was indicated with a mean±S.D. (n=5). The symbol * indicates the case of P<0.01, compared with the control.

As a result, an increase in infiltrating cells was observed time-dependently in the abdominal cavity of mice, to which the test compound obtained in Example 9 had been administered. Twenty-four hours later, the number of infiltrating cells became 15 to 20 times higher than that had been treated with a vehicle (FIG. 12).

Figure 13:
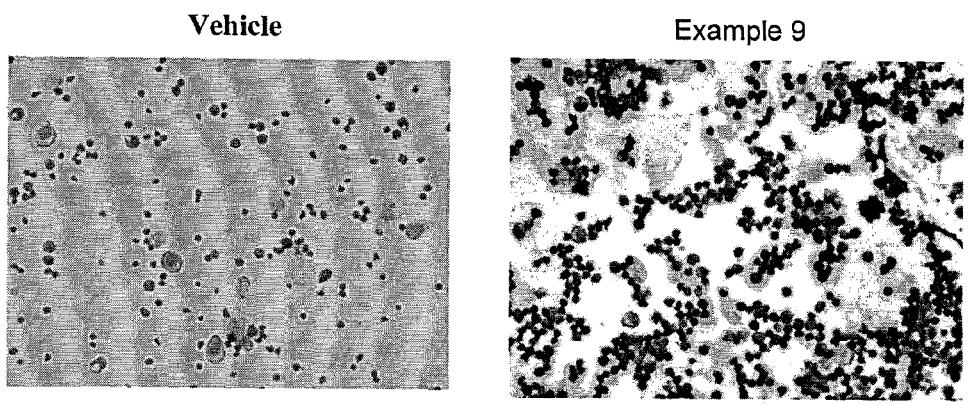
FIG. 13 shows the results of Giemsa staining, which were obtained in a case in which TDCM, a vehicle or the test compound of the present invention was allowed to act on mouse intraperitoneal infiltrating cells.
Figure 14:
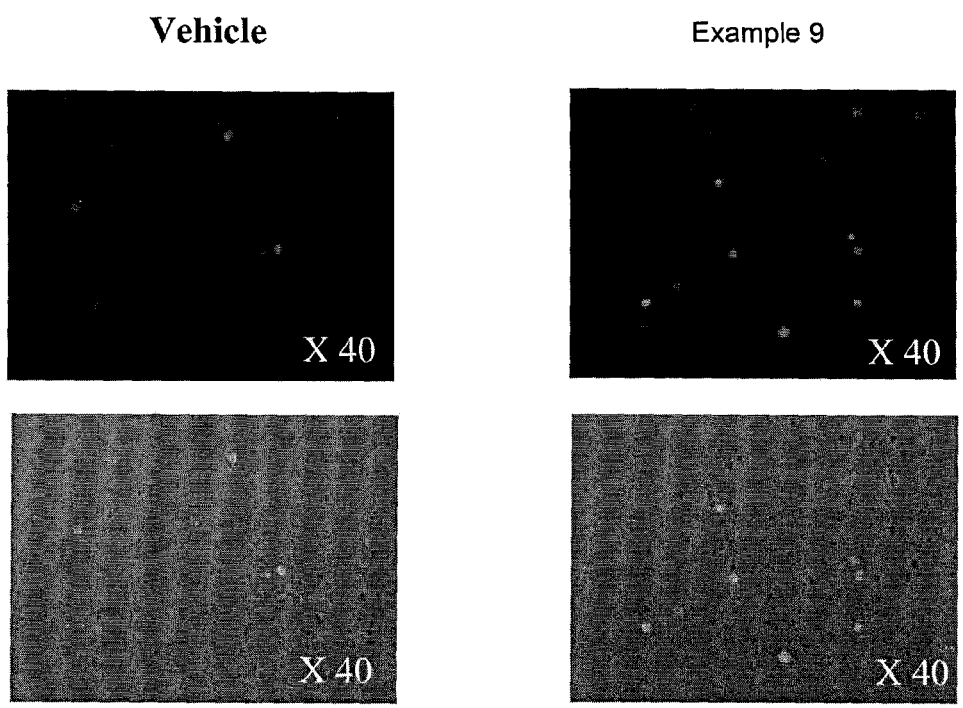
FIG. 14 shows the images of CD-8-positive cells in mouse intraperitoneal infiltrating cells, on which TDCM, a vehicle or the test compound of the present invention was allowed to act, which were observed under a fluorescent microscope.
Figure 15:
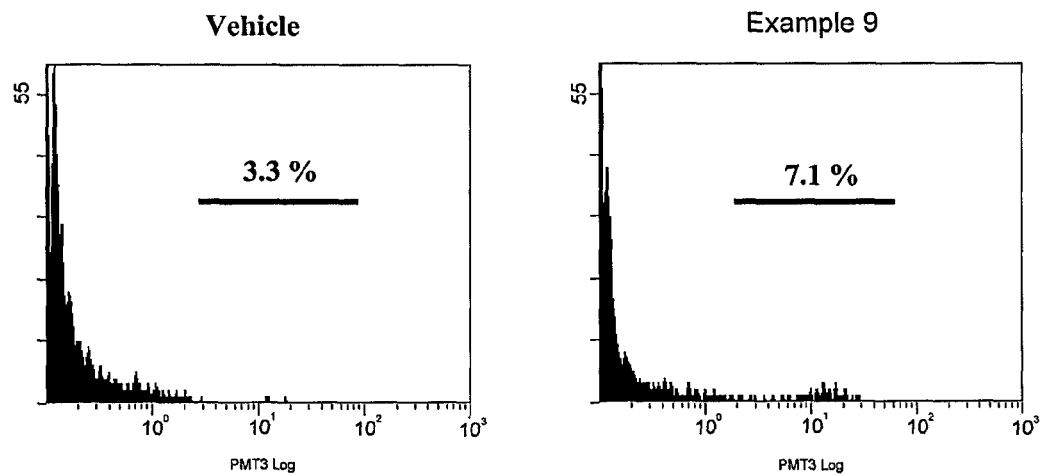
FIG. 15 shows the measurement results of CD-8-positive cells in mouse intraperitoneal infiltrating cells, on which TDCM, a vehicle or the test compound of the present invention was allowed to act, which were obtained by flow cytometry.

Moreover, in order to analyze infiltrating cells, the shape of the cells was observed by Giemsa staining, and the cells were treated with various antibodies against a monocyte and macrophage antigen (CDllb), a lymphocyte antigen (CD4) and an NK cell antigen (CD8). The cells were then analyzed by flow cytometry. As a result, twenty-four hours after administration of the test compound obtained in Example 9, the total number of CD11b-positive cells, CD4-positive cells and CD8-positive cells was 15 to 20 times larger than the number of cells that had been treated with a vehicle. However, the abundance ratio of the CD11b-positive cells and CD4-positive cells that had been treated with the test compound of Example 9 was hardly changed from that in the case of being treated with a vehicle. On the other hand, the abundance ratio of the CD8-positive cells became approximately 2 to 3 times higher than that in the case of being treated with a vehicle (FIGS. 13 to 15).

As described above, it was found that phagocyte system cells were accumulated in mouse abdominal cavity by the action of the test compound of Example 9, and that, in particular, the ratio of NK cells was high.

Test Example 12

<Influence of Test Compound on Welch *bacillus*-Infected Mice or *Pseudomonas aeruginosa*-Infected Mice (Compound of Example 9)>
<Method for Preparing Welch *bacillus*>
Preparation of COOKED MEAT Medium (Hereinafter Abbreviated as a "CM Medium" at Times)

A CM medium (125 mg/ml in D.W.) was added to a screw-top test tube, and it was then boiled for 15 minutes, so as to remove air from the CM medium. High-pressure steam sterilization was performed in an autoclave (121° C., 20 minutes), and the resultant was then cooled to a room temperature.
Preparation of Brain Heart Infusion (Hereinafter Abbreviated as "BHI") Medium 37 mg of BHI medium was dissolved in 100 ml of distilled water. Thereafter, 4.5 mL of the obtained solution was added to a screw-top test tube, and 40 mL of the obtained solution was added to an Erlenmeyer flask. They were sealed with sponge plugs, and high-pressure steam sterilization was then carried out thereon in an autoclave (121° C., 20 minutes). Thereafter, the resultants were cooled to a room temperature.
Preservation of Cells

*C. perfringens* Type-A NCTC8237 (PLC+) was added to the prepared CM medium, and it was then cultured at 37° C. for 2 days. The obtained culture was preserved as a preserved cell solution at a room temperature.
Culture of Cells and Preparation of Cell Solution 0.2 mL of cell solution was collected from each preserved cell solution, and it was then added to 4.5 mL of BHI medium used for pre-culture, followed by a culture at 37° C. overnight. The total amount of this culture solution was added to 40 mL of BHI medium, and nitrogen substitution was then carried out (10 minutes). Thereafter, it was cultured again at 37° C. for 5 hours. Thereafter, the culture solution was added to a 50-mL tube, and it was then centrifuged (4° C., 9000 rpm, 15 minutes). The supernatant was removed, and a normal saline solution was added to the precipitate to fully wash it. Thereafter, the resultant was centrifuged again (4° C., 9000 rpm, 15 minutes), and cells were then collected. This washing operation was repeatedly carried out two times. 4.5 mL of BHI medium was added to the precipitate so as to suspend it. The obtained suspension was used as a stock solution. This stock solution was 1000-fold diluted, and the diluted solution was then subjected to high-pressure steam sterilization in an autoclave (121° C., 20 minutes). Thereafter, the number of cells was counted using OneCell Counter. A cell solution having a cell density of $1 \times 10^8$ cells/mL was produced, and was used in the subsequent experiment.
<Method for Preparing *Pseudomonas aeruginosa*>
Preparation of Luria Bertani Broth Medium (L-Broth)

10.0 g of Bacto™ Tryptone (Difco), 5.0 g of Bacto™ Yeast Extract (Difco), and 5.0 g of sodium chloride (NaCl) (Nacalai Tesque) were dissolved in distilled water, and 1.0 mL of 1 M $MgSO_4$ was then added to the obtained solution. Then, 1 N NaOH was added to the solution to adjust it to pH 7.5. Distilled water was added to the solution to a total amount of 1,000 mL. Thereafter, the obtained solution was subjected to high-pressure steam sterilization in an autoclave at 121° C. for 20 minutes, and the reaction solution was then cooled to a room temperature.
Preservation of Cells 0.2 mL of *Pseudomonas aeruginosa* (*P. Aeruginosa*) was added to 10 mL of L-Broth, and the mixture was then subjected to a shaking culture at 37° C. overnight. Thereafter, 1 mL of sterile glycerin was added to the obtained culture solution, and the obtained mixture was then blended with the use of a Vortex mixer. 300 μL each of the cell solution was dispensed into a sterile Eppendorf tube, and it was then preserved at −80° C.

0.2 mL each of the preserved cell solution was added to 40 mL of L-Broth medium, and the mixture was then subjected to a shaking culture at 37° C. overnight. Thereafter, the culture was transferred into a 50-mL tube, and it was then centrifuged (4° C., 9000 rpm, 15 minutes). The supernatant was removed, and a normal saline solution was added to the precipitate to fully wash it. Thereafter, the resultant was centrifuged again (4° C., 9000 rpm, 15 minutes), and cells were then collected. This washing operation was repeatedly carried out two times. 4.5 mL of normal saline solution was added to the precipitate so as to suspend it. The obtained suspension was used as a stock solution. This stock solution was 10000-fold diluted, and the thus diluted cell solution was then subjected to high-pressure steam sterilization in an autoclave (121° C., 20 minutes). Thereafter, the number of cells was counted using OneCell Counter. A cell solution having a cell density of $1 \times 10^8$ cells/mL was produced, and was used in the subsequent experiment.
<Experimental Method: Pre-Administration of Test Compound>

An emulsion solution containing 100 μg/mouse test compound (Example 9) was intraperitoneally administered to mice. Twenty-four hours later, $3.0 \times 10^{10}$ CFU/mL *Pseudomonas aeruginosa* or $5.0 \times 10^7$ CFU/mL Welch *bacillus* was intraperitoneally administered to the mice. Thereafter, the mice were observed every 2 hours.

<Experimental Method: Post-Administration of Test Compound>

$3.0 \times 10^{10}$ CFU/mL *Pseudomonas aeruginosa* was intraperitoneally administered to mice. Three hours later, an emulsion solution containing 100 μg/mouse test compound (Example 9) was intraperitoneally administered to the mice. Thereafter, the mice were observed every 2 hours.

<Experimental Results>

Figure 16:
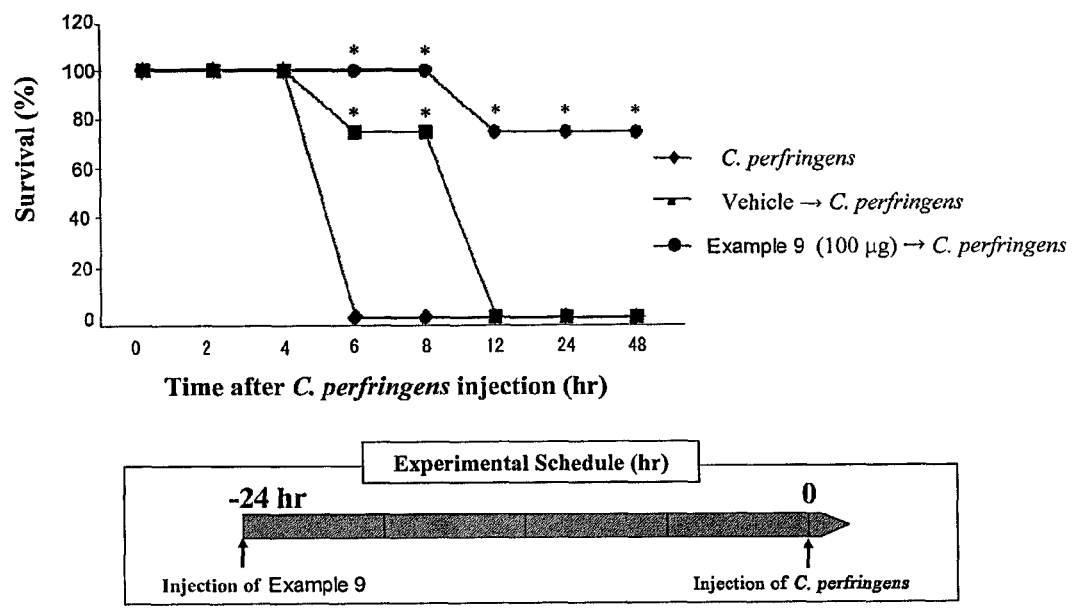
FIG. 16 shows the influence of TDCM, a vehicle or the test compound of the present invention on the number of surviving mice, to which each of the above described compounds was administered and then Welch *bacillus* was then administered. The symbol * indicates the case of P<0.01, compared with the control. The test was carried out 8 times, and standard results were shown.
Figure 17:
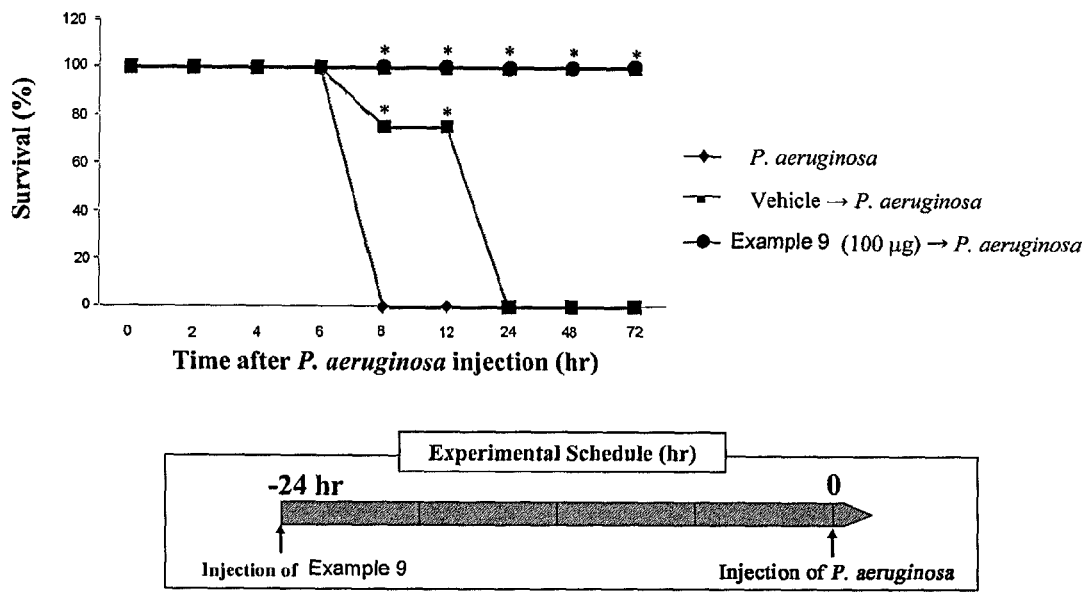
FIG. 17 shows the influence of TDCM, a vehicle or the test compound of the present invention on the number of surviving mice, to which each of the above described compounds was administered and then *Pseudomonas aeruginosa* was then administered. The symbol * indicates the case of P<0.01, compared with the control. The test was carried out 8 times, and standard results were shown.
Figure 18:
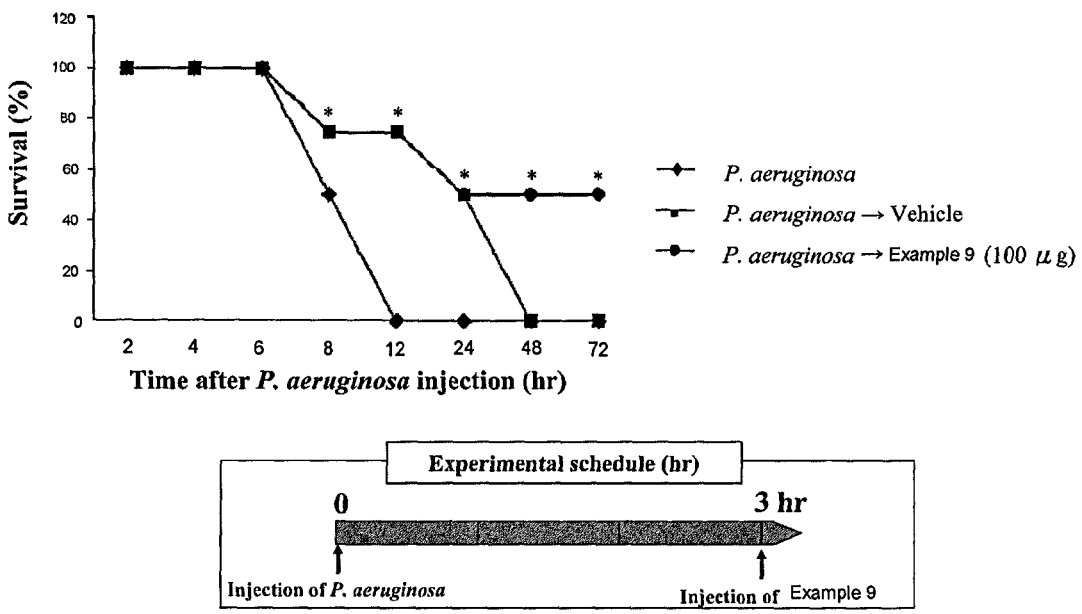
FIG. 18 shows the influence of TDCM, a vehicle or the test compound of the present invention on the number of surviving mice, to which each of the above described compounds was administered after completion of the administration of *Pseudomonas aeruginosa*. The symbol * indicates the case of P<0.01, compared with the control. The test was carried out 8 times, and standard results were shown.

As shown in FIGS. 16 and 17, the lethality of the mice that had been treated with the test compound of Example 9 was significantly suppressed. In addition, the test compound of Example 9 was administered to mice, three hours after infection with *Pseudomonas aeruginosa*. As a result, the lethality of the mice was significantly suppressed (FIG. 18).

Test Example 13

<Septicemia Observation>

An emulsion solution containing 100 μg/mouse test compound (Example 9) was intraperitoneally administered to the mice. Twenty-four hours later, the mice were infected with $3.0 \times 10^{10}$ CFU/mL *Pseudomonas aeruginosa*. Fifteen hours after administration of the bacteria, blood was collected from the heart using an injection with a needle tip containing a small amount of heparin, and 200 μL of whole blood was then inoculated on a common agar medium. Thereafter, it was incubated in an incubator for 16 hours. Subsequently, the number of colonies on the medium was counted.

When there were a large number of cells, whole blood was diluted with a normal saline solution by a factor of 10, 100, 1000 or 10000, and the thus diluted solution was inoculated on a common agar medium.

Figure 19:
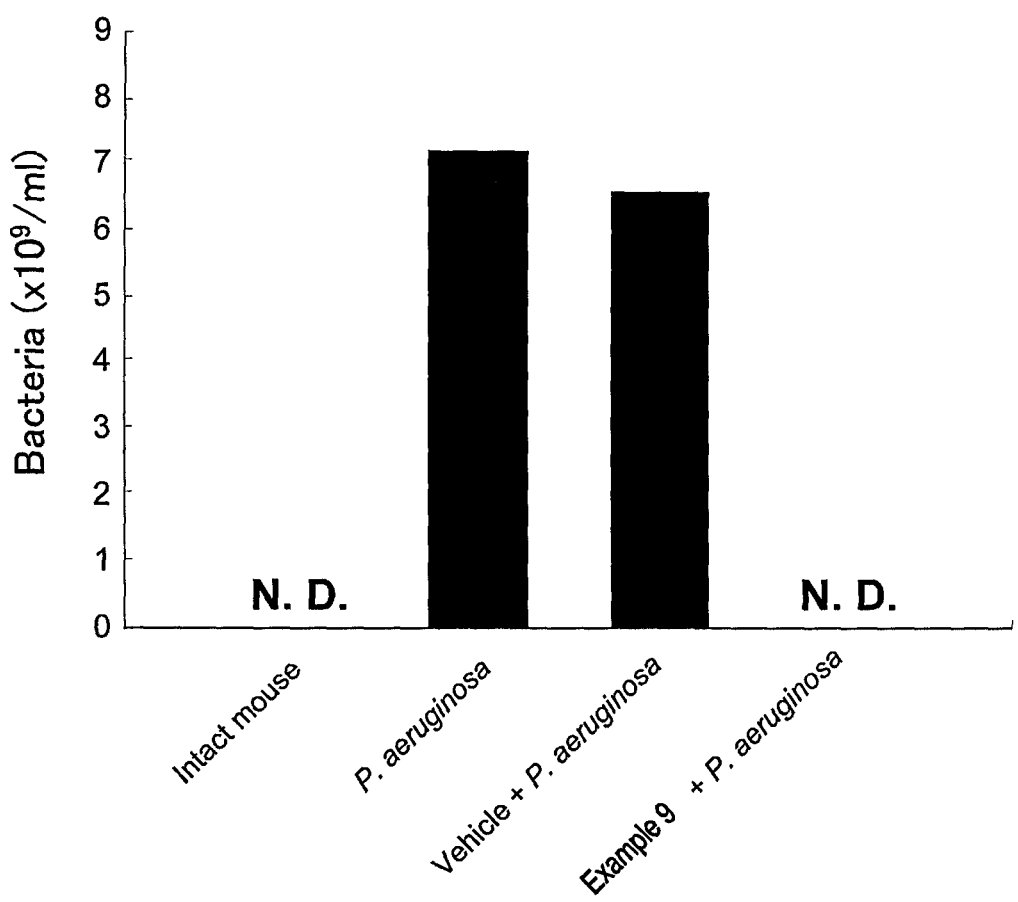
FIG. 19 shows the number of *Pseudomonas aeruginosa* cells in mouse blood, in a case in which *Pseudomonas aeruginosa* was administered to mice, to which a vehicle or the test compound of the present invention had been administered.

As a result, as shown in FIG. 19, when only the bacteria were administered, or when the bacteria and a vehicle were administered, the bacteria were detected in mouse blood. However, when the test compound of Example 9 was administered, the bacteria were not detected in mouse blood.

Test Example 14

<Antitumor Effects>

Figure 20:
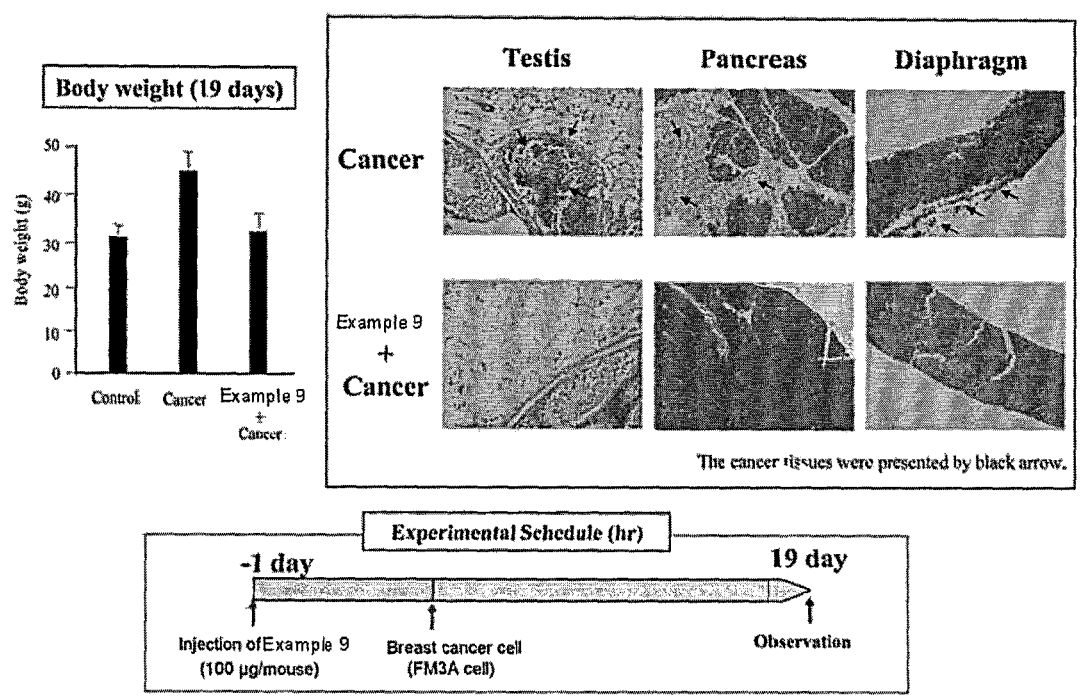
FIG. 20 shows the influence of TDCM, a vehicle or the test compound of the present invention on cancer metastasis in breast cancer cell-inoculated mice.

The 100 μg/mouse test compound obtained in Example 9 (emulsion solution) was intraperitoneally administered to each mouse, and twenty-four hours later, breast cancer cells (FM3A cells) were inoculated into the abdominal cavity thereof. Nineteen days later, the body weight of each mouse was measured. In addition, the tissue sections of diaphragm, pancreas and testis were subjected to HE staining, and they were then observed under a microscope. As a result, the body weight of the breast cancer cell-inoculated mouse was increased by approximately 10 g, when compared with a control mouse, and it was observed that the mouse contained a large amount of ascites fluid. Moreover, significant infiltration and metastasis of the cancer cells were observed in the diaphragm, pancreas and testis of the breast cancer cell-inoculated mouse. On the other hand, in the case of a mouse, into which the breast cancer cells were inoculated, after the mouse had been treated with the test compound of the example, the body weight of the mouse was equivalent to that of a control mouse. Moreover, infiltration and metastasis of the cancer cells into various organs were not observed at all (FIG. 20).

The trehalose compound of the present invention has immunostimulatory action that is superior to or equivalent to that of TDCM. Moreover, the present trehalose compound has toxicity that is significantly lower than that of TDCM. Thus, this compound can be preferably used as a pharmaceutical product. It was found that the toxicity of the compound of the present application is low, not only in model mice, but also in human-derived cells. Furthermore, it was also shown that the compound of the present application has low mutagenicity.

Further, a β-hydroxyl group was replaced by a hydrogen atom, and α-branched or β-branched fatty acid, wherein the branched carbon chain (which is a portion represented by $R_1$, $R_2$, $R_1'$ or $R_2'$ in the formula (1)) consists of approximately 7 to 20 carbon atoms, was used, and these components were successively synthesized and examined. As a result, it was found that, among trehalose compounds having various structures, a α-branched compound containing 10 carbon atoms or a β-branched compound containing 9, 13 or 14 carbon atoms, has maximum activity. Moreover, it was also found that the cancer-inducing activity of an amide bond can also be suppressed by substituting the amide bond of the prior art technique with an ester bond.

Still further, the trehalose compound of the present invention was found to be significantly useful even in in vivo tests, in that the present compound reduced the lethality of mice, to which Welch *bacillus* had been intraperitoneally administered. The point that the present trehalose compound reduces the lethality of mice, to which toxin generated by Welch *bacillus* had been intraperitoneally administered, is revolutionary. Moreover, it was also found that the excellent antibacterial activity of the trehalose compound of the present invention reduces the lethality of mice, to which *Pseudomonas aeruginosa* had been intraperitoneally administered.

Still further, with respect of the action mechanism of the trehalose compound of the present invention, it was demonstrated that when this compound was administered to mice, the $H_2O_2$ activity of neutrophil, the phagocytic ability of neutrophil, and the phagocytic ability of macrophage were enhanced. Thus, it is suggested that the aforementioned anti-infectious disease actions would be provided as a result of the activation of the cellular immunity of macrophage or neutrophil.

These test results suggest that the trehalose compound of the present invention would provide the activation of the cellular immunity of macrophage or neutrophil, and thus that it would be useful for a wide range of infectious diseases caused by bacteria, viruses, fungi and the like, which would be targets of the phagocytosis of macrophage or neutrophil. Accordingly, the trehalose compound of the present invention is more advantageous than other compounds of the prior art in that it involves a method that is more simple and reliable than the methods of the prior art, in which the causal bacterium as a target must be found when an antibiotic is used, and an antibiotic having an antibacterial spectrum to the causal bacterium must be appropriately selected, and also which has a risk regarding the appearance of a drug-resistant bacterium, and in which such a drug-resistant bacterium actually appeared, another antibiotic having an antibacterial spectrum to the drug-resistant bacterium must be appropriately selected.

Still further, in the present situation of the prior art techniques in which antibiotics are not effective for virus and thus virus infection must be prevented by administration of vaccine, the trehalose compound of the present invention may be useful in that it could provide a therapeutic agent for viruses.

Among the trehalose diester compounds of the present invention, a compound having particularly high activity had activity that was approximately 2 times higher than that of TDCM, and a compound having further particularly high activity had activity that was approximately 8 to 10 times higher than that of TDCM. It was demonstrated that these compounds are particularly useful in that they also have low toxicity.

Still further, cytokine response was measured after administration of the trehalose compound of the present invention. As a result, the release of IL-6, IFN-γ, and TNF-α all tended to increase. Moreover, both an in vitro test and an in vivo test were carried out. As a result, it was found that, among the compounds of the present invention, a compound having particularly high activity could bring on a significant increase in the aforementioned cytokines in the in vitro test, but that it could not increase the release of TNF-α so much in in vivo test. Furthermore, it was also found that, among the compounds of the present invention, such a compound having particularly high activity activates the release of IL-8 from human-derived THP-1 cells less strongly than TDCM does. Further, as a result of the measurement using human-derived THP-1 cells, A549 cells and DLD-1 cells, it was found that such a compound having a particularly high activity, among the compounds of the present invention, exhibited significant activity of activating the release of MIP-1β from THP-1 cells, whereas it did not particularly enhance the releasing activity of TNF-α.

Immunostimulation has been traditionally emphasized, and the induction of cytokine and chemokine is useful for activation of immunity. On the other hand, it has been known that, if immunity is excessively activated, it may rather have harmful effects, including anaphylactic shock and allergy as typical examples. The trehalose compound of the present invention does not excessively activate the release of inflammatory TNF-α or IL-8 known as a chemokine, which may become a factor of causing the aforementioned excessive inflammatory response. Although the present trehalose compound has immunostimulatory action, it is unlikely that immune response excessively acts to generate side effects such as inflammation. On the other hand, there is also case in which it is important that chemokine and the like are released at once to activate immunocytes in one process of immune response. Thus, there is also an aspect in which the release of a large amount of cytokine or chemokine is useful, depending on various conditions such as an infectious state and the physical conditions of an infected subject.

As stated above, because of the properties of cytokine or chemokine, there are three cases, namely, a case in which the release of a large amount of cytokine or chemokine is favorable, a case in which such release is unfavorable, and a case in which such release does not have particular importance. Thus, there are various cases depending on situation. When the release of IL-8 or TNF-α is desired, or when the release of IL-8 or TNF-α is not particularly important, a desired amount of specific type of the trehalose compound of the present invention can be used to accelerate the release of IL-8, TNF-α or the like or can be used without intending to suppress such release. Such use of the present trehalose compound is also included in the scope of the present invention.

Furthermore, it was found that the trehalose compound of the present invention significantly suppresses the growth of cancer cells in breast cancer cell-inoculated mice, to which the trehalose compound of the present invention has been administered, and that the present trehalose compound also suppresses infiltration or metastasis of the cancer cells into other organs. This demonstrates that the compound of the present application has antitumor activity.

Therefore, the usefulness and safety of the trehalose compound of the present invention as an anti-infectious disease therapeutic agent and as an anticancer agent can be clearly demonstrated.

[Industrial Applicability]

Since the trehalose compound provided by the present invention has high immunostimulatory activity and also has low toxicity, it is useful for the treatment of infectious diseases caused by pathogenic bacteria. Specifically, using the trehalose compound of the present invention, it is possible to provide a pharmaceutical product, which hardly causes a risk of having side effects such as the release of toxin due to destruction of cell masses upon administration of antibiotics, and which has action to reduce the toxicity of toxin owned by pathogenic bacteria. In addition, using the trehalose compound of the present invention, it is possible to provide a pharmaceutical product which has therapeutic effects on infectious diseases caused by multi-drug-resistant bacteria. Moreover, the compound of the present invention is also useful for the production of a low-risk pharmaceutical product, which may not cause a risk of generating excessive immune response.

Furthermore, by applying the method for producing a trehalose compound of the present invention, the trehalose compound according to the present invention can be efficiently synthesized in a large volume without involving asymmetric synthesis.

The invention claimed is:
1. A compound represented by the following formula (1):

[Formula 1]

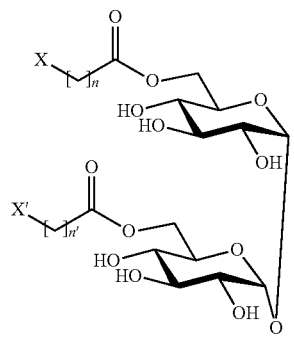

(Formula 1)

wherein X represents phenyl, naphthyl, or a group represented by $R_1$—$CHR_2$—, and X' represents phenyl, naphthyl, or a group represented by $R_1'$—$CHR_2'$—, wherein $R_1$, $R_1'$, $R_2$ and $R_2'$ independently represent a hydrogen atom or a $C_1$-$C_{21}$ alkyl group, and with regard to $R_1$, $R_1'$, $R_2$ and $R_2'$, a hydrogen atom in each alkyl group may be replaced by an alkoxy group, all or some of alkyl groups may form a 4- to 8-membered ring, and $R_1$ and $R_2$, and $R_1'$ and $R_2'$ may bind to each other to form a 4- to 8-membered ring, and wherein n and n' independently represent an integer of 0 to 3, with the proviso that the compound is not the following compounds:

(1) a compound, in which X represents $R_1$—$CHR_2$—, X' represents $R_1'$—$CHR_2'$—, $R_1$, $R_1'$, $R_2$ and $R_2'$ independently represent a hydrogen atom or an unsubstituted linear $C_1$-$C_6$ alkyl group, and n and n' represent 0;

(2) a compound, in which X represents $R_1$—$CHR_2$—, X' represents and any one of $R_1'$—$CHR_2'$—, $R_1$, $R_1'$, $R_2$ and $R_2'$ represent a $C_{14}$ linear alkyl group, and n and n' represent 0;

(3) a compound, in which X represents $R_1$—$CHR_2$—, X' represents $R_1'$—$CHR_2'$—, all of $R_1$, $R_1'$, $R_2$ and $R_2'$ represent a hydrogen atom, and n and n' independently represent 0 to 3;

(4) a compound, in which X represents $R_1$—$CHR_2$—, X' represents $R_1'$—$CHR_2'$—, any three of $R_1$, $R_1'$ $R_2$ and represent a hydrogen atom, the remaining one of $R_1$, $R_1'$, $R_2$ and $R_2'$ represents a $C_1$-$C_{21}$ linear alkyl group, and n and n' independently represent 0 to 3.

(5) a compound, in which X represents $R_1$—$CHR_2$—, X' represents $R_1'$—$CHR_2'$—, any one of $R_1$ and $R_2$ represents a hydrogen any one of $R_1'$ and $R_2'$ represents a hydrogen atom, and both the remaining one of $R_1$ and $R_2$ and the remaining one of $R_1'$ and $R_2'$ independently represent a $C_1$-$C_{21}$ linear alkyl group, and n and n' independently represent 0 to 3; and (6) a compound, in which X represents phenyl, X' represents phenyl, and n and n' represent 0.

2. The compound according to claim 1, wherein X represents $R_1$—$CHR_2$— and X' represents $R_1'$—$CHR_2'$—.

3. The compound according to claim 2, wherein $R_1$, $R_1'$, $R_2$ and $R_2'$ independently represent a linear C7-C12 and C16-C21 alkyl group, and n and n' independently represent 0 or 1.

4. The compound according to claim 2, wherein $R_1$, $R_1'$, $R_2$ and $R_2'$ independently represent a linear C7-C12' and C16 alkyl group, and n and n' independently represent 0.

5. The compound according to claim 2, wherein $R_1$, $R_1'$, $R_2$ and $R_2'$ independently represent a linear $C_9$-$C_{14}$ alkyl group, and n and n' independently represent 1.

6. The compound according to claim 1, wherein $R_1$ is identical to $R_1'$, $R_2$ is identical to $R_2'$, and n is identical to n'.

7. The compound according to claim 1, which is any of the following compounds:
   6,6'-bis-O-(2-octyldecanoyl)-α,α'-trehalose,
   6,6'-bis-O-(2-nonylundecanoyl)-α,α'-trehalose,
   6,6'-bis-O-(2-decyldodecanoyl)-α,α'-trehalose,
   6,6'-bis-O-(2-undecyltridecanoyl)-α,α'-trehalose,
   6,6'-bis-O-(2-dodecyltetradecanoyl)-α,α'-trehalose,
   6,6'-bis-O-(2-tridecylpentadecanoyl)-α,α'-trehalose,
   6,6'-bis-O-(2-pentadecylheptadecanoyl)-α,α'-trehalose, and
   6,6'-bis-O-(2-hexadecyloctadecanoyl)-α,α'-trehalose.

8. The compound according to claim 1, which is any of the following compounds:
   6,6'-bis-O-(3-nonyldodecanoyl)-α,α'-trehalose,
   6,6'-bis-O-(3-decyltridecanoyl)- α,α'-trehalose,
   6,6'-bis-O-(3-undecyltetradecanoyl)-α,α'-trehalose,
   6,6'-bis-O-(3-dodecylpentadecanoyl)-α,α'-trehalose,
   6,6'-bis-O-(3-tridecylhexadecanoyl)-α,α'-trehalose, and
   6,6'-bis-O-(3-tetradecylheptadecanoyl)-α,α'-trehalose.

9. The compound according to claim 1, which is any of the following compounds:
   6,6'-bis-O-(2-decyldodecanoyl)-α,α'-trehalose,
   6,6'-bis-O-(3-nonyldodecanoyl)-α,α'-trehalose,
   6,6'-bis-O-(3-tridecylhexadecanoyl)-α,α'-trehalose, and
   6,6'-bis-O-(3-tetradecylheptadecanoyl)-α,α'-trehalose.

10. A pharmaceutical composition comprising the compound according to claim 1 and a pharmaceutically acceptable carrier.

11. A pharmaceutical composition comprising the compound according to claim 2 and a pharmaceutically acceptable carrier.

12. A pharmaceutical composition comprising the compound according to claim 3 and a pharmaceutically acceptable carrier.

13. A pharmaceutical composition comprising the compound according to claim 4 and a pharmaceutically acceptable carrier.

\* \* \* \* \*